US007695716B2

(12) United States Patent
Drachman et al.

(10) Patent No.: US 7,695,716 B2
(45) Date of Patent: Apr. 13, 2010

(54) METHODS OF TREATING NEOPLASTIC, AUTOIMMUNE AND INFLAMMATORY DISEASES

(75) Inventors: Jonathan G. Drachman, Bothell, WA (US); May Kung Sutherland, Bothell, WA (US); Eric Sievers, Bothell, WA (US); Grant Risdon, Bothell, WA (US); Alan Wahl, Bothell, WA (US); Tim Lewis, Bothell, WA (US)

(73) Assignee: Seattle Genetics, Inc., Bothell, WA (US)

( * ) Notice: Subject to any disclaimer, the term of this patent is extended or adjusted under 35 U.S.C. 154(b) by 13 days.

(21) Appl. No.: 12/101,785

(22) Filed: Apr. 11, 2008

(65) Prior Publication Data

US 2008/0267960 A1 Oct. 30, 2008

Related U.S. Application Data

(63) Continuation-in-part of application No. PCT/US2007/083508, filed on Nov. 2, 2007.

(60) Provisional application No. 60/856,530, filed on Nov. 2, 2006, provisional application No. 60/874,439, filed on Dec. 11, 2006, provisional application No. 60/943,021, filed on Jun. 8, 2007.

(51) Int. Cl.
*A61K 39/395* (2006.01)
(52) U.S. Cl. .............. 424/133.1; 424/153.1; 424/156.1; 424/173.1; 424/174.1
(58) Field of Classification Search ........................ None
See application file for complete search history.

(56) References Cited

U.S. PATENT DOCUMENTS

| 5,693,761 | A | 12/1997 | Queen et al. |
|---|---|---|---|
| 5,730,982 | A | 3/1998 | Scheinberg |
| 6,007,814 | A | 12/1999 | Scheinberg |
| 6,599,505 | B1 | 7/2003 | Rosenblum |
| 6,653,104 | B2 | 11/2003 | Goldenberg |
| 2004/0058414 | A1 | 3/2004 | Queen et al. |
| 2004/0213796 | A1 | 10/2004 | Goldenberg et al. |
| 2006/0140936 | A1 | 6/2006 | Goldenberg et al. |
| 2006/0177455 | A1 | 8/2006 | Hoffee et al. |
| 2006/0204502 | A1 | 9/2006 | Borea et al. |

FOREIGN PATENT DOCUMENTS

WO WO 2008/058021 A2 5/2008

OTHER PUBLICATIONS

Abstract of Giles et al (Blood, Nov. 16, 2006, vol. 108, No. 11, p. 216B).*
Abstract of Raza et al (Blood, Nov. 16, 2006, vol. 108, No. 11, part 2, pp. 221B-222B).*
PCT International Search Report and Written Opinion of Mar. 17, 2008 for application PCT/US07/83508.
Jedema, et al., "Internalization and cell cycle-dependent killing of leukemic cells by Gemtuzumab Oazogamicin: rational for efficacy in CD33-negative malignancies with endocytic capacity", *Leukemia*, 18:316-325, (2004).
Garnache-Ottou, F. et al., "Expression of the myeloid-associated marker CD33 is not an exclusive factor for leukemic plasmacytoid dendrtic cells", *Blood*, 105:1256-1264, (2005).
U.S. Appl. No. 12/513,313, filed May 1, 2009, Drachman.
Allavena et al., "The Role of Chemokines and their Receptors in Tumor Progression and Invasion: Potential New Target of Biological Therapy", *Current Cancer Therapy Reviews* 1(1): 81-92 (2005).
Balkwill, "Cancer and the Chemokine Network", *Nature Reviews: Cancer* 4: 540-549 (2004).
Caron et al., "A Phase 1B trial of humanized monoclonal antibody M195 (anti-CD33) in myeloid leukemia: specific targeting without immunogenicity", *Blood* 83: 1760-1768 (1994).
Caron et al., "Anti-CD33 Monoclonal Antibody M195 for the Therapy of Myeloid Leukemia", *Leukemia and Lymphoma* 11(2): 1-6 (1993).
Caron et al., "Biological and Immunological Features of Humanized M195 (Anti-CD33) Monoclonal Antibodies", *Cancer Research* 52: 6761-6767 (1992).
Caron et al., "Supersaturating Infusional Humanized Anti-CD33 Monoclonal Antibody HuM195 in Myelogenous Leukemia", *Clinical Cancer Research* 4: 1421-1428 (1998).
ClinicalTrials.gov Identifier NCT00002609, "Phase II Study of MOAB HuM195 as Early Post Remission Therapy Followed by Cytarabine and Idarubicin and Maintenance With HuM195 for Acute Promyelocytic Leukemia in Clinical Complete Remission", Study Chair: David A. Scheinberg, MD, PhD, first received Nov. 1, 1999. As updated Dec. 8, 2005, downloaded from http://clinicaltrials.gov/archive/NCT00002609/2005_12_08.
ClinicalTrials.gov Identifier NCT00002609, "Phase II trial of post-remission therapy with Hum195 and Cytotoxic chemotherapy for acute promyelocytic leukemia", Study Chair: David A. Scheinberg, MD, PhD, first received Nov. 1, 1999. As updated Oct. 29, 2007, downloaded from http://clinicaltrials.gov/archive/NCT00002609/2007_10_29.
ClinicalTrials.gov Identifier NCT00002609, "Phase II trial of post-remission therapy with Hum195 and Cytotoxic chemotherapy for acute promyelocytic leukemia", Study Chair: David A. Scheinberg, MD, PhD, first received Nov. 1, 1999. As updated Feb. 6, 2009 downloaded from http://www.clinicaltrials.gov/ct2/show/NCT00002609?term=Lintuzumab&rank=6.
ClinicalTrials.gov Identifier NCT00002800, "Phase II study of high dose cytarabine combined with a Single high dose of idarubicin for newly diagnosed Patients with AML: the AML-3 protocol", first received Nov. 1, 1999. As updated Oct. 29, 2007, downloaded from http://www.clinicaltrials.gov/archive/NCT00002800/2007_10_29.
ClinicalTrials.gov Identifier NCT00003984, "Phase II Study of Monoclonal Antibody HuG1-M195 in Patients With High Risk Primary Myelodysplastic Syndromes", Study Chair: Heinz Zwierzina, MD, first received Nov. 1, 1999. As updated Dec. 8, 2005, downloaded from http://www.clinicaltrials.gov/archive/NCT00003984/2005_12_08.

(Continued)

*Primary Examiner*—Karen A Canella
(74) *Attorney, Agent, or Firm*—Townsend and Townsend and Crew LLP

(57) ABSTRACT

Methods of treating cancer and autoimmune and inflammatory diseases are provided.

38 Claims, 32 Drawing Sheets

OTHER PUBLICATIONS

ClinicalTrials.gov Identifier NCT00003984, "Phase II Trial With A Recombinant Humanized Anti-CD33 Monoclonal Antibody (HuM195) in Patients with High Risk Primary Myelodysplastic Syndromes", Study Chair: Heinz Zwierzina, MD, first received Nov. 1, 1999. As updated May 3, 2007, downloaded from http://www.clinicaltrials.gov/archive/NCT00003984/2007_05_03.

ClinicalTrials.gov Identifier NCT00003984, "Phase II Trial With A Recombinant Humanized Anti-CD33 Monoclonal Antibody (HuM195) in Patients with High Risk Primary Myelodysplastic Syndromes", Study Chair: Heinz Zwierzina, MD, first received Nov. 1, 1999. As updated Oct. 29, 2007, downloaded from http://www.clinicaltrials.gov/archive/NCT00003984/2007_10_29.

ClinicalTrials.gov Identifier NCT00003984, "Phase II Trial With A Recombinant Humanized Anti-CD33 Monoclonal Antibody (HuM195) in Patients with High Risk Primary Myelodysplastic Syndromes", Study Chair: Heinz Zwierzina, MD, first received Nov. 1, 1999. As updated Feb. 6, 2009, downloaded from http://www.clinicaltrials.gov/ct2/show/NCT00003984?term=lintizumab&rank=9.

ClinicalTrials.gov Identifier NCT00006045, "Phase III Randomized Study of Mitoxantrone, Etoposide, and Cytarabine (MEC) With or Without Monoclonal Antibody HuG1-M195 In Patients With Refractory or Relapsed Acute Myelogenous Leukemia", Study Chair: Daniel Levitt, MD, PhD, first received Jul. 5, 2000. As updated Dec. 8, 2005, downloaded from http://clinicaltrials.gov/archive/NCT00006045/2005_12_08.

ClinicalTrials.gov Identifier NCT00006045, "Phase III, Randomized, Multicenter Study to Assess the Efficacy and Safety of HuM195 (Recombinant Humanized Anti-CD33 Monoclonal Antibody) in Combination With Standardized Chemotherapy Compared to Standardized Chemotherapy Alone in the Treatment of Patients With Refractory or First-Relapsed Acute Myelogenous Leukemia (AML)", Study Chair: Daniel Levitt, MD, PhD, first received Jul. 5, 2000. As updated Feb. 9, 2007, downloaded from http://clinicaltrials.gov/archive/NCT00006045/2007_02_09.

ClinicalTrials.gov Identifier NCT00006045, "Phase III, Randomized, Multicenter Study to Assess the Efficacy and Safety of HuM195 (Recombinant Humanized Anti-CD33 Monoclonal Antibody) in Combination With Standardized Chemotherapy Compared to Standardized Chemotherapy Alone in the Treatment of Patients With Refractory or First-Relapsed Acute Myelogenous Leukemia (AML)", Study Chair: Daniel Levitt, MD, PhD, first received Jul. 5, 2000. As updated Oct. 29, 2007, downloaded from http://clinicaltrials.gov/archive/NCT00006045/2007_10_29.

ClinicalTrials.gov Identifier NCT00006045, "Phase III, Randomized, Multicenter Study to Assess the Efficacy and Safety of HuM195 (Recombinant Humanized Anti-CD33 Monoclonal Antibody) in Combination With Standardized Chemotherapy Compared to Standardized Chemotherapy Alone in the Treatment of Patients With Refractory or First-Relapsed Acute Myelogenous Leukemia (AML)", Study Chair: Daniel Levitt, MD, PhD, first received Jul. 5, 2000. As updated Feb. 6, 2009, downloaded from http://www.clinicaltrials.gov/ct2/show/NCT00006045?term=lintuzumab&rank=7.

ClinicalTrials.gov Identifier NCT00006084, "Phase II, Open-Label Study of HuM195 (Humanized Anti-CD33 Monoclonal Antibody) Administered to Patients With Acute Myelogenous Leukemia (AML) Who Are Documented Regimen Failures (RF) of the Control Arm of Study 195-301", Study Chair: Christos E. Emmanouilides, MD, first received Aug. 3, 2000. As updated Feb. 6, 2009, downloaded from http://www.clinicaltrials.gov/ct2/show/NCT00006084?term=Lintuzumab&rank=10.

ClinicalTrials.gov Identifier NCT00283114, Seattle Genetics, Inc. "A Phase 1, Multi-Dose Study of SGN-33 (Anti-huCD33 mAb; HuM195; Lintuzumab) in Patients With Acute Myeloid Leukemia and Myelodysplastic Syndrome", Study Director: Eric Sievers, M.D., first received Jan. 25, 2006. As updated Jul. 24, 2006, downloaded from http://clinicaltrials.gov/archive/NCT00283114/2006_07_24.

ClinicalTrials.gov Identifier NCT00283114, Seattle Genetics, Inc. "A Phase 1, Multi-Dose Study of SGN-33 (Anti-huCD33 mAb; HuM195; (Lintuzumab) in Patients With Acute Myeloid Leukemia and Myelodysplastic Syndrome", Study Director: Eric Sievers, M.D., first received Jan. 25, 2006. As updated Dec. 23, 2008, downloaded from http://www.clinicaltrials.gov/ct2/show/NCT00283114?term=lintuzumab&rank=3.

ClinicalTrials.gov Identifier NCT00283114, Seattle Genetics, Inc. "A Phase 1, Multi-Dose Study of SGN-33 (Anti-huCD33 mAb; HuM195; Lintuzumab) in Patients With Acute Myeloid Leukemia and Myelodysplastic Syndrome", Study Director: Eric Sievers, M.D., first received Jan. 25, 2006. As updated Feb. 2, 2007, downloaded from http://clinicaltrials.gov/archive/NCT00283114/2007_02_02.

ClinicalTrials.gov Identifier NCT00283114, Seattle Genetics, Inc. "A Phase 1, Multi-Dose Study of SGN-33 (Anti-huCD33 mAb; HuM195; (Lintuzumab) in Patients With Acute Myeloid Leukemia and Myelodysplastic Syndrome", Study Director: Eric Sievers, M.D., first received Jan. 25, 2006. As updated Jul. 21, 2006, downloaded from http://clinicaltrials.gov/archive/NCT00283114/2006_07_21.

ClinicalTrials.gov Identifier NCT00283114, Seattle Genetics, Inc. "A Phase 1, Multi-Dose Study of SGN-33 (Anti-huCD33 mAb; HuM195; (Lintuzumab) in Patients With Acute Myeloid Leukemia and Myelodysplastic Syndrome", Study Director: Eric Sievers, M.D., first received Jan. 25, 2006. As updated Mar. 6, 2007, downloaded from http://clinicaltrials.gov/archive/NCT00283114/2007_03_06.

ClinicalTrials.gov Identifier NCT00502112, "A Phase I Combination Trial of SGN-33 (Anti-huCD33 mAb; HuM195 Lintuzumab) and Lenalidomide (Revlimid®) in Patients With Myelodysplastic Syndromes (MDS)", Seattle Genetics, Inc., Study Director: Eric Sievers, MD, first received Jul. 13, 2007. As updated Jul. 16, 2007, downloaded from http://clinicaltrials.gov/archive/NCT00502112/2007_07_16.

ClinicalTrials.gov Identifier NCT00502112, "A Phase I Combination Trial of SGN-33 (Anti-huCD33 mAb; HuM195 Lintuzumab) and Lenalidomide (Revlimid®) in Patients With Myelodysplastic Syndromes (MDS)", Seattle Genetics, Inc., Study Director: Eric Sievers, MD, first received Jul. 13, 2007. As updated May 5, 2009, downloaded from http://clinicaltrials.gov/ct2/show/NCT00502112?term=lintuzumab&rank=1.

ClinicalTrials.gov Identifier NCT00502112, "A Phase I Combination Trial of SGN-33 (Anti-huCD33 mAb; HuM195 Lintuzumab) and Lenalidomide (Revlimid®) in Patients With Myelodysplastic Syndromes (MDS)", Seattle Genetics, Inc., Study Director: Eric Sievers, MD, first received Jul. 13, 2007. As updated Oct. 31, 2007, downloaded from http://clinicaltrials.gov/archive/NCT00502112/2007_10_31.

ClinicalTrials.gov Identifier NCT00502112, "A Phase I Combination Trial of SGN-33 (Anti-huCD33 mAb; HuM195 Lintuzumab) and Lenalidomide (Revlimid®) in Patients With Myelodysplastic Syndromes (MDS)", Seattle Genetics, Inc., Study Director: Eric Sievers, MD, first received Jul. 13, 2007. As updated Aug. 3, 2008, downloaded from http://clinicaltrials.gov/archive/NCT00502112/2008_08_03.

ClinicalTrials.gov Identifier NCT00528333, Seattle Genetics, Inc., Study Director: Eric Sievers, MD, first received Sep. 10, 2007. As updated Feb. 25, 2009, downloaded from http://www.clinicaltrials.gov/ct2/show/NCT00528333?term=lintuzumab&rank=2.

ClinicalTrials.gov Identifier NCT00528333, Seattle Genetics, Inc., Study Director: Eric Sievers, MD, first received Sep. 10, 2007. As updated Sep. 11, 2007, downloaded from http://clinicaltrials.gov/archive/NCT00528333/2007_09_11.

ClinicalTrials.gov Identifier NCT00528333, Seattle Genetics, Inc., Study Director: Eric Sievers, MD, as updated Sep. 13, 2007, downloaded from http://clinicaltrials.gov/archive/NCT00528333/2007_09_13.

Colombo et al., "Targeting Myelomonocytic Cells to Revert Inflammation-Dependent Cancer Promotion", *Cancer Res* 65(20): 9113-9116 (2005).

Feldman et al., "Phase III Randomized Multicenter Study of a Humanized Anti-CD33 Monoclonal Antibody, Lintuzumab, in Combination With Chemotherapy, Versus Chemotherapy Alone in Patients With Refractory of First-Relapsed Acute Myeloid Leukemia", *J. Clinical Oncology* 23(18): 4110-4116 (2005).

Feldman et al., "Treatment of relapsed or refractory acute myeloid leukemia with humanized anti-CD33 monoclonal antibody HuM195", *Leukemia* 17: 314-318 (2003).

Giles et al., "Cloretazine (VNP40101M), a Novel Sulfonylhydrazine Alkylating Agent, in Patients Age 60 Years or Older With Previously Untreated Acute Myeloid Leukemia", *J. Clinical Oncology* 25(1): 25-31 (2007).

Giles et al. "Phase I study of AVE9633, an antiCD33-maytansinoid immunoconjugate, administered as an intravenous infusion in patients with refractory/relapsed CD33-positive acute myeloid leukemia (AML)", Blood 108 (11):216B (2006) (abstract).

Gordon et al., "Cancer cachexia", *Q J Med* 98:779-788 (2005).

Jurcic et al., "Antibody therapy for residual disease in acute myelogenous leukemia", *Critical Reviews in Oncology/Hematology* 38: 37-45 (2001).

Jurcic et al., "Molecular Remission Induction with Retinoic Acid and Anti-CD33 Monoclonal Antibody HuM195 in Acute Promyelocytic Leukemia", *Clinical Cancer Research* 6: 372-380 (2000).

Kantarjian et al., "Results of a randomized study of 3 schedules of low-dose decitabine in higher-risk myelodysplastic syndrome and chronic myelomoncytic leukemia", *Blood* 109(1): 52-57 (2007).

Kossman et al., "A Phase I Trial of Humanized monoclonal Antibody HuM195 (anti-CD33) with Low-Dose Interleukin 2 in Acute Myelogenous Leukemia", *Clinical Cancer Research* 5: 2748-2755 (1999).

Löwenberg, "On the Road to New Drugs in Acute Myeloid Leukemia", *J. Clinical Oncology* 25(1): 1-2 (2007).

Meyers et al., "Cognitive Impairment, Fatigue, and Cytokine Levels in Patients with Acute Myelogenous Leukemia or Myelodysplastic Syndrome", *Cancer* 104(4): 788-793 (2005).

National Cancer Research Institute Acute Myeloid Leukaemia and High Risk MDS Trial 16, "A Programme of Development for Older Patients With Acute Myeloid Leukaemia and High Risk Myelodysplastic Syndrome" (Trial Reference ISRCTN 11036523). AML Version 5 (2006).

Peiper et al., "M9 CD33 cluster workshop report" (excerpt), *Leucocyte Typing V, While Cell Differentiation Antigens, Proceedings of the Fifth International Workshop and Conference Held in Boston*, Nov. 3-7, 1993, vol. 1, pp. 837-840 (1995).

Raza et al., "A humanized unconjugated antibody targeting CD33 (SGN-33; huM195) is active in patients with acute myeloid leukemia (AML) and myelodysplastic syndromes (MDS)", *J. Clin. Oncology 2006 ASCO Annual Meeting Proceedings Part I*, vol. 24, No. 18S: Jun. 20 Supplement Abstract No. 16500 (2006).

Raza et al., "Complete remissions observed in acute myeloid leukemia following prolonged exposure to lintuzumab, a phase 1 trial", *Leukemia & Lymphoma*, 1-9 (2009).

Raza et al., "Complete Remissions Observed in Acute Myeloid Leukemia Following Prolonged Exposure to SGN-33 (lintuzumab), a Humanized Monoclonal Antibody Targeting CD33", *Blood* 110(11) Abstract No. 159 (2007).

Raza et al., "Increased dose intensity of SGN-33, a humanized monoclonal antibody targeting CD33, is active and well-tolerated in patients with acute myeloid leukemia (AML) and myelodysplastic syndromes (MDS)", 48th Annual Meeting of the American Society of Hemotology, Orlando, FL, Dec. 9-12, 2006, *Blood* 108(11): Part 2, pp. 221 B-222B (2006) (abstract).

Raza et al., "Prolonged Exposure to Lintuzumab Monotherapy in Acute Myeloid Leukemia (AML) and Myelodysplastic Syndromes (MDS)—Results of a Phase 1 Trial", Abstract No. 983, 14th EHA Congress, Jun. 4-7, 2009 (poster).

Scheinberg et al., "A Phase I Trial of Monoclonal Antibody M195 in Acute Myelogenous Leukemia: Specific Bone Marrow Targeting and Internalization of Radionuclide", *J. Clinical Oncology* 9(3): 478-490 (1991).

Seattle Genetics—News Release, "Seattle Genetics Initiates SGN-33 Clinical Trial", Bothell, WA (Business Wire), Nov. 17, 2005.

Seruga et al., "Cytokines and their relationship to the symptoms and outcome of cancer", *Cancer* Advance Online Publication: 887-899 (2008).

Sgouros et al., "Modeling and Dosimetry of Monoclonal Antibody M195 (Anti-CD33) in Acute Myelogenous Leukemia", *J. Nuclear Medicine* 34(3): 422-430 (1993).

Sutherland et al., "Anti-leukemic activity of lintuzumab (SGN-33) in preclinical models of acute myeloid leukemia", *mAbs* 1(5): 1-10 (2009).

Sutherland et al., "SGN-33 (lintuzumab) Demonstrates Anti-Leukemic Activity in Preclinical Models of AML", *Amer. Soc. Hematology*, Atlanta, GA, Dec. 8-11, 2007 Abstract No. 919 (poster).

Sutherland et al., "SGN-33 (lintuzumab) Demonstrates Anti-Leukemic Activity in Preclinical Models of AML", *Amer. Soc. Hematology*, Atlanta, GA, Dec. 8-11, 2007 *Blood* 110(11) Abstract No. 919 (2007).

Sutherland et al., "SGN-33 (Lintuzumab), a humanized anti-CD33 antibody, modulates the activity of $CD33^+$ tumor-associated macrophages", *98th American Association Of Cancer Research Annual Meeting*, Apr. 14-18, 2007; Los Angeles, CA Abstract No. 4111.

Sutherland et al., "SGN-33 (Lintuzumab), a humanized anti-CD33 antibody, modulates the activity of $CD33^+$ tumor-associated macrophages", *98th American Association Of Cancer Research Annual Meeting*, Apr. 14-18, 2007; Los Angeles, CA Abstract No. 4111 (poster).

Sutherland et al., "SGN-33 Modulates Cytokine and Chemokine Production by Activated Monocytes and Macrophages", *Amer. Soc. Hematology*, Orlando, FL, Dec. 9-12, 2006 Abstract No. 1995 (poster).

Sutherland et al., "SGN-33 Modulates Cytokine and Chemokine Production by Activated Monocytes and Macrophages", *Amer. Soc. Hematology*, Orlando, FL, Dec. 9-12, 2006 Abstract No. 1995.

Sutherland et al., "SGN-33, lintuzumab, demonstrates anti-leukemic activity in MDR-positive preclinical models of AML" *American Association Of Cancer Research*, San Diego, CA, Apr. 12-16, 2008, Seattle Genetics, Inc. Abstract No. 1513 (poster).

Taussig et al., "Hematopoietic stem cells express multiple myeloid markers: implications for the origin and targeted therapy of acute myeloid leukemia", *Blood* 106(13): 4086-4092 (2005).

\* cited by examiner

METHODS OF TREATING NEOPLASTIC, AUTOIMMUNE AND INFLAMMATORY DISEASES

This application claims priority to International Application No. PCT/US07/83508, filed Nov. 2, 2007, which claims priority to U.S. Provisional Application No. 60/856,530 filed Nov. 2, 2006; U.S. Provisional Application No. 60/874,439 filed Dec. 11, 2006; and U.S. Provisional Application No. 60/943,021 filed Jun. 8, 2007, all of which are incorporated by reference in their entirety.

BACKGROUND OF THE INVENTION

Neoplastic diseases, also referred to as cancers, are a leading cause of illness and death throughout the world. Neoplastic diseases can be grouped into different classes, based on the types of cells involved. Solid tumors can originate from numerous cells types and generally form masses in a patient. In contrast, non-solid tumors, such as hematological malignancies, generally originate from cells of the blood, bone marrow or lymphatic system.

Some current therapies for hematological malignancies, e.g., various types of leukemia, are able to achieve a high rate of remission. Therapy to induce remissions typically involves dosing with regimens of cytotoxic agents (e.g., low or high dose cytarabine and daunomycin) and/or targeted delivery of cytotoxic agents (e.g., Mylotarg®, gemtuzamab ozogamicin, Wyeth). Such treatments are able to induce remissions. For example, treatment of patients with acute myeloid leukemia (AML) an induction regimen of cytarabine and anthracycline can induce remissions in most younger patients (i.e., less than 60 years of age). Consolidation regimens that include high-dose cytarabine, autologous or allogenic transplantation can extend remission intervals in younger patients with AML and can cure approximately one third of such patients who achieve remissions. Many patients, however, and in particular elderly patients, are untreatable with such agents because they cannot tolerant high doses of chemotherapeutic agents. In addition, a large percentage of such patients who achieve remission ultimately relapse. While a large body of work has addressed the early detection of relapse and of minimal residual disease, effective strategies for treating patients in remission to prevent or delay relapse or recurrence of the underlying hematological malignancy are lacking.

Although controversial, it has been suggested that non-malignant effector or accessory cells (e.g., monocytes and macrophages) may contribute to cancer growth and metastasis through the secretion of inflammatory mediators and growth factors, and the production of proteases. Tumor growth and progression have been linked to inflammation and the presence of tumor-associated macrophages (TAMs) (see, e.g., Colombo and Mantovani, 2005, Cancer Res. 65:9113-9116). Monocytes and macrophages form a major component of the inflammatory infiltrate associated with many carcinomas. Monocytes differentiate into macrophages (i.e., TAMs) in the cytokine- and chemokine-rich environments provided by the infiltrating cells and the tumor cells. TAMs secrete numerous pro-inflammatory cytokines and chemokines that enhance and promote the growth and metastases of tumors. High numbers of TAMs in cancer tissues have been linked to poor prognosis and patient survival in many cancers, including those of the breast, prostate, bladder, kidney, and esophagus (see, e.g., Lewis and Pollard, 2006, Cancer Res. 66:605-612).

Non-malignant monocytes and macrophages, including TAMs, may also play a role in cancer-associated cachexia. Patients with neoplastic disease often experience related cancer-associated challenges. Cancer-associated cachexia (also referred to as cancer cachexia) is a condition that occurs at high frequency in cancer patients and involves wasting, fever, night sweats and weight loss, often accompanied by anorexia. Cancer-associated cachexia is a major cause of morbidity and mortality in advanced cancer patients, in particular with cancers of the breast, prostate, lung, pancreas, and gastrointestinal tract. The cause of cancer-associated cachexia is still unknown; however, this condition is associated with a chronic, systemic inflammatory response and the elevation of acute phase proteins (see, e.g., Esper and Harb, 2005, Nutr. Clin. Pract. 20:369-376; Tisdale, 2001, Nutrition 17:438-442; Gordon et al., 2005, Q. J. Med. 98:779-788).

Inflammatory mediators, cytokines, chemokines and growth factors produced by non-malignant effector cells, alone or in concert with the tumor cells, include, but are not limited to, tumor necrosis factor-alpha (TNF-α), interleukin-1-beta (IL-1β), interleukin-6 (IL-6), interferon-gamma (IFN-γ), leukemia inhibitory factor (LIF), IP-10 and proteolysis-inducing factor (PIF). These inflammatory mediators, cytokines, chemokines and growth factors may play a role in cancer growth and progression, and are thought to contribute to the persistent inflammatory condition associated with cachexia.

A variety of pharmacological agents have been administered to patients with cancer-associated cachexia and/or tested in animal models. These treatments have been met, however, with only limited success (see, e.g., Illman et al., 2005, J. Support. Oncol. 3:37-50; Gordon et al., 2005, Q. J. Med. 98:779-788).

Just as in cancer, monocytes and macrophages are a major source of cytokines and chemokines believed to contribute to the pathology of acute and chronic autoimmune or inflammatory diseases (e.g., rheumatoid arthritis, inflammatory bowel disease, peritonitis, psoriasis, atopic dermatitis, psoriatic arthritis, and multiple sclerosis). These cells are involved in the recruitment, differentiation and maturation of more macrophages to the inflamed regions and in the release and activation of proteases that destroy tissues (see, e.g., Ma and Pope, 2005, Curr. Pharm. Design 11: 569-580; Bruck et al., 1996, Immunobiology 195:588-600; Liu and Pope, 2004, Rheum. Dis. Clin. N. Am. 30:19-39).

While there are no known cures for autoimmune and inflammatory diseases (e.g., rheumatoid arthritis, psoriasis), therapies are available to reduce inflammation and pain and tissue destruction. These therapies are not effective, however, in all patients and are associated with many side-effects.

New therapies are needed, therefore, for treating cancer, cancer-associated cachexia and autoimmune and inflammatory diseases to improve the quality of life and survival rates for patients with cancer or an autoimmune or inflammatory disease.

BRIEF SUMMARY OF THE INVENTION

The invention relates to methods of treating patients with cancer or autoimmune or inflammatory disease with agents that specifically bind to non-malignant effector or accessory cells. The invention also relates to methods of preventing or delaying recurrence of cancers, such as leukemia and related disorders. The invention further relates to methods for reducing inflammation and tissue damage associated with autoimmune or inflammatory diseases. The invention further provides pharmaceutical compositions for treating patients with cancer or autoimmune or inflammatory disease, and/or for preventing or delaying recurrence of leukemia in a patient.

In one aspect, the invention provides methods of treating cancer to delay progression, reduce tumor burden and/or reduce cancer-associated cachexia in a patient in need thereof by administering to the patient an effective regimen of a CD33 binding agent. The agent can specifically bind to CD33, such as CD33 on the surface of non-malignant effector or accessory cells (e.g., a monocyte, macrophage, tumor-associated macrophage, dendritic cell, or neutrophil). In some embodiments, the cells of the cancer are CD33 negative. In one embodiment, cells of the cancer are not known to express CD33 relative to normal tissue of the same type. In another embodiment, cells of the cancer are not known to overexpress CD33 relative to normal tissue of the same type.

In various embodiments, the cancer can be a CD33-negative or CD33-positive non-hematological malignancy or a hematological malignancy. The hematological malignancy can be, for example, acute lymphoid leukemia, chronic myelomonocytic leukemia, acute myeloid leukemia, an erythrocytic leukemia, acute megakaryoblastic leukemia, myelodysplastic syndrome, multiple myeloma, histiocytic lymphoma, a myeloid sarcoma, or a mast cell proliferative disorder.

In specific embodiments, the cancer is a CD33-negative non-hematological malignancy or a hematological malignancy. The agent specifically binds to CD33 expressed on effector cells, in particular inflammatory infiltrating cells (e.g., monocytes and macrophages) associated with the malignancy. The malignancy can be, for example, a myeloid proliferative disease or tumor of the breast, prostate, pancreas, esophagus, lung, or gastrointestinal tract.

In some embodiments, the agent is an unconjugated antibody. The antibody can be, for example, a humanized or chimeric antibody, such as a humanized or chimeric M195 antibody. In some embodiments, the antibody competes with M195 antibody for specific binding to CD33. In other embodiments, the antibody binds to the same epitope as M195 antibody. In other embodiments, the antibody can be bound (i.e., conjugated) to a cytotoxin. In some embodiments, the antibody is administered to the patient intravenously at a dose of from 2.5 to about 12 mg/kg.

In an embodiment, administration of the CD33 binding agent decreases the number of non-malignant effector or accessory cells displaying the antigen. In another embodiment, administration of the CD33 binding agent decreases the levels of one or more pro-inflammatory cytokines, chemokines or growth factors, in the patient. In a related embodiment, administration of the CD33 binding agent decreases the levels of one or more pro-inflammatory cytokines, chemokines or growth factors produced in vicinity of the cancer cells. The non-malignant effector cells can be, for example, monocytes, macrophages, dendritic cells and/or neutrophils. The macrophage can be a tumor-associated macrophage. The pro-inflammatory cytokine, chemokine or growth factor can be, for example, interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In another embodiment, the CD33 binding agent inhibits the migration of macrophages in the vicinity of the cancer cells. In a related embodiment, the CD33 binding agent decreases the number of macrophages in the vicinity of the cancer cells. The macrophages can be, for example, a tumor-associated macrophage.

In some embodiments, the methods further include monitoring the number of non-malignant effector cells, and/or the levels of one or more pro-inflammatory cytokines, chemokines or growth factors, in the patient (e.g., in the vicinity of the tumor). The dosage of the CD33 binding agent can be adjusted based on the monitoring.

In some embodiments, the patient has cancer-associated cachexia. The patient can be monitored for the extent of cancer-associated cachexia responsive to the administration of the agent. The dosage of antibody administered to the patient can be adjusted based on the monitoring.

In another embodiment, the patient does not have detectable cancer-associated cachexia.

In one embodiment, the CD33 binding agent (e.g., an antibody) is administered to the patient in combination with one or more therapeutic agents effective against the cancer. The therapeutic agent can be, for example, a chemotherapeutic agent, a radiotherapeutic agent, a therapeutic antibody, a small molecule drug, an antisense or siRNA drug, or a peptide drug. In an embodiment, the therapeutic agent is a chemotherapeutic agent, such as, for example, VELCADE® (Bortezomib) or REVLIMID® (lenalidomide), cytosine arabinoside (cytarabine; Ara-C), VIDAZA® (azacitidine), daunorubicin, idarubicin, 6-thioguanine or mithramycin.

In another aspect, the invention provides a method of delaying progression of a non-hematological malignancy, reducing tumor burden, and/or reducing cancer-associated cachexia by administering to a patient with a non-hematological malignancy an effective regimen of an antibody that specifically binds to CD33. The non-hematological malignancy can be, for example, CD33 negative. In one embodiment, cells of the cancer are not known to express CD33 relative to normal tissue of the same type. In another embodiment, cells of the cancer are not known to overexpress CD33 relative to normal tissue of the same type. In some embodiments, the progression of the non-hematological malignancy is delayed, the tumor burden is reduced, and/or the cancer-associated cachexia is reduced.

In another aspect, methods of preventing relapse of cancer in a patient are provided by administering an effective regimen of a CD33 binding agent. In some embodiments, the patient is free of detectable cancer characterized by expression or overexpression of CD33 on the surface of a cancer cell relative to a normal cell of the same tissue. The cancer can be, for example, acute myeloid leukemia (AML), chronic myeloid leukemia (CML), chronic myelomonocytic leukemia, thrombolytic leukemia, a myelodysplastic syndrome, a myeloproliferative disorder, refractory anemia, a preleukemia syndrome, a lymphoid leukemia, or an undifferentiated leukemia.

In a related aspect, methods of preventing or delaying recurrence of a hematological malignancy (e.g., leukemia) in a patient are provided by administering to the patient in remission from the hematological malignancy an effective regimen of a CD33 binding agent (e.g., an antibody) that specifically binds to CD33 on the surface of leukemic cells from the underlying hematological malignancy. The recurrence of the hematological malignancy is prevented or delayed. In some embodiments, the patient is free of detectable cancer characterized by overexpression of CD33 on the surface of a cancer cell relative to a normal cell of the same tissue.

The hematological malignancy can be, for example, acute myeloid leukemia (AML), chronic myeloid leukemia (CML), chronic myelomonocytic leukemia, thrombolytic leukemia, a myelodysplastic syndrome, a myeloproliferative disorder, refractory anemia, a preleukemia syndrome, a lymphoid leukemia, or an undifferentiated leukemia.

In some embodiments, the patient in remission from the hematological malignancy has not undergone a bone marrow transplant. In another related embodiment, the patient in remission from the hematological malignancy has undergone a bone marrow transplant. The bone marrow transplant can be either an autologous or an allogeneic bone marrow transplant.

In another aspect, methods are provided for treating an autoimmune or inflammatory disease by administering to the patient an effective regimen of a CD33 binding agent that specifically binds to CD33. In one embodiment, administration of the CD33 binding agent decreases the number of involved non-malignant effector or accessory cells displaying the antigen, and/or decreases the levels of one or more pro-inflammatory cytokines, chemokines or growth factors, in the patient. In related embodiments, the CD33 binding agent inhibits the migration of macrophages to the affected area(s) of the patient, and/or decreases the number of macrophages in the affected area(s) of the patient.

The non-malignant effector cells can be monocytes, macrophages, dendritic cells and/or neutrophils. The pro-inflammatory cytokines, chemokines or growth factors can be, for example, interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In some embodiments, the patient has an autoimmune or inflammatory disease such as, for example, inflammatory bowel disease, psoriasis, atopic dermatitis, psoriatic arthritis, or rheumatoid arthritis. In some embodiments, the patient can be monitored for symptoms associated with the disease including, but not limited to, pain, swelling, discomfort, diarrhea, anemia, weight loss, joint deformity, blood levels of cytokines, and/or levels of inflammatory infiltrating cells in the affected area(s). The dosage of the agent administered to the patient can be adjusted based on the monitoring.

In a specific embodiment, methods are provided for reducing the pain, swelling, discomfort, and inflammation in a patient with an autoimmune or inflammatory disease by administering to the patient an effective regimen of an antibody that specifically binds to CD33.

In a related embodiment, methods are provided for reducing pro-inflammatory cytokine and/or chemokine levels in the blood of the patient by administering to the patient an effective regimen of a CD33 binding agent. The pro-inflammatory cytokines or chemokines can be, for example, interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In a related embodiment, method are provided for reducing the levels of inflammatory infiltrating cells in the affected area(s) of a patient with an autoimmune or inflammatory disease by administering to the patient an effective regimen of a CD33 binding agent.

The CD33 binding agent, such as an antibody, can be administered to the patient alone or in combination with one or more therapeutic agents effective for the treatment of autoimmune or inflammatory disease. The therapeutic agents can be, for example, a pain reliever such as aspirin or Tylenol® (acetaminophen), a nonsteroidal anti-inflammatory drug (NSAID) such as ibuprofen, a corticosteroid such as cortisone or prednisone, a therapeutic antibody such as etanercept (Enbrel™), infliximab (Remicade™) or anakinra (Kineret™), an immunomodulatory agent such as methotrexate, cyclophosphamide, or cyclosporine, an antibiotic such as Flagyl™ (Metronidazole) or Cipro™ (Ciprofloxacin), or small molecule compounds such as sulfasalazine (Azulfidine™) or hydroxychloroquine (Plaquenil™).

These and other aspects of the invention will best be understood by reference to the following detailed description of the embodiments, taken in conjunction with the accompanying drawings. The discussion below is descriptive, illustrative and exemplary and is not to be taken as limiting the scope defined by any appended claims.

BRIEF DESCRIPTION OF THE DRAWINGS

FIGS. 14 (14A, 14B and 14C) shows that an anti-CD33 antibody (SGN-33) blocks the migration of human macrophages in response to chemoattractants.

DEFINITIONS

Figure 1:
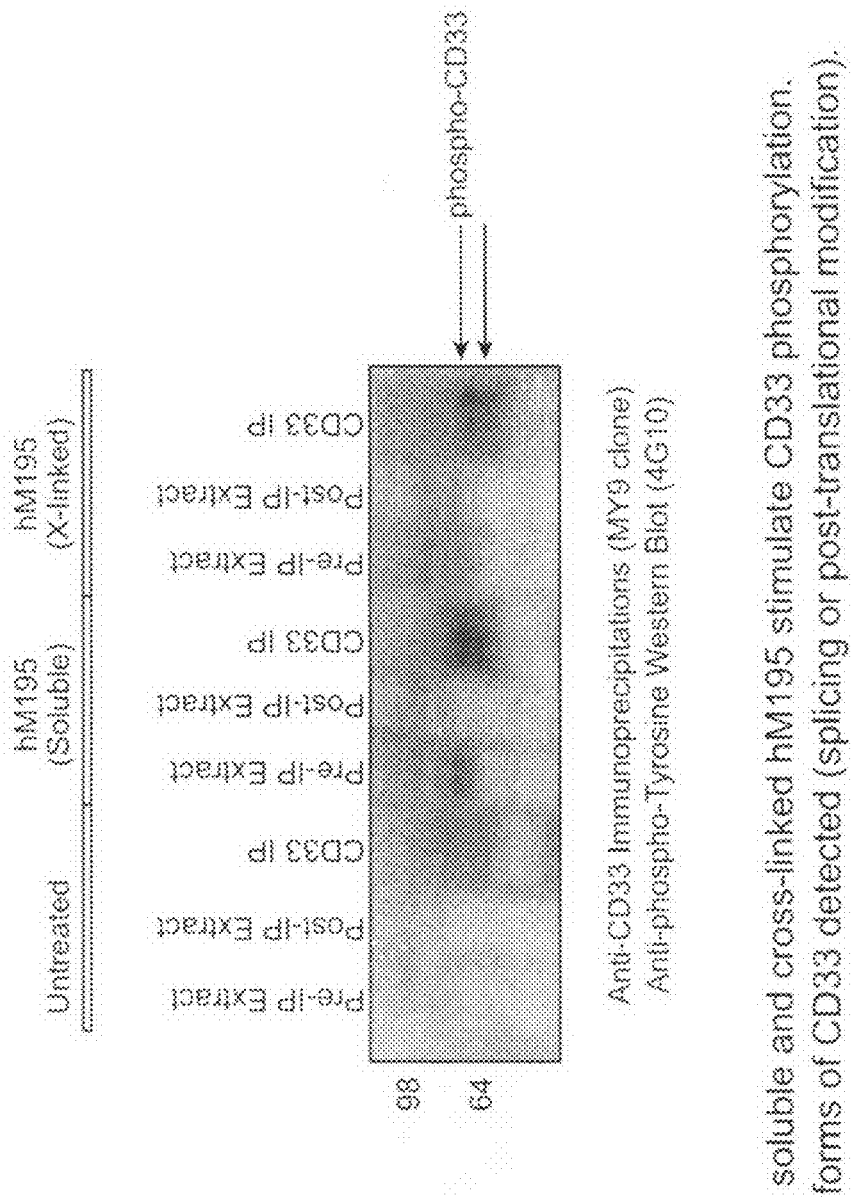
FIG. 1 shows a Western blot of CD33 phosphorylation in cell lysates prepared from a CD33-positive AML cell line, HL-60, treated with the indicated soluble or cross-linked anti-CD33 antibody (SGN-33, also referred to as lintuzumab or hM195, a humanized version of mouse monoclonal antibody M195). CD33 was immunoprecipitated using the MY9 anti-CD33 antibody. Phosphorylation of CD33 was detected using the 4G10 anti-phosphotyrosine antibody.

Unless stated otherwise, the following terms and phrases as used herein are intended to have the following meanings. Trade names as used herein are intended to independently include the trade name product formulation, the generic drug, and the active pharmaceutical ingredient(s) of the trade name product, unless otherwise indicated by context.

The term "binding agent" as used herein means a protein or peptide that specifically binds to a target antigen. A binding agent can be, for example, an antibody, a derivative of such an antibody, or other agent that specifically binds to the target antigen. A binding agent can also be a protein comprising an Fv region or a portion thereof (e.g., a $V_H$ or $V_L$ or a CDR(s) of an antibody that specifically binds to the target antigen).

The term "CD33 binding agent" as used herein refers to a binding agent that specifically binds to CD33, typically a portion of the extracellular domain of human CD33.

The term "antibody" as used herein refers to (a) immunoglobulin polypeptides and immunologically active portions of immunoglobulin polypeptides (i.e., polypeptides of the immunoglobulin family, or fragments thereof, that contain an antigen binding site that immunospecifically binds to a specific target antigen), or (b) conservatively substituted derivatives of such immunoglobulin polypeptides or fragments that immunospecifically bind to the target antigen. Antibodies are generally described in, for example, Harlow and Lane, *Antibodies: A Laboratory Manual* (Cold Spring Harbor Laboratory Press, 1988). The term "antibody" refers to intact monoclonal antibodies, polyclonal antibodies, monospecific antibodies, multispecific antibodies (e.g., bispecific antibodies), and antibody fragments that exhibit the desired biological activity (e.g., antigen-binding). The antibody can be of any type or class (e.g., IgG, IgE, IgM, IgD, and IgA) or sub-class (e.g., IgG1, IgG2, IgG3, IgG4, IgA1 and IgA2).

An "intact" antibody is one which comprises an antigen-binding variable region as well as a light chain constant domain ($C_L$) and heavy chain constant domains, $C_H1$, $C_H2$, $C_H3$, and $C_H4$, as appropriate for the antibody class. The constant domains may be native sequence constant domains (e.g., human native sequence constant domains) or amino acid sequence variants thereof.

An "antibody fragment" comprises a portion of an antibody, including the antigen-binding or variable region or a portion thereof. Examples of antibody fragments include Fab, Fab', F(ab')$_2$, and Fv fragments, $V_H$ and $V_L$ antigen binding fragments, diabodies, triabodies, tetrabodies, single-chain antibody, scFv, scFv-Fc, a SMIP, and multispecific antibodies formed from antibody fragment(s).

An antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity (CDC); Fc receptor binding; antibody-dependent cell-mediated cytotoxicity (ADCC); phagocytosis; down regulation of cell surface receptors (e.g., B cell receptor; BCR), etc.

"Single-chain Fv" or "scFv" antibody fragments comprise the $V_H$ and $V_L$ domains of an antibody, wherein these domains are present in a single polypeptide chain. The Fv polypeptide typically further comprises a polypeptide linker between the $V_H$ and $V_L$ domains which enables the scFv to form the desired structure for antigen-binding. For a review of scFv, see Plückthun in *The Pharmacology of Monoclonal Antibodies*, vol. 113, Rosenburg and Moore, eds., Springer-Verlag, New York, pp. 269-315 (1994).

The term "diabody" refers to a small antibody fragment with two antigen-binding sites, which fragments comprise a variable heavy domain ($V_H$) connected to a variable light domain ($V_L$) in the same polypeptide chain. By using a linker that is too short to allow pairing between the two domains ($V_H$ and $V_L$) of the same chain, the domains are forced to pair with the complementary domains of another chain, thereby creating two antigen-binding sites. Diabodies are described more fully in, e.g., EP 0 404 097; WO 93/11161; and Hollinger et al., 1993, *Proc. Natl. Acad. Sci. USA* 90:6444-6448. The two antigen-binding sites can be the same or different.

An "isolated" binding agent is one that has been identified and separated and/or recovered from a component of its natural environment. Contaminant components of a natural environment are materials which would interfere with diagnostic or therapeutic uses for the binding agent, and may include enzymes, hormones, and other proteinaceous or nonproteinaceous solutes. In some embodiments, the binding agent will be purified (1) to greater than 95% by weight of the binding agent as determined by the Lowry method, or to greater than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. An isolated binding agent includes the binding agent in situ within recombinant cells since at least one component of the binding agent's natural environment will not be present. Ordinarily, however, the isolated binding agent will be prepared by at least one purification step.

A binding agent such as an antibody that is "directed to," "which binds" or that "specifically binds" an antigen of interest (i.e., a target antigen) is one capable of binding that antigen with sufficient affinity such that the binding agent is useful in targeting a cell expressing the antigen. Typically, the binding agent binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

An "antibody derivative" as used herein refers to an antibody, as defined above, that is modified by covalent attachment of a heterologous molecule such as, e.g., by attachment of a heterologous polypeptide, or by glycosylation, deglycosylation, acetylation or phosphorylation or other modification not normally associated with the antibody. In some embodiments, the heterologous molecule is not a therapeutic agent. In some embodiments, the heterologous molecule does not exhibit a cytostatic or cytotoxic effect by itself.

The term "effective regimen" refers to a course of treatment provided to a mammal, preferably a human, involving administering a therapeutically effective amount of a drug or drug composition effective to treat or prevent a disease or disorder in the mammal. Such a regimen involves administration of multiple doses of the drug or drug composition to a patient.

The term "therapeutically effective amount" refers to an amount of a drug or drug composition (e.g., an antibody or an antibody drug conjugate, alone or in combination with one or more therapeutic agents) effective to treat or prevent a disease or disorder in a mammal, preferably a human. In the case of cancer progression and/or cancer-associated cachexia, the therapeutically effective amount of the drug or drug composition may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit to some extent tumor growth; and/or relieve to some extent one or more of the symptoms, i.e., cachexia, associated with the cancer (e.g., tissue wasting, weight loss, fever night sweats or other symptom of cachexia). To the extent the drug or drug composition may prevent growth and/or kill existing cancer cells, it may be cytostatic and/or cytotoxic. For cancer progression therapy, efficacy can, for example, be measured by assessing the time to disease progression (TTP) and/or determining the response rate (RR). For cancer-associated cachexia therapy, efficacy can, for example, be measured by assessing weight loss and/or tissue wasting. In the case of treatment of patients in remission from a hematological malignancy (e.g., leukemia), the therapeutically effective amount of the drug may inhibit (i.e., slow to some extent and preferably stop) relapse (i.e., recurrence of the underlying hematological malignancy); or reduce the number of leukemic cells from the underlying hematological malignancy. To the extent the drug or drug composition may prevent growth and/or kill existing leukemic cells, it may be cytostatic and/or cytotoxic. For treatment of leukemia patients in remission, efficacy can, for example, be measured by the length of time in remission.

For treatment of an autoimmune or inflammatory disease, a therapeutically effective amount may alleviate one or more symptoms associated with the disease including decreasing or stabilizing pain, swelling, discomfort and/or tissue damage. For rheumatoid arthritis, efficacy and response may represent achieving the American College of Rheumatology ACR20 or ACR50 scores. In Crohn's disease, therapeutically effective doses may lower the Disease Activity Index (CDAI). This effect may be achieved by reducing circulating levels of pro-inflammatory cytokines and chemokines and/or decreasing the numbers of inflammatory infiltrating cells such as monocytes and macrophages. To the extent that the drug or drug composition may affect effector cell (monocyte, macrophage, etc.) function or activity, it may block or interfere with the activity of these cells (e.g., reduce cytokine production) or it may kill existing cells by inducing their apoptosis.

The term "therapeutic agent" as used herein refers to a chemotherapeutic agent, a radiotherapeutic agent, a therapeutic antibody, a small molecule (i.e., a chemical) drug, or a peptide drug that is administered to a mammal, preferably a human, in need thereof. The therapeutic agent can be administered separately from, or can be administered together with, a CD33 binding agent.

The term "chemotherapeutic agent" refers to a chemical compound useful in the treatment of cancer. Examples of chemotherapeutic agents include: alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); a dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalin and prodrugs thereof, novembichin, phenesterine, prednimustine, trofosfamide, and uracil mustard; nitrosureas such as carmustine, chlorozotocin, fotemustine, lomustine, nimustine, and ranimustine; bisphosphonates, such as clodronate; antibiotics such as the enediyne antibiotics (e.g., calicheamicin, especially calicheamicin gamma1I and calicheamicin omega1I (see, e.g., Agnew, 1994, *Chem. Intl. Ed. Engl.* 33:183-186) and anthracyclines such as annamycin, AD 32, aclarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, caminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine (also referred to as cytosoine arabinoside or Ara-C), dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; antifolate anti-neoplastic agents such as ALIMTA®, LY231514 pemetrexed, dihydrofolate reductase inhibitors such as methotrexate; anti-metabolites such as 5-fluorouracil (5-FU) and its prodrugs such as UFT, S-1 and capecitabine; and thymidylate synthase inhibitors and glycinamide ribonucleotide formyltranferase inhibitors such as raltitrexed (TOMUDEX™, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; a maytansinoid such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluoromethylomithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition of "chemotherapeutic agents" are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

The term "radiotherapeutic agent" refers to a chemical compound useful in the treatment of cancer that comprises a radioactive isotope (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu). The radiotherapeutic agent can be administered separately from, or can be bound (i.e., conjugated) to, a CD33 binding agent.

The term "therapeutic antibody" refers to an antibody, either alone (i.e., unconjugated) or bound (i.e., conjugated) to a cytotoxin, useful in the treatment of cancer, hematologic disease, and/or autoimmune or inflammatory disease. The antibody binds to a target antigen and provides a benefit to the patient such as, for example, to inhibit or prevent the function, and/or to cause destruction, of cancer or tumor cells expressing the antigen to which the antibody specifically binds, reduce pain, inflammation or the destruction of tissues in autoimmune or inflammatory disease settings.

The term "small molecule drug" as used herein refers to a chemical compound useful in the treatment of cancer or an autoimmune or inflammatory disease that is typically smaller than 1000 Daltons.

The term "peptide drug" as used herein refers to a chemical compound useful in the treatment of cancer or autoimmune or inflammatory disease that is primarily composed of amino acids linked by peptide bonds. Peptide drug is intended to include polypeptides with or without enzymatic activity. The amino acids can be naturally occur or non-naturally occurring amino acids.

The terms "cytotoxic agent" or "cytotoxin" refer to a substance that inhibits or prevents the function of cells and/or causes destruction of cells. The term is intended to include a peptide or a chemical (i.e., non-peptide-based) that has a direct toxic or destructive effect on living cells, usually those of a particular organ or cell type. The term is also intended include a "cyostatic agent" which refers to a substance that suppresses the growth and multiplication of a living cell. The term is intended to include chemotherapeutic agents and toxins such as small molecule toxins or enzymatically active (i.e., peptide-based) toxins of bacterial, fungal, plant or animal origin, including synthetic analogs and derivatives thereof. In some embodiments, the terms "cytotoxic agent" or "cytotoxin" exclude a radiotherapeutic agent.

The term "peptide cytotoxin" refers to a cytotoxic agent that is primarily composed of natural amino acids linked by peptide bonds. Exemplary peptide cytotoxins include saporin, ricin, a chlorotoxin, pseudomonas exotoxin, pseudomonas endotoxin or diphtheria toxin. The peptide cytotoxin can be administered separately from, or can be bound (i.e., conjugated) to, a CD33 binding agent.

The term "chemical cytotoxin" refers to a chemical compound that is typically smaller than 1000 Daltons. Exemplary chemical cytotoxins include a calicheamicin, doxorubicin, a camptothecin, a maytansinoid, daunorubicin, or other DNA binding agents. The chemical cytotoxin can be administered separately from, or can be bound (i.e., conjugated) to, a CD33 binding agent.

The term "conjugate" refers to a binding agent bound (i.e., conjugated) to a cytotoxic agent or cytotoxin. The cytotoxin can be a molecule that is not toxic to a living cell (or exhibits substantially reduced toxicity) until it is internalized by the cell. The cytotoxin can be chemically bound (i.e., conjugated) to the CD33 binding agent as described infra.

The terms "target polypeptide," "target protein" and "target antigen" refer to a protein, polypeptide, and in addition, in the case of a "target antigen," another molecule on the surface of, or associated with, a target cell, e.g., a non-malignant effector or accessory cell or leukemic cell.

Examples of a "patient" or "subject" include, but are not limited to, a human, or other mammals (e.g., rat, mouse, guinea pig, monkey, pig, goat, cow, horse, dog or cat). In an exemplary embodiment, the patient or subject is a human.

The terms "treat," "treating" and "treatment," unless otherwise indicated by context, refer to both therapeutic treatment and prophylactic or preventative measures, wherein the object is to prevent or slow down (i.e., lessen) an undesired physiological change or disorder, such as the development or spread of cancer. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. "Treatment" can also mean prolonging survival as compared to expected survival if not receiving treatment. Those in need of treatment include those already with the disease, condition or disorder, as well as those prone to have the disease, condition or disorder, or those in which the disease, condition or disorder is to be prevented.

In the context of cancer, the term "treating" includes any or all of: preventing growth of tumor cells, cancer cells, or of a tumor; preventing replication of tumor cells or cancer cells, lessening of overall tumor burden or decreasing the number of cancerous cells, preventing relapse or recurrence of the cancer, and ameliorating one or more symptoms associated with the disease. In the context of cancer-associated cachexia, the term "treating" includes any or all of: preventing or ameliorating at least one associated symptom, such as tissue wasting, fever, night sweats and/or weight loss. In the context of autoimmune or inflammatory disease, the term refers to alleviating or reducing symptoms associated with the disease including pain, discomfort, swelling, inflammation, pro-inflammatory cytokine or chemokine levels and/or destruction of tissues.

The term "relapse" refers to the recurrence or reoccurrence in a person of a medical condition or disease, such as cancer, that affected that person in the past.

The term "remission" refers to the state of absence of a detectable medical condition or disease in a patient previously known to have had the medical condition or disease, such as cancer.

A "bone marrow transplant" refers to the transplantation of hematopoietic stem cells (HSCs) into a patient with a disease of the blood or bone marrow, or certain types of cancer. HSCs or bone marrow cells that are infused intravenously repopulate the bone marrow and produce new blood cells. There are two major types of bone marrow transplantation: autologous and allogeneic.

The term "autologous" when referring to bone marrow transplantation refers to the isolation of HSCs typically from a large bone of a patient, storing the HSCs, treating the patient to destroy HSCs remaining in the body, and returning the patient's own HSCs to their body.

The term "allogeneic" when referring to bone marrow transplantation refers to the isolation of HSCs typically from a large bone of a person (donor) and transferring these HSCs to a patient (recipient) after their own HSCs have been destroyed. Allogeneic HSCs donors must have a tissue type that at least partially matches the recipient.

The term "cytokine" is a generic term for proteins released by any of the lymph cells that act on other cells as intercellular mediators and affect cellular activity and control inflammation. Cytokines are well-known in the art. Examples of such cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-$\alpha$ and -$\beta$; mullerian-inhibiting substance; mouse gonadotropin-associated peptide; inhibin; activin; vascular endothelial growth factor (VEGF); integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as, for example and not for limitation, IL-1, IL-1$\alpha$, IL-1$\beta$, IL-2, IL-3, IL-4, IL-5, IL-6, IL-7, IL-8, IL-9, IL-10, IL-11, IL-12; a tumor necrosis factor such as TNF-$\alpha$ or TNF-$\beta$; and other polypeptide factors including leukemia inhibitory factor (LIF) and kit ligand (KL). As used herein, when referring to a patient the term "cytokine" refers to on one or more of those produced by the patient.

The term "chemokine" is a generic term for any of the proteins that act on white blood cells and induce them to move and/or become activated to carry out their immune system functions. Chemokines are well-known in the art. Exemplary chemokines include, for example and not for limitation, TECK, ELC, BLC-1, CTACK, RANTES, fractalkine, exotaxin, eotaxin-2, Monocyte chemoattractant protein-1 (MCP-1), MCP-2, MCP-3, MCP-4, MDC, leukotactin, SDF-1$\beta$, lymphotactin, TARC, ITAC, ENA-70, ENA-78, IP-10, NAP-2, interleukin-8 (IL-8), HCC-1, MIP-1$\alpha$, MIP-1$\beta$, MIP-1$\delta$, I-309, GRO-$\alpha$, GRO-$\beta$, GRO-$\gamma$, MPIF-1, I-LINK, and GCP-2. As used herein, when referring to a patient the term "chemokine" refers to any of those produced by the patient.

The term "growth factors" is a generic term for a substance, typically a protein, produced by cells that stimulates them, or other cells, to grow, differentiate, proliferate and/or multiply. When produced in excessive amounts or expressed in inappropriate environments, such growth factors may be associated with abherant cell growth or proliferation, such as that seen in cancer. Growth factors that are associated with cancer are well-known in the art. Many growth factors that are associated with cancer are also described as cytokines, supra. Exemplary growth factors that are associated with cancer include, for example and not for limitation, tumor necrosis factor-$\alpha$ (TNF-$\alpha$) and vascular endothelial growth factor (VEGF). As used herein, when referring to a patient the term "growth factor" refers to one or more of those produced by the patient.

"Effector or accessory cells" as used herein include monocytes, macrophages, dendritic cells, and neutrophils. One type of effector or accessory cell macrophage is a tumor-associated macrophage (TAM). Effector or accessory cells produce and release a wide variety of cytokines, chemokines, and growth factors that may regulate the growth, proliferation and differentiation of tumor or cancer cells, or cells in the affected area(s) of a patient suffering from an autoimmune or inflammatory disease.

"Involved non-malignant effector cells" refers to effector or accessory cells that are associated with, or part of the pathology of a cancer or autoimmune or inflammatory disease, as applicable. TAMs are examples of involved non-malignant effector cells.

"Monocytes" are leukocytes (white blood cells that are produced in the bone marrow and help the body to defend itself against infectious disease and foreign matter) that are produced in the bone marrow from hematopoietic stem cell precursors, circulate in the blood, and move into tissues, where they mature into different types of macrophages at various locations in the body. Monocytes are responsible for phagocytosis (i.e., ingestion) of foreign substances in the body. Monocytes are also capable of killing infected cells via antibody-dependent cellular cytotoxicity (ADCC).

Macrophages are leukocytes that are differentiated from monocytes. When monocytes enter a tissue through the endothelium of a blood vessel, they undergo differentiation and become macrophages. Macrophages, which are attracted to damaged sites in the body, are phagocytic cells that engulf and digest cellular debris and pathogens.

"Dendritic cells" are immune cells that are present in small numbers in tissues that are in contact with the external environment (e.g., skin, lining of the nose, lungs, stomach, intestines). Upon activation, dendritic cells migrate to lymphoid tissues where they interact with B and T cells to initiate and modulate the immune response to foreign antigens. Some dendritic cells are derived from monocytes.

"Neutrophils" or "neutrophil granulocytes" are the most abundant type of white blood cell and are found only in the bloodstream. Neutrophils are phagocytes capable of ingesting microorganisms or particles. Unlike other effector or accessory cells, neutrophils can only execute one phagocytic event, expending all of their glucose reserves in a "respiratory burst."

"Macrophages" are present in the inflammatory infiltrate seen in both primary and secondary human tumors. These macrophages exhibit a distinct phenotype and are referred to as tumor-associated macrophages (TAMs). (See, e.g., Lewis and Pollard, 2006, *Cancer Res.* 66:605-612. TAMs respond to stimuli in the milieu of the tumor by releasing a wide variety of cytokines, chemokines, growth factors, enzymes, and other inflammatory mediators, which regulate tumor growth, angiogenesis, invasion and metastasis. In animal models, anti-tumor activity has been achieved by targeting TAM recruitment, survival, activation, polarization, effector signaling and extracellular matrix interactions.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the protein where, for example, the nucleic acid molecule is in a chromosomal location different from that of natural cells.

The expression "control sequences" refers to nucleic acid sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the nucleic acid sequences being linked are contiguous, and, in the case of a secretory leader, contiguous and in reading phase. However, enhancers do not have to be contiguous. Linking can be accomplished by ligation at convenient restriction sites. If such sites do not exist, the synthetic oligonucleotide adaptors or linkers can be used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

DETAILED DESCRIPTION

The invention relates to methods of treating patients with cancer or an autoimmune or inflammatory disease. The methods provide for the administration of CD33 binding agents (e.g., antibodies) and are useful for delaying cancer progression, reducing tumor burden, reducing cancer-associated cachexia, or other effects in a patient. The invention also relates to methods of preventing or delaying recurrence of leukemia and other cancer in a patient. The invention further relates to treating autoimmune or inflammatory diseases, such as by administering a CD33 binding agent to reduce inflammation and/or tissue damage associated with the autoimmune or inflammatory disease. The invention also provides pharmaceutical compositions comprising such CD33 binding agents for treating patients with cancer, or an autoimmune or inflammatory disease.

The present inventions are, in part, related to the discovery that patients with acute myeloid leukemia (AML) or myelodysplastic syndromes (MDS) feel symptomatically better, and in some cases exhibit tumor reduction, after a course of treatment with an antibody directed against CD33 administered at higher doses and intensities (i.e., higher dose, longer duration, higher number of treatments) than that used previously in the clinic to treat AML (see, e.g., Example 6). Such higher doses and intensities, previously thought to be supersaturating, provide therapeutic benefit to patients. The inventions are also related, in part, to the discovery that an antibody directed against CD33 can reduce the production of certain cytokines, chemokines and growth factors by human non-malignant effector or accessory cells (e.g., monocytes, macrophages, dendritic cells, and neutrophils) and by tumor cells (e.g., AML cells) in vitro. The inventions are also related, in part, to the discovery that an antibody directed against CD33 can reduce migration of macrophages. Using the invention as taught herein, complete response was observed in a fraction of AML patients treated. Partial response was also observed in a fraction of treated AML patients.

Without intending to be bound by any particular theory, blocking or interfering with the migration of monocytes and macrophages that are attracted to the tumor sites in the cancer patient or to the inflamed tissues in a patient with an autoimmune or inflammatory disease will be of great clinical benefit. By blocking the recruitment of these cells in a cancer patient, there will be reduced numbers of inflammatory infiltrating cells and a reduced production of pro-inflammatory cytokines and chemokines that enhance and promote the growth of tumors, which may lead to a reduced tumor burden and reduced tumor-associated cachetic symptoms. In a patient with an autoimmune or inflammatory disease, blocking the recruitment of monocytes and macrophages will lead to reduced numbers of inflammatory infiltrating cells in the affected area(s) and a reduced production of pro-inflammatory cytokines and chemokines that enhance and promote the destruction of tissues. The result would be reduced swelling, pain, and symptoms associated with the autoimmune or inflammatory disease.

For clarity of disclosure, and not by way of limitation, the detailed description is divided into the subsections which follow.

Methods of Treatment

In various aspects, methods of treating patients with cancer, or an autoimmune or inflammatory disease are provided. The methods include administering a CD33 binding agent (e.g., an antibody against CD33) that specifically binds to CD33, and are useful for, e.g., delaying cancer progression, reducing tumor burden, reducing cancer-associated cachexia, preventing or delaying the recurrence of leukemia or other cancer in a patient, or reducing inflammation and/or tissue damage associated with autoimmune or inflammatory diseases.

Treatment of Cancer

In one aspect, the CD33 binding agents are useful for treating cancer, such as by delaying progression of a cancer and/or reducing cancer-associated cachexia, or preventing or delaying recurrence of a hematological malignancy (e.g., leukemia), in a mammal, preferably a human patient. The CD33 binding agent can be administered alone or co-administered with another therapeutic agent. In some embodiments, the CD33 binding agent is co-administered with a standard of care chemotherapeutic(s). The CD33 binding agent can be administered in an unconjugated form (i.e., not conjugated to a cytotoxin) or as a conjugate. An illustrative, non-comprehensive list of non-hematological and hematological malignancies that can be treated is provided in Table I, infra.

In this subsection, a "patient" is a human or other mammal who is undergoing treatment for, or has been diagnosed as having, cancer. In some embodiments, the malignant cells (also called cancer or tumor cells) are CD33-negative cells (i.e., CD33-negative malignancy). As used herein, "CD33 negative" cells refers to cells that do not express CD33 on their cell surface, or that express CD33 at levels below that considered acceptable for therapy with CD33 antibodies.

In some embodiments, the CD33 binding agents are useful for delaying progression of a cancer and/or reducing cancer-associated cachexia in a patient by administering to the patient in need thereof an effective dosage of the CD33 binding agent. Without being bound to a particular mechanism, the CD33 binding agent binds to effector or accessory cells of the myeloid or monocytic lineages (e.g., monocytes, macrophages, dendritic cells, and neutrophils), thereby inhibiting or reducing the production of various cytokines, chemokines and growth factors from the effector or accessory cells and/or the tumor cells. These cytokines, chemokines and growth factors, which can promote the growth and proliferation of tumor cells and/or contribute to cancer cachexia, include, but are not limited to, interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α). The CD33 binding agents also can reduce the migration of macrophages to the site of the tumor cells. The CD33 binding agent can also reduce the migration of macrophages.

In some embodiments, administration of an effective dosage of a CD33 binding agent to a patient reduces the levels of at least one cytokine, chemokine or growth factor, which cytokine, chemokine or growth factor can promote the growth and proliferation of tumor cells, promote the migration of non-malignant effector cells, such as tumor associated macrophages (TAMS), to the vicinity of the tumor site and/or contribute to cancer cachexia. In specific embodiments, the cytokine, chemokine or growth factor is for example interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In some embodiments, CD33 binding agents can be used to treat anon-hematological malignancy (e.g., a CD33-negative malignancy). Suitable non-hematological malignancies are those in which the malignancy has been infiltrated by non-malignant effector cells, such as TAMs, and/or the growth of the malignancy is dependent upon cytokines, chemokines or growth factors produced by monocytes, macrophages or other CD33-positive cells.

In another embodiment, a method is provided for delaying progression of a cancer by administering to a patient an effective regimen of a CD33 binding agent that can specifically bind to CD33. As a result of administration of the CD33 binding agent, the progression of the cancer is delayed, such as by reducing the growth or proliferation of the tumor cells, decreasing metastasis, reducing the level of at least one cytokine, chemokine or growth factor, reducing non-malignant effector cells in the vicinity of the tumor cells, or the like. The cancer is optionally one that is refractory or resistant to chemotherapy, e.g., a multidrug-resistant cancer.

In another embodiment, a method is provided for reducing the tumor burden in a patient by administering to the patient an effective regimen of a CD33 binding agent that can specifically bind to CD33. As a result of administration of the CD33 binding agent, the tumor burden in the patient is arrested or reduced, such as by reducing the size or mass of the tumor, reducing the level of at least one cytokine, chemokine or growth factor, reducing non-malignant effector cells in the vicinity of the tumor cells, inhibiting the migration of macrophages in the vicinity of the tumor cells, reducing the number of non-malignant effector cells (e.g., TAMS or macrophages) in the tumor, or the like.

In another embodiment, a method is provided for reducing cancer-associated cachexia in a patient by administering to the patient an effective regimen of a CD33 binding agent that can specifically bind to CD33. As a result of administration of the CD33 binding agent, at least one symptom of cancer-associated cachexia in the patient is reduced, such as by reducing or arresting weight loss and/or tissue wasting.

In the various embodiments described in this section, the CD33 binding agent can be used to treat a CD33 negative or a CD33 positive cancer (i.e., a cancer comprised of cancer cells that over express CD33 on their cell surface, or that express CD33 at levels considered acceptable for therapy with CD33 antibodies). The CD33 binding agent also can be used to treat a cancer that does not overexpress CD33 on the non-malignant effector cells relative to normal tissue of the same type. The cancer can be, for example, a non-hematological malignancy or a hematological malignancy. In specific examples, the hematological malignancy can be CD33-positive or CD33-negative and can be, for example, acute lymphoid leukemia, chronic lymphoid leukemia, acute myeloid leukemia, chronic myelomonocytic leukemia, an erythrocytic leukemia, acute megakaryoblastic leukemia, multiple myeloma, histiocytic lymphoma, a myeloid sarcoma, a mast cell proliferative disorder or myelodysplastic syndrome (MDS). In some embodiments, the hematological malignancy is a CD33-positive malignancy, such as acute myeloid leukemia or myelodysplastic syndrome (MDS).

In the various embodiments described in this section, the CD33 binding agent can be an unconjugated anti-CD33 antibody. For example, the antibody can be a humanized or chimeric antibody, such as a chimeric or humanized M195 antibody. The antibody also can be another antibody, such as an antibody that competes with M195 antibody for specific binding to CD33. The antibody also can bind to the same epitope as M195 antibody.

In other embodiments, the CD33 binding agent can be bound (i.e., conjugated) to a cytotoxin. The cytotoxin can be, for example, a peptide toxin, such as saporin, ricin, chlorotoxin, pseudomonas exotoxin, pseudomonas endotoxin or diphtheria toxin. The cytotoxin also can be a chemical (i.e., non-peptide-based) toxin, such as a calicheamicin, doxorubicin, a camptothecin, daunorubicin, or other DNA binding agents. The cytotoxin also can be an auristatin, a maytansinoid, a dolastatin, or other microtubule blocking agents.

In some embodiments, the CD33 binding agent can be a protein that specifically binds to CD33 and induces phosphorylation of CD33 and recruitment of SHP-1 upon binding to CD33 on AML cells (e.g., HL-60 cells) in vitro. In some further embodiments, the CD33 binding agent does not cause recruitment of SHP-2 or Syk upon binding to CD33 on AML cells (e.g., HL-60 cells) in vitro.

A CD33 binding agent that is an anti-CD33 antibody can be administered to the patient intravenously at a dose of 1.5 mg/kg to about 12 mg/kg, 1.5 mg/kg to about 15 mg/kg, 2.5 mg/kg to about 12 mg/kg, or 2.5 mg/kg to about 12 mg/kg. A CD33 binding agent that is an anti-CD33 antibody fragment or other CD33 binding protein can be administered in a dosage equivalent to a dose of 1.5 mg/kg to about 12 mg/kg, 1.5 mg/kg to about 15 mg/kg, 2.5 mg/kg to about 12 mg/kg, or 2.5 mg/kg to about 12 mg/kg of intact antibody. The CD33 binding agent can be administered intravenously to the patient on a schedule that is, for example, daily, weekly, biweekly, tri-weekly (i.e., every three weeks) or monthly, or a combination thereof, to the patient. The CD33 binding agent can be administered for a period of at least one month, at least two months, at least three months, at least four months, at least five month, at least six months, or more, as needed. In some embodiments, a treatment phase (supra) of the CD33 binding agent is followed by a maintenance phase, in which doses of the CD33 binding agent are administered less frequently than during the treatment phase. For example, maintenance doses can be administered weekly, biweekly, tri-weekly (i.e., every three weeks) or monthly, for a period of 1-6 months. The dosages in the maintenance phase can be the same as the dosages in the treatment phase.

In some embodiments, the CD33 binding agent is administered at a dose of about 500-700 mg, sometimes about 550-650 mg, for example about 600 mg, regardless of body weight. The CD33 binding agent can be administered weekly for a period of 1 to 8, typically 1-4 weeks (e.g., one cycle). The CD33 binding agent can be administered weekly or biweekly in subsequent cycles.

In some embodiments, the methods further include monitoring the number of non-malignant effector or accessory cells displaying CD33, and/or the levels of one or more inflammatory cytokines, chemokines or growth factors, in the patient. Such monitoring can include monitoring non-malignant effector or accessory cells (e.g., monocytes, macrophages, dendritic cells and/or neutrophils) in the vicinity of the cancer cells. It can also include monitoring tumor-associated macrophages. The one or more pro-inflammatory cytokines, chemokines or growth factors that can be monitored include, but are not limited to, interleukin-1 (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α). The dosage of CD33 binding agent administered to the patient can be adjusted based on the monitoring.

In other embodiments, the methods further include monitoring the patient for the extent of cancer-associated cachexia responsive to the administration of the CD33 binding agent. The monitoring can include monitoring body weight, caloric intake, extent of appetite, extent of nausea, patient's sense of well-being, measurement of tumor burden, measurement of cytokine levels in blood, and the evaluation of muscle mass and fat mass. The dosage of CD33 binding agent administered to the patient can be adjusted based on the monitoring.

Co-Therapies for Treatment of Cancers

In another aspect, the CD33 binding agent is co-administered to the patient in combination with a therapeutic agent(s) effective against the cancer. In some embodiments, the cancer is CD33-positive. In other embodiments, the cancer is CD33-negative. The therapeutic agent can be, for example, a chemotherapeutic agent, a radiotherapeutic agent, a therapeutic antibody, a small molecule drug, or a peptide drug. In a specific embodiment, the therapeutic agent is a chemotherapeutic agent.

In some embodiments, the methods include administering to a patient in need thereof an effective amount of a CD33 binding agent and a therapeutic agent to treat or prevent cancer. In one embodiment, the therapeutic agent is that with which treatment of the cancer has not been found to be refractory. In another embodiment, the therapeutic agent is that with which the treatment of cancer has been found to be refractory, e.g., multidrug-resistant cancers. The CD33 binding agent can be administered to a patient who has also undergone surgery as treatment for the cancer. In one embodiment, the patient has been or will be treated with radiation therapy.

In a specific embodiment, the CD33 binding agent is administered concurrently with the therapeutic agent or with radiation therapy. In another specific embodiment, the therapeutic agent or radiation therapy is administered prior to administration of the CD33 binding agent. In yet another specific embodiment, the therapeutic agent or radiation therapy is administered subsequent to administration of the CD33 binding agent. In some embodiments, the therapeutic agent or radiation therapy is administered at least one hour, five hours, 12 hours, a day, a week, a month or several months (e.g., up to three months), prior or subsequent to administration of the CD33 binding agent. A therapeutic agent also can be administered over a series of sessions.

As discussed above, the therapeutic agent can be, for example, a chemotherapeutic agent, a radiotherapeutic agent, a therapeutic antibody, a small molecule drug, or a peptide drug. In an embodiment, the one or more therapeutic agents is a chemotherapeutic agent. For example, the chemotherapeutic agent can be VELCADE® (Bortezomib) or REVLIMID® (lenalidomide), cytosine arabinoside (cytarabine; Ara-C), VIDAZA® (azacitidine), daunorubicin, idarubicin, 6-thioguanine, or mithramycin.

A CD33 binding agent that is an anti-CD33 antibody can be administered to the patient intravenously at a dose of 1.5 mg/kg to about 12 mg/kg, 1.5 mg/kg to about 15 mg/kg, 2.5 mg/kg to about 12 mg/kg, or 2.5 mg/kg to about 12 mg/kg. A CD33 binding agent that is an anti-CD33 antibody fragment or other CD33 binding protein can be administered in a dosage equivalent to 1.5 mg/kg to about 12 mg/kg, 1.5 mg/kg to about 15 mg/kg, 2.5 mg/kg to about 12 mg/kg, or 2.5 mg/kg to about 12 mg/kg of intact antibody.

In some embodiments, the CD33 binding agent is administered at a dose of about 500-700 mg, sometimes about 550-650 mg, for example about 600 mg, regardless of body weight. The CD33 binding agent can be administered weekly for a period of 1 to 8, typically 1-4 weeks (e.g., one cycle). The CD33 binding agent can be administered weekly or biweekly in subsequent cycles.

In a specific embodiment, the CD33 binding agent is co-administered with a low dose cytosine arabinoside regimen to a patient having a CD33-positive hematological malignancy, such as AML. The dosage regimen can be as follows: the cytarabine regimen comprises cycles of 10-30 milligrams (typically about 20 milligrams) of cytarabine twice daily by subcutaneous injection daily on days 1-10. The dosing regimen cycle is repeated every 28 to 42 days, typically every four weeks. Typically, at least 2, 3, 4 or more cycles of cytarabine are administered. Additional cycles can be administered, as needed.

The CD33 binding agent dosing regimen comprises cycles of daily, every other day, weekly, bi-weekly, tri-weekly or monthly administrations of the agent. The doses can be administered in a dosage equivalent to 1.5 mg/kg to about 12 mg/kg, 1.5 mg/kg to about 15 mg/kg, 2.5 mg/kg to about 12 mg/kg, or 2.5 mg/kg to about 12 mg/kg of intact antibody. Cycles of the CD33 binding agent are typically administered for at least one month, at least two months, at least three months, at least four months, at least five months, at least six months or more, as needed. In some embodiments, a treatment phase (supra) of the CD33 binding agent is followed by a maintenance phase, in which doses of the CD33 binding agent are administered less frequently than during the treatment phase. For example, maintenance doses can be administered weekly, biweekly, tri-weekly (i.e., every three weeks) or monthly, for a period of 1-6 months. The dosages in the maintenance phase can be the same as the dosages in the treatment phase.

In some embodiments, the CD33 binding agent is administered at a dose of about 500-700 mg, sometimes about 550-650 mg, for example about 600 mg, regardless of body weight. The CD33 binding agent can be administered weekly for a period of 1 to 8, typically 1-4 weeks (e.g., one cycle). The CD33 binding agent can be administered weekly or biweekly in subsequent cycles.

In some embodiments, the patient is elderly, at least 50 years of age, or at least 60 years of age, or at least 65 years of age, or at least 70 years of age. In other embodiments, the patient is less than 60 or 65 years of age.

In some embodiments, wherein the patient is elderly (e.g., at least 50 years of age, or at least 60 years of age, or at least 65 years of age, or at least 70 years of age), the CD33 binding agent/low dose cytarabine dosing regimen is chronically administered to the patient to extend the life of the patient. In such an embodiment, the patient treated with the CD33 binding agent/low dose cytarabine dosing regimen has a longer life expectancy, as compared with a patient treated with cytarabine alone. For example, it is contemplated the patient's average life expectancy can be extended by at least one, at least two, at least three or at least four months, relative to the average life expectancy of a patient treated with the low dose cytarabine regimen alone.

In a specific embodiment, the cytarabine regimen comprises cycles of 20 milligrams of cytarabine twice daily by subcutaneous injection daily on days 1-10. The dosing regimen cycle is repeated four weeks. The CD33 binding agent is administered weekly during the first cycle and bimonthly in subsequent cycles (e.g., up to 11 additional cycles). Additional cycles can be administered, as needed.

A patient treated according to these methods can have, for example, a CD33 positive acute lymphoid leukemia, chronic lymphoid leukemia, acute myeloid leukemia, chronic myelomonocytic leukemia, an erythrocytic leukemia, acute megakaryoblastic leukemia, multiple myeloma, histiocytic lymphoma, a myeloid sarcoma, a mast cell proliferative disorder or myelodysplastic syndrome. In a specific embodiment, the patent has AML. For example, the patient can have untreated or newly-diagnosed AML. Alternatively, the patient can have previously treated AML. The patient also can have refractory AML.

In some embodiments, the CD33 binding agent is an unconjugated anti-CD33 antibody. The antibody can be, for example, a humanized or chimeric M195 antibody. Alternatively, the antibody can compete with M195 antibody for specific binding to CD33. The antibody also can bind to the same epitope as M195 antibody.

In other embodiments, the CD33 binding agent can be bound (i.e., conjugated) to a cytotoxin. The cytotoxin can be a peptide toxin, such as saporin, ricin, chlorotoxin, pseudomonas exotoxin, pseudomonas endotoxin, and diphtheria toxin. The cytotoxin also can be a chemical (i.e., non-peptide-based) toxin selected from the group consisting of a calicheamicin, doxorubicin, a camptothecin, daunorubicin, and other DNA binding agents. The cytotoxin also can be an auristatin, a maytansinoid, a dolastatin, or other microtubule blocking agents.

The CD33 binding agent also can be a protein that specifically binds to CD33 and induces phosphorylation of CD33 and recruitment of SHP-1 upon binding to CD33 on AML cells (e.g., HL-60 cells). In some further embodiments, the CD33 binding agent does not cause recruitment of SHP-2 or Syk upon binding to CD33 on AML cells (e.g., HL-60 cells) in vitro.

Treatment of a Hematological Malignancy in Remission

In another aspect, methods are provided of preventing or delaying recurrence of a hematological malignancy (e.g., leukemia) in a patient by administering to the patient in remission from the hematological malignancy an effective dosage of a CD33 binding agent, resulting in preventing or delaying recurrence of the underlying hematological malignancy. The CD33 binding agent specifically binds to CD33 on the surface of the hematological malignancy (i.e., leukemic cell) and/or to non-malignant effector cells.

In this disclosure, a "patient" is typically a human who is undergoing treatment for, or has been diagnosed as having, hematological malignancy. In some embodiments, the hematological malignancy is a CD33-positive hematological malignancy. Hematological malignancies include, but are not limited to, leukemias (e.g., acute lymphoblastic leukemia (ALL), acute myelogenous leukemia (AML), chronic lymphocytic leukemia (CLL), chronic myelogenous leukemia (CML), chronic myelomonocytic leukemia, hairy cell leukemia), lymphomas (e.g., Hodgkin's disease, non-Hodgkin's lymphoma), and multiple myeloma. Related blood disorders include, but are not limited to, myelodysplastic syndrome (MDS), myelofibrosis, myeloproliferative disease (e.g., polycythemia vera (PV, PCV or PRV), essential thrombocytosis (ET)), and amyloid due to light-chain disease.

The term "CD33-positive hematological malignancy" refers to a hematological malignancy characterized by the expression of CD33 on the surface of the malignant cells. CD33-positive hematological malignancies include, but are not limited to, acute myeloid leukemia (AML), chronic myeloid leukemia (CML), chronic myelomonocytic leukemia, thrombolytic leukemia, a myelodysplastic syndrome, a myeloproliferative disorder, refractory anemia, a preleukemia syndrome, a lymphoid leukemia, or an undifferentiated leukemia.

The term "CD33-negative hematological malignancy" refers to a hematological malignancy characterized by the lack of expression of CD33 on the surface of the malignant cells. CD33-negative hematological malignancies include, but are not limited to, CD33-negative acute lymphoid leukemia (ALL), CD33-negative chronic lymphoid leukemia (CLL), erythrocytic leukemia and megakaryoblastic leukemia.

In some embodiments, the methods include administering to a patient in remission from a CD33 positive hematological malignancy an effective regimen of a CD33 binding agent, whereby the recurrence of the hematological malignancy is prevented or delayed. In some embodiments, the patient lacks detectable cells of the hematological malignancy. As used herein, a "lack of detectable cells" is determined by standard diagnostic or prognostic methods. A patient in remission from AML typically exhibits resolution of abnormal clinical features, return to normal blood counts and normal hematopoiesis in the bone marrow with <5% blast cells, a neutrophil count of >1,000-1,500, a platelet count of >100,000, and disappearance of the leukemic clone. See, e.g., The Merck Manual, Sec. 11, Ch. 138 (17$^{th}$ ed. 1997); Estey, 2001, Cancer 92(5):1059-1073.

The CD33 binding agent can be, for example, an antibody that specifically binds to CD33 and the hematological malignancy can be acute myeloid leukemia (AML), chronic myeloid leukemia (CML), chronic myelomonocytic leukemia, thymoid leukemia, a myelodysplastic syndrome, a myeloproliferative disorder, refractory anemia, a preleukemia syndrome, a lymphoid leukemia, or an undifferentiated leukemia.

The CD33 binding agent can be an unconjugated antibody. For example, the antibody can be a humanized or chimeric M195 antibody. Alternatively, the antibody can compete with M195 antibody for specific binding to CD33. The CD33 binding agent also can be bound to a cytotoxin. The cytotoxin can be, for example, a peptide toxin, such as saporin, ricin, chlorotoxin, pseudomonas exotoxin, pseudomonas endotoxin or diphtheria toxin. The cytotoxin also can be a chemical (i.e., non-peptide-based) toxin such as a calicheamicin, doxorubicin, a camptothecin, daunorubicin, and other DNA binding agents. The cytotoxin also can be an auristatin, a maytansinoid, a dolastatin, and other microtubule blocking agents.

The CD33 binding agent also can be a protein that specifically binds to CD33 and induces phosphorylation of CD33 and recruitment of SHP-1 upon binding to CD33 on AML cells (e.g., HL-60 cells). In some further embodiments, the CD33 binding agent does not cause recruitment of SHP-2 or Syk upon binding to CD33 on AML cells (e.g., HL-60 cells) in vitro.

A CD33 binding agent that is an anti-CD33 antibody can be administered to the patient intravenously at a dose of 1.5 mg/kg to about 12 mg/kg, 1.5 mg/kg to about 15 mg/kg, 2.5 mg/kg to about 12 mg/kg, or 2.5 mg/kg to about 12 mg/kg. A CD33 binding agent that is an anti-CD33 antibody fragment or other CD33 binding protein can be administered in a dosage equivalent to 1.5 mg/kg to about 12 mg/kg, 1.5 mg/kg to about 15 mg/kg, 2.5 mg/kg to about 12 mg/kg, or 2.5 mg/kg to about 12 mg/kg of intact antibody. The CD33 binding agent can be administered intravenously to the patient on a schedule that is, for example, daily, weekly, biweekly, tri-weekly or monthly to the patient. In a typically embodiment, the CD33 binding agent is administered for at least two months, at least three months, at least four months, at least six months, at least eight months or at least 10 months after the patient is in remission. In some embodiments, the CD33 binding agent is administered from 1-4 times per month for at least six months. In some embodiments, the CD33 binding agent is chronically administered from 1-4 times per month to maintain the patient in remission.

In some embodiments, the CD33 binding agent is administered at a dose of about 500-700 mg, sometimes about 550-650 mg, for example about 600 mg, regardless of body weight. The CD33 binding agent can be administered weekly for a period of 1 to 8, typically 1-4 weeks (e.g., one cycle). The CD33 binding agent can be administered weekly or biweekly in subsequent cycles.

In some embodiments, the patient in remission from the hematological malignancy has not undergone a bone marrow transplant. In other embodiments, the patient in remission from the hematological malignancy has undergone a bone marrow transplant. The bone marrow transplant can be either an autologous or an allogeneic bone marrow transplant.

TABLE I

List of Cancers That Can Be Treated With CD33 Binding Agents

Solid tumors, including, but not limited to:
    fibrosarcoma
    myxosarcoma
    liposarcoma
    chondrosarcoma
    osteogenic sarcoma
    chordoma TABLE I-continued List of Cancers That Can Be Treated With CD33 Binding Agents angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon cancer
    rectal cancer
    colorectal cancer
    kidney cancer
    pancreatic cancer
    bone cancer
    breast cancer
    ovarian cancer
    prostate cancer
    penile carcinoma
    esophogeal cancer
    gastric cancer
    gastrointestinal cancer
    stomach cancer
    peritoneal cancer
    hepatic carcinoma
    hepatocellular cancer
    liver cancer
    oral cancer
    nasal cancer
    throat cancer
    squamous cell carcinoma (e.g., epithelial)
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    uterine cancer
    endometrial or uterine carcinoma
    vulval cancer
    testicular cancer
    bladder carcinoma
    lung cancer, including small cell lung carcinoma, non-small cell lung cancer, adenocarcinoma of the lung and squamous carcinoma of the lung
    epithelial carcinoma
    glioma
    glioblastoma
    glioblastoma multiforme
    astrocytoma
    medulloblastoma
    craniopharyngioma
    ependymoma
    pinealoma
    hemangioblastoma
    acoustic neuroma
    oligodendroglioma
    meningioma
    skin cancer
    melanoma
    neuroblastoma
    retinoblastoma
    salivary gland carcinoma
    thyroid cancer
    head cancer
    neck cancer TABLE I-continued List of Cancers That Can Be Treated With CD33 Binding Agents anal cancer
Blood-borne cancers, including, but not limited to:
    acute lymphoblastic leukemia "ALL"
    acute lymphoblastic B-cell leukemia
    acute lymphoblastic T-cell leukemia
    acute myeloblastic leukemia "AML"
    acute promyelocytic leukemia "APL"
    acute monoblastic leukemia
    acute erythroleukemic leukemia
    acute megakaryoblastic leukemia
    acute myelomonocytic leukemia
    acute nonlymphocytic leukemia
    acute undifferentiated leukemia
    chronic myelocytic leukemia "CML"
    chronic lymphocytic leukemia "CLL"
    hairy cell leukemia
    multiple myeloma
    myelodysplastic syndromes "MDS"
Acute and chronic leukemias:
    lymphoblastic
    myelogenous
    lymphocytic
    myelocytic leukemias
Lymphomas:
    Hodgkin's disease
    non-Hodgkin's Lymphoma
Multiple myeloma
Waldenström's macroglobulinemia
Heavy chain disease
Polycythemia vera Treatment of Autoimmune and Inflammatory Disease The CD33 binding agents are useful to treat autoimmune or inflammatory disease in a mammal, preferably a human patient. As used herein, "autoimmune or inflammatory disease" is interchangeable with "autoimmune or inflammatory disorder" or "autoimmune or inflammatory condition." In this aspect, the autoimmune or inflammatory disease is one associated with infiltrates that include monocytes and macrophages that are CD33-positive. As discussed above, and without being bound to a particular mechanism, the CD33 binding agents are believed to bind to effector or accessory cells of the myeloid or monocytic lineages (e.g., monocytes, macrophages, dendritic cells, and neutrophils), thereby inhibiting or reducing the production of various cytokines, chemokines or growth factors from the effector or accessory cells. The cytokines, chemokines or growth factors, which can promote inflammation, include, but are not limited to, interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In some embodiments, administration of an effective dosage of the CD33 binding agent to a patient reduces the level of at least one cytokine, chemokine or growth factor in the blood and/or decreases the levels of inflammatory infiltrating cells in the affected area(s) of patients with the autoimmune or inflammatory disease. In specific embodiments, the cytokine, chemokine or growth factor is for example interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α). In other embodiments, administration of the CD33 binding agent reduces migration of macrophages to the affected areas of the patient. In other embodiments, administration of the CD33 binding agent reduces macrophages at the affected area(s) of the patient.

The CD33 binding agent can be, for example, an unconjugated or conjugated antibody. In some embodiments, the anti-CD33 antibody can be a humanized or chimeric M195 antibody. In some embodiments, the anti-CD33 antibody can be an antibody that competes with M195 antibody for specific binding to CD33.

The CD33 binding agent also can be a protein that specifically binds to CD33 and induces phosphorylation of CD33 and recruitment of SHP-1 upon binding to CD33 on AML cells (e.g., HL-60 cells) in vitro. In some further embodiments, the CD33 binding agent does not cause recruitment of SHP-2 or Syk upon binding to CD33 on AML cells (e.g., HL-60 cells) in vitro.

A CD33 binding agent that is an anti-CD33 antibody can be administered to the patient intravenously at a dose of 1.5 mg/kg to about 12 mg/kg, 1.5 mg/kg to about 15 mg/kg, 2.5 mg/kg to about 12 mg/kg, or 2.5 mg/kg to about 12 mg/kg. A CD33 binding agent that is an anti-CD33 antibody fragment or other CD33 binding protein can be administered in a dosage equivalent to 1.5 mg/kg to about 12 mg/kg, 1.5 mg/kg to about 15 mg/kg, 2.5 mg/kg to about 12 mg/kg, or 2.5 mg/kg to about 12 mg/kg of intact antibody. The CD33 binding agent can be administered intravenously to the patient on a schedule that is, for example, daily, weekly, biweekly tri-weekly or monthly to the patient. The CD33 binding agent can be administered for a period of at least one month, at least two months, at least three months, at least four months, at least five month, at least six months, or more, as needed. In some embodiments, a treatment phase (supra) of the CD33 binding agent is followed by a maintenance phase, in which doses of the CD33 binding agent are administered less frequently than during the treatment phase. For example, maintenance doses can be administered weekly, biweekly, tri-weekly (i.e., every three weeks) or monthly, for a period of 1-6 months. The dosages in the maintenance phase can be the same as the dosages in the treatment phase.

In some embodiments, the CD33 binding agent is administered at a dose of about 500-700 mg, sometimes about 550-650 mg, for example about 600 mg, regardless of body weight. The CD33 binding agent can be administered weekly for a period of 1 to 8, typically 1-4 weeks (e.g., one cycle). The CD33 binding agent can be administered weekly or biweekly in subsequent cycles.

In one embodiment, the CD33 binding agent is used to treat a patient with an autoimmune or inflammatory disease such as inflammatory bowel disease (IBD), psoriasis, atopic dermatitis, psoriatic arthritis, or rheumatoid arthritis.

A more comprehensive list of autoimmune or inflammatory diseases includes, but is not limited to, arthritis (rheumatoid arthritis, juvenile rheumatoid arthritis, osteoarthritis, psoriatic arthritis, and ankylosing spondylitis), psoriasis, dermatitis including atopic dermatitis; chronic idiopathic urticaria, including chronic autoimmune urticaria, polymyositis/dermatomyositis, toxic epidermal necrolysis, systemic scleroderma and sclerosis, responses associated with inflammatory bowel disease (IBD) (Crohn's disease, ulcerative colitis), and IBD with co-segregate of pyoderma gangrenosum, erythema nodosum, primary sclerosing cholangitis, and/or episcleritis, respiratory distress syndrome, including adult respiratory distress syndrome (ARDS), meningitis, IgE-mediated diseases such as anaphylaxis and allergic rhinitis, encephalitis such as Rasmussen's encephalitis, uveitis, colitis such as microscopic colitis and collagenous colitis, glomerulonephritis (GN) such as membranous GN, idiopathic membranous GN, membranous proliferative GN (MPGN), including Type I and Type II, and rapidly progressive GN, allergic conditions, eczema, asthma, conditions involving infiltration of T cells and chronic inflammatory responses, atherosclerosis, autoimmune myocarditis, leukocyte adhesion deficiency, systemic lupus erythematosus (SLE) such as cutaneous SLE, lupus (including nephritis, cerebritis, pediatric, non-renal, discoid, alopecia), juvenile onset diabetes, multiple sclerosis (MS) such as spino-optical MS, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including Large Vessel vasculitis (including Polymyalgia Rheumatica and Giant Cell (Takayasu's) Arteritis), Medium Vessel vasculitis (including Kawasaki's Disease and Polyarteritis Nodosa), CNS vasculitis, and ANCA-associated vasculitis, such as Churg-Strauss vasculitis or syndrome (CSS)), aplastic anemia, Coombs positive anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome, myasthenia gravis, antigen-antibody complex mediated diseases, anti-glomerular basement membrane disease, anti-phospholipid antibody syndrome, allergic neuritis, Bechet disease, Castleman's syndrome, Goodpasture's Syndrome, Lambert-Eaton Myasthenic Syndrome, Reynaud's syndrome, Sjorgen's syndrome, Stevens-Johnson syndrome, solid organ transplant rejection (including pre-treatment for high panel reactive antibody titers, IgA deposit in tissues, and rejection arising from renal transplantation, liver transplantation, intestinal transplantation, cardiac transplantation, etc.), graft versus host disease (GVHD), pemphigoid bullous, pemphigus (including vulgaris, foliaceus, and pemphigus mucus-membrane pemphigoid), autoimmune polyendocrinopathies, Reiter's disease, stiff-man syndrome, immune complex nephritis, IgM polyneuropathies or IgM mediated neuropathy, idiopathic thrombocytopenic purpura (ITP), thrombotic thrombocytopenic purpura (TTP), thrombocytopenia (as developed by myocardial infarction patients, for example), including autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM), including pediatric IDDM, and Sheehan's syndrome; autoimmune hepatitis, Lymphoid interstitial pneumonitis (HIV), bronchiolitis obliterans (non-transplant) vs NSIP, Guillain-Barré Syndrome, Berger's Disease (IgA nephropathy), primary biliary cirrhosis, celiac sprue (gluten enteropathy), refractory sprue with co-segregate dermatitis herpetiformis, cryoglobulinemia, amylotrophic lateral sclerosis (ALS; Lou Gehrig's disease), coronary artery disease, autoimmune inner ear disease (AIED), autoimmune hearing loss, opsoclonus myoclonus syndrome (OMS), polychondritis such as refractory polychondritis, pulmonary alveolar proteinosis, amyloidosis, giant cell hepatitis, scleritis, monoclonal gammopathy of uncertain/unknown significance (MGUS), peripheral neuropathy, paraneoplastic syndrome, channelopathies such as epilepsy, migraine, arrhythmia, muscular disorders, deafness, blindness, periodic paralysis, and channelopathies of the CNS; autism, inflammatory myopathy, and focal segmental glomerulosclerosis (FSGS).

The patient can be monitored for symptoms associated with the disease including, but not limited to, pain, swelling, discomfort, diarrhea, anemia, weight loss, joint deformity, blood levels of cytokines, and/or inflammatory infiltrating cells in the affected area(s). The dosage of CD33 binding agent administered to the patient can be adjusted based on the monitoring.

In a specific embodiment, the CD33 binding agent reduces cytokine and chemokine levels in the blood and/or the levels of inflammatory infiltrating cells in the affected area(s) of patients with autoimmune or inflammatory disease. The pro-inflammatory cytokines or chemokines can be for instance interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10 and/or macrophage inflammatory protein 1α (MIP1α).

In some embodiments, the CD33 binding agent is administered alone. In some embodiments, the CD33 binding agent is co-administered with a therapeutic agent. In some embodiments, the CD33 binding agent is co-administered with a standard of care chemotherapeutic(s). For example, the CD33 binding agent can be administered to the patient in combination with one or more therapeutic agents effective for the treatment of autoimmune or inflammatory disease. The one or more therapeutic agents can be, for example, a pain reliever such as aspirin or TYLENOL® (Acetaminophen); a nonsteroidal anti-inflammatory drug (NSAID) such as ibuprofen; a corticosteroid such as cortisone or prednisone; a therapeutic antibody such as etanercept (ENBREL®), infliximab (REMICADE®) or anakinra (KINERET®); an immunosuppressive agent such as methotrexate, cyclophosphamide, or cyclosporine; an antibiotics such as FLAGYL® (metronidazole) or CIPRO® (Ciprofloxacin), or small molecule compounds such as sulfasalazine (AZULFIDINE) or hydroxychloroquine (PLAQUENIL).

Monitoring Effector or Accessory Cells and Inflammatory Cytokines, Chemokines or Growth Factors Methods of measuring the number of non-malignant effector or accessory cells in a body fluid or tissue sample from a patient are well-known in the art. Example 9 describes a method of identifying and quantifying CD33-positive cells from blood or bone marrow from a patient, and Example 4 describes a method of identifying effector or accessory cells in a tissue sample from a patient. Examples 3 and 9 describe methods of identifying and quantifying effector or accessory cells.

Methods of measuring the levels of inflammatory cytokines, chemokines or growth factors in a body fluid or tissue sample from a patient are well known in the art. Example 8 describes a method to quantify the levels of a wide variety of inflammatory cytokines, chemokines and growth factors in a body fluid from a patient. Example 3 describes methods of quantifying the levels of an illustrative set of inflammatory cytokines, chemokines and growth factors in a sample.

Blood counts, such as neutrophil counts and platelet counts can be determined by standard methods. As a measure of residual disease, APL fusion protein levels can be measured, such as by RT-PCR (see, e.g., Jurcic et al., 2000, *Clin. Cancer Res.* 6:372-380).

CD33 Binding Agents

The CD33 binding agents specifically bind to a receptor, CD33, associated with a given target cell population. CD33 is a member of the sialoadhesion family that is expressed on cells of the hematopoietic lineage, including myeloid precursors, monocytes, macrophages, dendritic cells, mast cells, T cells, and NK cells. CD33 is also expressed on tumor cells associated with myeloproliferative or mast cell proliferative diseases, including acute myeloid leukemia and on leukemic stem cells. Antibodies targeting CD33 and their uses have been generally described (see, e.g., Pierelli et al., 1993, *Br. J. Haematol.* 84:24-30; Matutes et al., 1985, *Hematol. Oncol.* 3:179-186; Taussig et al., 2005, *Blood* 106:4086-4092; Florian et al., 2006, *Leuk. & Lymph.* 47:207-222).

In some embodiments, the CD33 binding agent is an antibody (e.g., a monoclonal antibody). Useful monoclonal antibodies can be homogeneous populations of antibodies to a CD33 (e.g., the extracellular domain of human CD33). A monoclonal antibody (mAb) can be prepared by using any technique known in the art. These include, but are not limited to, the hybridoma technique originally described by Köhler and Milstein (1975, *Nature* 256:495-497), the human B cell hybridoma technique (Kozbor et al., 1983, *Immunology Today* 4:72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing a monoclonal antibody may be cultivated in vitro or in vivo.

Useful monoclonal antibodies include, but are not limited to, human monoclonal antibodies, humanized monoclonal antibodies, chimeric monoclonal antibodies and functionally active antibody fragments of any of these.

Useful CD33 antibodies include antibodies that can achieve a therapeutic effect by various mechanisms known in the art, such as antibody-dependent cell-mediated cytoxicity (ADCC), anti-dependent cell phagocytosis (ADCP) and/or complement dependent cytotoxicity (CDC). For example the antibody can mediate ADCC by interacting with various immune cells such as monocytes, macrophages, dendritic cells, mast cells, T cells, and NK cells.

Recombinant antibodies, such as chimeric and humanized monoclonal antibodies, comprising both human and non-human portions, which can be made using standard recombinant DNA techniques. (See, e.g., Cabilly et al., U.S. Pat. No. 4,816,567; and Boss et al., U.S. Pat. No. 4,816,397; both of which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0184187; European Patent Publication No. 0171496; European Patent Publication No. 0173494; International Publication No. WO 86/01533; U.S. Pat. No. 4,816,567; European Patent Publication No. 012023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Human monoclonal antibodies may be made by any of numerous techniques known in the art (see, e.g., Teng et al., 1983, *Proc. Natl. Acad. Sci. USA*. 80:7308-7312; Kozbor et al., 1983, *Immunology Today* 4:72-79; Olsson et al., 1982, *Meth. Enzymol.* 92:3-16; and U.S. Pat. Nos. 5,939,598 and 5,770,429).

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a CD33 polypeptide. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see, e.g., Lonberg and Huszar (1995, *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661,016; and 5,545,806; each of which is incorporated herein by reference in its entirety. Other human antibodies can be obtained commercially from, for example, Medarex (Princeton, N.J.).

Completely human antibodies that recognize a selected epitope also can be generated using a technique referred to as "guided selection." In this approach a selected non-human monoclonal antibody, e.g., a mouse antibody, is used to guide the selection of a completely human antibody recognizing the same epitope. (See, e.g., Jespers et al., 1994, *Biotechnology* 12:899-903.) Human antibodies also can be produced using various techniques known in the art, including phage display libraries (see, e.g., Hoogenboom and Winter, 1991, *J. Mol. Biol.* 227:381; Marks et al., 1991, *J. Mol. Biol.* 222:581; Quan and Carter, 2002, *The rise of monoclonal antibodies as therapeutics*, In Anti-IgE and Allergic Disease, Jardieu and Fick Jr., eds., Marcel Dekker, New York, N.Y., Chapter 20, pp. 427-469).

In some embodiments, the antibody is monospecific. The antibody also can be a multispecific, such as a bispecific, antibody. Methods for making bispecific antibodies are known in the art. Traditional production of full-length bispecific antibodies is based on the coexpression of two immunoglobulin heavy chain-light chain pairs, where the two chains have different specificities (see, e.g., Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Similar procedures are disclosed in International Publication No. WO 93/08829, and in Traunecker et al., 1991, *EMBO J.* 10:3655-3659.

According to a different approach, antibody variable domains with the desired binding specificities (antibody-antigen combining sites) are fused to immunoglobulin constant domain sequences. The fusion typically is with an immunoglobulin heavy chain constant region, comprising at least part of the hinge, $C_H2$, and $C_H3$ domains. It is preferred to have the first heavy-chain constant region ($C_H1$), containing the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for flexibility in adjusting the mutual proportions of the three polypeptide fragments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

For example, the bispecific antibodies can have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (International Publication No. WO 94/04690; which is incorporated herein by reference in its entirety).

For further details for generating bispecific antibodies see, for example, Suresh et al., 1996, *Methods in Enzymology* 121:210; Rodrigues et al., 1993, *J. Immunology* 151:6954-6961; Carter et al., 1992, *Bio/Technology* 10: 163-167; Carter et al., 1995, *J. Hematotherapy* 4:463-470; Merchant et al., 1998, *Nature Biotechnology* 16:677-681. Using such techniques, bispecific antibodies can be prepared for use in the treatment or prevention of disease as defined herein.

Bifunctional antibodies are also described in European Patent Publication No. 0105360. As disclosed in this reference, hybrid or bifunctional antibodies can be derived biologically, e.g., by cell fusion techniques, or chemically, especially with cross-linking agents or disulfide-bridge forming reagents, and may comprise whole antibodies or fragments thereof. Methods for obtaining such hybrid antibodies are disclosed, for example, in International Publication WO 83/03679, and European Patent Publication No. 0217577, both of which are incorporated herein by reference.

The antibody also can be a functionally active fragment or derivative that specifically binds to CD33. In this regard, "functionally active" means that the fragment, variant or derivative is able to elicit anti-anti-idiotype antibodies that specifically bind to the same antigen that the antibody from which the fragment or derivative is derived. In an exemplary embodiment, the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIAcore assay) (see, e.g., Kabat et al., 1991, *Sequences of Proteins of Immunological Interest*, Fifth Edition, National Institute of Health, Bethesda, Md.; Kabat et al., 1980, *J. Immunology* 125(3):961-969).

Useful antibody fragments include, but are not limited to, F(ab')$_2$ fragments, Fab' fragments, Fab fragments, Fvs, single chain antibodies (SCAs) (e.g., as described in U.S. Pat. No. 4,946,778; Bird, 1988, *Science* 242:423-42; Huston et al., 1988, *Proc. Natl. Acad. Sci. USA* 85:5879-5883; and Ward et al., 1989, *Nature* 334:544-54), scFv, scFv-Fc, FvdsFv, minibodies, diabodies, triabodies, tetrabodies, SMIPs (see, e.g., Published U.S. Patent Application No. 2005-0238646; the disclosure of which is incorporated by reference herein) and any other molecule comprising one or more CDRs and that has the same specificity as the antibody.

In other embodiments, the antibody is a fusion protein of an antibody, or a functionally active fragment thereof, joined to another protein. For example, an antibody or antibody fragment can be fused via a covalent bond (e.g., a peptide bond), at either the N-terminus or the C-terminus to an amino acid sequence of another protein (or portion thereof, typically at least a 10, 20 or 50 amino acid portion of the protein) that is not the antibody or an antibody fragment. In some embodiments, the antibody or fragment thereof can be covalently linked to the other protein at the C-terminus of the variable domain or a constant domain.

Antibodies can be modified, e.g., by the covalent attachment of any type of molecule as long as such covalent attachment permits the antibody to retain its antigen-binding immunospecificity. For example, a derivative of an antibody can be one that has been further modified, e.g., by glycosylation, de-glycosylation, acetylation, pegylation, phosphorylation, amidation, derivatization by known protecting/blocking groups, proteolytic cleavage, linkage to another protein, etc. Any of numerous chemical modifications can be carried out by known techniques, including, but not limited to, specific chemical cleavage, acetylation, formylation, metabolic synthesis in the presence of tunicamycin, or the like. Additionally, the derivative can contain one or more unnatural amino acids.

In specific embodiments, it may be desirable to improve the binding affinity and/or other biological properties of the antibody. (See, e.g., U.S. Patent Publication Nos. 2006-0003412 and 2006-0008882; the disclosures of which are incorporated by reference herein; and the discussion infra). Amino acid sequence variants of the antibodies are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletions, insertions, and/or substitutions is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are favored locations for mutagenesis is called "alanine scanning mutagenesis" as described by Cunningham and Wells (1989, *Science* 244: 1081-1085). Here, a residue or group of target residues are identified (e.g., charged residues such as arg, asp, his, lys, and glu) and replaced by a neutral or negatively charged amino acid (typically alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions can include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide.

Another type of antibody is an amino acid substitution variant of an antibody. Such variants have at least one amino acid residue in the antibody molecule replaced by a different residue. The sites of greatest interest for substitutional mutagenesis include the hypervariable regions, but framework region alterations are also contemplated.

Substantial modifications in the biological properties of the antibody can be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally-occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

A particularly type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity). In order to identify candidate hypervariable region sites for modification, alanine scanning mutagenesis can be performed to identify hypervariable region residues contributing significantly to antigen-binding. Alternatively, or additionally, it may be beneficial to analyze a crystal structure of the antigen-antibody complex to identify contact points between the antibody and the antigen. Such contact residues and neighboring residues are candidates for substitution according to the techniques elaborated herein. Once such variants are generated, the panel of variants is subjected to screening and antibodies with superior properties in one or more relevant assays may be selected for further development.

It may be desirable to modify the antibody with respect to effector function, e.g., so as to enhance antibody-dependent cell-mediated cyotoxicity (ADCC), anti-dependent cell phagocytosis (ADCP) and/or complement dependent cytotoxicity (CDC) of the antibody. This may be achieved by introducing one or more amino acid substitutions in an Fc region of the antibody. (See, e.g., Published U.S. Patent Application No. 2006-0160996.) Alternatively or additionally, cysteine residue(s) may be introduced in the Fc region, thereby allowing interchain disulfide bond formation in this region. The homodimeric antibody thus generated may have improved internalization capability and/or increased CDC and ADCC. (See, e.g., Caron et al., 1992, *J. Exp. Med.* 176: 1191-1195; and Shopes, 1992, *J. Immunol.* 148:2918-2922.) Homodimeric antibodies with enhanced anti-tumor activity may also be prepared using heterobifunctional cross-linkers as described in Wolff et al., 1993, *Cancer Research* 53:2560-2565. Alternatively, an antibody can be engineered which has dual Fc regions and may thereby have enhanced complement lysis and ADCC capabilities. (See, e.g., Stevenson et al., 1989, *Anti-Cancer Drug Design* 3:219-230.)

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Antibodies may be glycosylated at conserved positions in their constant regions (see, e.g., Jefferis and Lund, 1997, *Chem. Immunol.* 65:111-128; Wright and Morrison, 1997, *TibTECH* 15:26-32). The oligosaccharide side chains of the immunoglobulins can affect the protein's function (see, e.g., Boyd et al., 1996, *Mol. Immunol.* 32:1311-1318; Wittwe and Howard, 1990, *Biochem.* 29:4175-4180), and the intramolecular interaction between portions of the glycoprotein which can affect the conformation and presented three-dimensional surface of the glycoprotein (see, e.g., Jefferis and Lund, supra; Wyss and Wagner, 1996, *Current Opin. Biotech.* 7:409-416). Oligosaccharides may also serve to target a given glycoprotein to certain molecules based upon specific recognition structures. For example, it has been reported that in a galactosylated IgG, the oligosaccharide moiety 'flips' out of the inter-$C_H2$ space and terminal N-acetylglucosamine residues become available to bind mannose binding protein (see, e.g., Malhotra et al., 1995, *Nature Med.* 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL or CDC) (Boyd et al., 1996, *Mol. Immunol.* 32:1311-1318), while selective removal of sialic acid residues using neuraminidase resulted in no loss of CMCL. Glycosylation of antibodies has also been reported to affect ADCC. In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (see, e.g., Umana et al., 1999, *Nature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (i.e., glycosylation pattern), the extent of glycosylation, or the like.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include, but are not limited to, isolation from a natural source (in the case of naturally-occurring amino acid sequence variants) or preparation by oligonucleotide-mediated (or site-directed) mutagenesis, PCR mutagenesis, or cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. (See, e.g., Hse et al., 1997, *J. Biol. Chem.* 272:9062-9070.) In addition to the choice of host cells, factors which affect glycosylation during recombinant production of antibodies include growth mode, media formulation, culture density, oxygenation, pH, purification schemes, and the like. Various methods have been proposed to alter the glycosylation pattern achieved in a particular host organism, including introducing or overexpressing certain enzymes involved in oligosaccharide production (see, e.g., U.S. Pat. Nos. 5,047,335; 5,510,261; and 5,278, 299). Glycosylation, or certain types of glycosylation, can be enzymatically removed from the glycoprotein, for example using endoglycosidase H (Endo H). In addition, the recombinant host cell can be genetically engineered, e.g., made defective in processing certain types of polysaccharides. These and similar techniques are well known in the art.

The glycosylation structure of antibodies can be readily analyzed by conventional techniques of carbohydrate analysis, including lectin chromatography, NMR, mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides.

The antibodies also can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for CD33 can be obtained commercially, for example, from commercial companies or produced by any method known to one of skill in the art such as, e.g., chemical synthesis or recombinant expression techniques.

In some embodiments, the antibody that specifically binds to CD33 can be humanized M195 antibody (also referred to as HuM195, lintuzumab and Smart M195 (Protein Design Labs, Inc., CA)) (see also U.S. Pat. Nos. 6,007,814 and 5,730,982 and 5,693,761; the disclosures of which are incorporated by reference herein). (The hybridoma producing M195 antibody was deposited with the American Type Culture Collection (Manassas, Va.) as Deposit Number HB-10306.)

In another embodiment, the CD33 binding agent competes for binding with antibody M195. In yet another embodiment, the CD33 binding agent binds to the same epitope as M195. In some embodiments, the CD33 binding agent is a protein that comprises the CDRs of M195, or the variable regions of humanized M195.

In some embodiments, the CD33 binding agent is a protein that specifically binds to CD33 and induces phosphorylation of CD33 and recruitment of SHP-1 upon binding to CD33 on AML cells (e.g., HL-60 cells) in vitro. In some further embodiments, the CD33 binding agent does not cause recruitment of SHP-2 or Syk upon binding to CD33 on AML cells (e.g., HL-60 cells) in vitro.

In other embodiments, the CD33 binding agent is an antibody directed to CD33, such as L4F3, My9, H153, L1B1, P67-5, P67-6, D3HL-60*251, WM53, and WM54 (see Leukocyte Typing IV. White Cell Differentiation Antigens, Knapp et al., eds., Oxford University Press, New York, 1989).

Production of Antibodies

Antibodies can be produced using any method useful for the synthesis of antibodies, in particular, such as by recombinant expression or chemical synthesis.

Recombinant expression of antibodies, or fragments or derivatives thereof, typically involves construction of a nucleic acid that encodes the antibody. If the nucleotide sequence of the antibody is known, a nucleic acid encoding the antibody or a polypeptide thereof may be assembled from chemically synthesized oligonucleotides (e.g., as described in Kutmeier et al., 1994, *BioTechniques* 17:242), which involves the synthesis of overlapping oligonucleotides containing portions of the sequence encoding the antibody, annealing and ligation of those oligonucleotides, and then amplification of the ligated oligonucleotides, e.g., by PCR.

Alternatively, a nucleic acid molecule encoding an antibody or a polypeptide thereof can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by, e.g., PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin is not available), antibodies specific for a particular antigen can be generated by any method known in the art, for example, by immunizing a patient, or suitable animal model such as a rabbit or mouse, to generate polyclonal antibodies or, more preferably, by generating monoclonal antibodies, e.g., as described by Kohler and Milstein (1975, *Nature* 256:

495-497) or, as described by Kozbor et al. (1983, *Immunology Today* 4:72) or Cole et al. (1985, in *Monoclonal Antibodies and Cancer Therapy*, Alan R. Liss, Inc., pp. 77-96). Alternatively, a clone encoding at least the Fab portion of the antibody can be obtained by screening Fab expression libraries (e.g., as described in Huse et al., 1989, *Science* 246:1275-1281) for clones of Fab fragments that bind the specific antigen or by screening antibody libraries (see, e.g., Clackson et al., 1991, *Nature* 352:624; Hane et al., 1997, *Proc. Natl. Acad. Sci. USA* 94:4937).

Once a nucleic acid sequence encoding at least the variable domain of the antibody is obtained, it can be introduced into a vector containing the nucleotide sequence encoding the constant regions of the antibody (see, e.g., International Publication No. WO 86/05807; WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitution(s) or deletion(s) necessary to substitute (or delete) the one or more variable region cysteine residues participating in an intrachain disulfide bond with an amino acid residue that does not contain a sulfhydryl group. Such modifications can be carried out by any method known in the art for the introduction of specific mutations or deletions in a nucleotide sequence, for example, but not limited to, chemical mutagenesis and in vitro site directed mutagenesis (see, e.g., Hutchinson et al., 1978, *J. Biol. Chem.* 253:6551).

In addition, techniques developed for the production of "chimeric antibodies" (see, e.g., Morrison et al., 1984, *Proc. Natl. Acad. Sci. USA* 81:851-855; Neuberger et al., 1984, *Nature* 312:604-608; Takeda et al., 1985, *Nature* 314:452-454). A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (see, e.g., U.S. Pat. No. 4,694,778; Bird, 1988, *Science* 242:423-42; Huston et al., 1988, *Proc. Natl. Acad. Sci. USA* 85:5879-5883; and Ward et al., 1989, *Nature* 334:544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (see, e.g., Skerra et al., 1988, *Science* 242:1038-1041).

Antibody fragments that recognize specific epitopes can be generated by known techniques. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments.

Once a nucleic acid sequence encoding an antibody has been obtained, the vector for the production of the antibody can be produced by recombinant DNA technology using techniques known in the art. Methods that are known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al (1990, *Molecular Cloning, A Laboratory Manual*, $2^{nd}$ Ed., Cold Spring Harbor Laboratory, Cold Spring Harbor, N.Y.; and Sambrook et al., 2001; *Molecular Cloning, A Laboratory Manual*, 3rd ed., Cold Spring Harbor Publish., Cold Spring Harbor, N.Y.) and Ausubel et al. (eds., 1993-2006, *Current Protocols in Molecular Biology*, John Wiley & Sons, NY).

An expression vector comprising the nucleotide sequence of an antibody or the nucleotide sequence of an antibody can be transferred to a host cell by conventional techniques (e.g., electroporation, liposomal transfection, calcium phosphate precipitation or transduction), and the resulting cells are then cultured by conventional techniques to produce the antibody. In specific embodiments, the expression of the antibody is regulated by a constitutive, an inducible or a tissue-specific promoter.

The host cells used to express the recombinant antibody can be either bacterial cells such as *Escherichia coli*, or, preferably, eukaryotic cells, especially for the expression of recombinant immunoglobulin molecules. In particular, mammalian cells such as Chinese hamster ovary cells (CHO), in conjunction with a vector containing the major intermediate early gene promoter element from human cytomegalovirus is an effective expression system for immunoglobulins (see, e.g., Foecking et al., 1986, *Gene* 45: 101; Cockett et al., 1990, *BioTechnology* 8:2). The CHO cell line can be, for example, DG44 or CHO-S. In another example, an antibody can be expressed using the CHEF system. (See, e.g., U.S. Pat. No. 5,888,809; the disclosure of which is incorporated by reference herein.)

A variety of other host-expression vector systems can be utilized to express antibodies. Such host-expression systems represent vehicles by which the coding sequences of the antibody can be produced and subsequently purified, but also represent cells that can, when transformed or transfected with the appropriate nucleotide coding sequences, express an antibody immunoglobulin molecule in situ. These include, but are not limited to, microorganisms such as bacteria (e.g., *E. coli* and *B. subtilis*) transformed with recombinant bacteriophage DNA, plasmid DNA or cosmid DNA expression vectors containing immunoglobulin coding sequences; yeast (e.g., *Saccharomyces pichia*) transformed with recombinant yeast expression vectors containing antibody coding sequences; insect cell systems infected with recombinant virus expression vectors (e.g., baculovirus) containing the immunoglobulin coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing antibody coding sequences; or mammalian cell systems (e.g., COS, CHO, CHO-S, BH, 293, 293T or 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the antibody being expressed. For example, when a large quantity of such a protein is to be produced, vectors that direct the expression of high levels of fusion protein products that are readily purified might be desirable. Such vectors include, but are not limited, to the *E. coli* expression vector pUR278 (Ruther et al., 1983, *EMBO J.* 2:1791-94), in which the antibody coding sequence may be ligated individually into the vector in frame with the lac Z coding region so that a fusion protein is produced; pIN vectors (Inouye and Inouye, 1985, *Nucleic Acids Res.* 13:3101-3109; Van Heeke and Schuster, 1989, *J. Biol. Chem.* 24:5503-5509); and the like. pGEX vectors can also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) or the analogous virus from *Drosophila melanogaster* can be used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) results in a recombinant virus that is viable and capable of expressing the immunoglobulin molecule in infected hosts. (See, e.g., Logan and Shenk, 1984, *Proc. Natl. Acad. Sci. USA* 81:355-359). Specific initiation signals can also be required for efficient translation of inserted antibody coding sequences. These signals include the ATG initiation codon and adjacent sequences. Furthermore, the initiation codon is operably related to the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, *Methods in Enzymol.* 153:51-544).

In addition, a host cell strain can be chosen to modulate the expression of the inserted sequences, or modify and process the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product can be used. Such mammalian host cells include, but are not limited to, CHO (e.g., DG44 or CHO-S), VERY, BH, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines that stably express an antibody can be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method can advantageously be used to engineer cell lines which express the antibody. Such engineered cell lines can be particularly useful in screening and evaluation of tumor antigens that interact directly or indirectly with the antibody.

A number of selection systems can be used. For example, the herpes simplex virus thymidine kinase (see, e.g., Wigler et al., 1977, *Cell* 11:223), hypoxanthine-guanine phosphoribosyltransferase (see, e.g., Szybalska and Szybalski, 1992, *Proc. Natl. Acad. Sci. USA* 48:202), and adenine phosphoribosyltransferase (see, e.g., Lowy et al., 1980, *Cell* 22:817) genes can be employed in tk-, hgprt- or aprt-cells, respectively. Also, antimetabolite resistance can be used as the basis of selection for the following genes: DHFR, which confers resistance to methotrexate (see, e.g., Wigler et al., 1980, *Proc. Natl. Acad. Sci. USA* 77:3567-70; O'Hare et al., 1981, *Proc. Natl. Acad. Sci. USA* 78:1527-31); gpt, which confers resistance to mycophenolic acid (see, e.g., Mulligan and Berg, 1981, *Proc. Natl. Acad. Sci. USA* 78:2072-76); neo, which confers resistance to the aminoglycoside G-418 (see, e.g., *Clinical Pharmacy* 12:488-505; Wu and Wu, 1991, *Biotherapy* 3:87-95; Tolstoshev, 1993, *Ann. Rev. Pharmacol. Toxicol.* 32:573-596; Mulligan, 1993, *Science* 260:926-932; Morgan and Anderson, 1993, *Ann. Rev. Biochem.* 62:191-217; and May, 1993, TIB TECH 11(5):155-215) and hygro, which confers resistance to hygromycin (see, e.g., Santerre et al., 1984, *Gene* 30: 147-50). Methods commonly known in the art of recombinant DNA technology which can be used are described in Ausubel et al (eds., 1993-2006, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds., 1994, *Current Protocols in Human Genetics*, John Wiley & Sons, NY; and Colberre-Garapin et al., 1981, *J. Mol. Biol.* 150:1-14).

The expression levels of an antibody can be increased by vector amplification (for a review, see Bebbington and Hentschel, *The use of vectors based on gene amplification for the expression of cloned genes in mammalian cells in DNA cloning*, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (see, e.g., Crouse et al., 1983, *Mol. Cell. Biol.* 3:257-66).

The host cell can be co-transfected with two expression vectors, the first vector encoding a heavy chain derived polypeptide and the second vector encoding a light chain derived polypeptide. The two vectors can contain the same or different selectable markers that enable equal expression of heavy and light chain polypeptides. Alternatively, a single vector can be used to encode both heavy and light chain polypeptides. In such situations, the light chain is typically placed before the heavy chain to avoid an excess of toxic free heavy chain (see, e.g., Proudfoot, 1986, *Nature* 322:562-65; Kohler, 1980, *Proc. Natl. Acad. Sci. USA* 77:2197-9). The coding sequences for the heavy and light chains can comprise cDNA or genomic DNA.

Once the antibody has been recombinantly expressed, it can be purified using any suitable method for purification of an antibody, for example, by chromatography (e.g., ion exchange, affinity, particularly by affinity for the specific antigen after Protein A, and sizing column chromatography), centrifugation, differential solubility, or by any other standard technique for the purification of proteins.

Binding Agent—Conjugates

In some embodiments, a CD33 binding agent can be administered as an unconjugated antibody. In other embodiments, the CD33 binding agent (e.g., antibody) is bound (i.e., conjugated) to a cytotoxin. The cytotoxin can be any cytotoxic (or cytostatic) agent or drug.

Methods of conjugation of an antibody to a cytotoxic agent or cytotoxin are well-known in the art. In an embodiment, the cytotoxic agent or cytotoxin is chemically conjugated to an anti-CD33 antibody or other CD33 binding agent by standard means known in the art (see, e.g., Trail and Bianchi, 1999, Curr. Opin. Immunol. 11:584-588; Hermanson, 1996, in Bioconjugate Techniques, Academic Press, New York; Zara et al., 1995, Bioconjug. Chem. 6:367-372; Delprino et al., 1993, J. Pharm. Sci. 82:506-512). In some embodiments, the cytotoxic agent and the CD33 binding agent are associated so as to disassociate from each other following internalization, e.g., by using a cleavable linker to conjugate the two moieties. General classes of cleavable linkers are well-known and include: hydrazone linkers (pH sensitive), disulfide linkers (glutathione/reduction sensitive) and peptide linkers (protease sensitive). For examples, see Dubowchik and Walker, 1999, Pharmacol. Therap. 83:67-123.

In another embodiment, the cytotoxic agent or cytotoxin is associated indirectly (i.e., via a non-covalent bond) with a CD33 binding agent. (See, e.g., Dosi et al., 1994, J. Pharm. Sci. 83:206-211.)

In yet another embodiment, the cytotoxic agent and CD33 binding agent are conjugated as a fusion protein (e.g., a peptide cytotoxin fused to the antibody via a peptide bond).

Useful classes of cytotoxic agents or drugs are described supra and also include, for example and not for limitation, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Individual cytotoxic agents or drugs include, for example and not for limitation, an androgen, anthramycin (AMC), asparaginase, 5-azacytidine, azathioprine, bleomycin, busulfan, buthionine sulfoximine, calicheamicin, camptothecin, carboplatin, carmustine (BSNU), CC-1065, chlorambucil, cisplatin, colchicine, cyclophosphamide, cytochalasin B, dacarbazine, dactinomycin (formerly actinomycin), daunorubicin, decarbazine, docetaxel, doxorubicin, etoposide, an estrogen, 5-fluorodeoxyuridine, 5-fluorouracil, gemcitabine, gramicidin D, hydroxyurea, idarubicin, ifosfamide, irinotecan, lomustine (CCNU), maytansine, mechlorethamine, melphalan, 6-mercaptopurine, methotrexate, mithramycin, mitomycin C, mitoxantrone, nitroimidazole, paclitaxel, palytoxin, plicamycin, procarbizine, rhizoxin, streptozotocin, tenoposide, 6-thioguanine, thioTEPA, topotecan, vinblastine, vincristine, vinorelbine, VP-16 and VM-26.

In some typical embodiments, suitable cytotoxic agents or drugs include, for example and not for limitation, DNA minor groove binders (e.g., enediynes and lexitropsins, a CBI compound; see also U.S. Pat. No. 6,130,237), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

In some embodiments, the cytotoxic agent or drug is an anti-tubulin agent. Examples of anti-tubulin agents or drugs include, but are not limited to, taxanes (e.g., Taxol® (paclitaxel), Taxotere® (docetaxel)), T67 (formerly Tularik) and vinca alkyloids (e.g., vincristine, vinblastine, vindesine, and vinorelbine). Other antitubulin agents or drugs include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent or drug is a maytansinoid, another group of anti-tubulin agents or drugs. For example, in specific embodiments, the maytansinoid is maytansine, DM-1 or DM-4 (ImmunoGen, Inc.; see also Chari et al., 1992, Cancer Res. 52:127-131).

In some embodiments, the cytotoxic agent or drug is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP (monoamide of p-phenylene diamine with C-terminal phenylalanine of auristatin F), MMAF (N-methylvaline-valine-dolaisoleuine-dolaproine-phenylalanine), and MMAE (mono-methyl auristatin E). The synthesis and structure of auristatin and dolastin derivatives are described in U.S. Patent Application Publication Nos. 2003/0083263, 2005/0238649 and U.S. Pat. No. 6,884,869; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the cytotoxic agent or drug is a radioisotope. In some embodiments, the cytotoxic agent or drug is radioactive.

In some embodiments, the cytotoxic agent or drug is an antimetabolite. The antimetabolite can be, for example and not for limitation, a purine antagonist (e.g., azathioprine or mycophenolate mofetil), a dihydrofolate reductase inhibitor (e.g., methotrexate), acyclovir, gancyclovir, zidovudine, vidarabine, ribavirin, azidothymidine, cytidine arabinoside, amantadine, dideoxyuridine, iododeoxyuridine, poscarnet, or trifluridine.

In other embodiments, the cytotoxic agent or drug is tacrolimus, cyclosporine or rapamycin. In further embodiments, the cytotoxic agent or drug is aldesleukin, alemtuzumab, alitretinoin, allopurinol, altretamine, amifostine, anastrozole, arsenic trioxide, bexarotene, bexarotene, calusterone, capecitabine, celecoxib, cladribine, Denileukin diftitox, dexrazoxane, dromostanolone propionate, epirubicin, estramustine, exemestane, Filgrastim, floxuridine, fludarabine, fulvestrant, gemcitabine, gemtuzamab ozogamicin, goserelin, idarubicin, ifosfamide, imatinib mesylate, Interferon alfa-2a, irinotecan, letrozole, leucovorin, levamisole, mechlorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine or zoledronate.

In some embodiments, the cytotoxin is not calicheamicin or a derivative thereof. In some embodiments, the cytotoxin is not a radioisotope.

Compositions and Methods of Administration

The CD33 binding agents can be in any form that allows for the composition to be administered to a patient. For example, the composition can be in the form of a solid or liquid. Typical routes of administration include, without limitation, parenteral and intra-tumor. Parenteral administration includes subcutaneous injections, intravenous, intramuscular, intrasternal injection or infusion techniques. In one aspect, the compositions are administered parenterally. In yet another aspect, the compounds are administered intravenously.

Pharmaceutical compositions can be formulated so as to allow a compound to be bioavailable upon administration of the composition to a patient. Compositions can take the form of one or more dosage units, where, for example, a container of a compound in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of patient (e.g., human), the particular form of the compound, the manner of administration, and the composition employed.

The pharmaceutically acceptable carrier or vehicle can be particulate, so that the compositions are, for example, in powder form. The carrier(s) can be liquid, with the compositions being, for example, an injectable liquid.

The composition can be in the form of a liquid, e.g., for parenteral injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; stabilizers such as amino acids; surfactants such as polysorbates; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the composition that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a drug(s) or agent(s) such that a suitable dosage will be obtained. Typically, this amount is at least about 0.01% of a drug or agent by weight of the composition. When intended for oral administration, this amount can be varied to range from about 0.1% to about 80% by weight of the composition. In one aspect, oral compositions can comprise from about 4% to about 50% of the compound by weight of the composition. In yet another aspect, present compositions are prepared so that a parenteral dosage unit contains from about 0.01% to about 2% by weight of the compound.

For intravenous administration, the composition can comprise from about 1 to about 50 mg of a drug or agent per kg of the animal's body weight. In one aspect, the composition can include from about 1, 1.5 or 2.5 to about 50 mg of a drug or agent per kg of the animal's body weight. In another aspect, the amount administered will be in the range from about 1, 1.5 or 2.5 to about 25 mg/kg of body weight of a drug or agent.

In some embodiments, the dosage administered to a patient is 1.5 mg/kg to about 12 mg/kg, 1.5 mg/kg to about 15 mg/kg, 2.5 mg/kg to about 12 mg/kg, or 2.5 mg/kg to about 12 mg/kg of the patient's body weight. In some embodiments, the dosage administered to a patient is between about 1 mg/kg and about 25 mg/kg of the patient's body weight. In some embodiments, the dosage administered to a patient is between about 1 mg/kg, 1.5 mg/kg or 2.5 mg/kg and about 20 mg/kg of the patient's body weight. In some embodiments, the dosage administered is between about 1 mg/kg, 1.5 mg/kg or 2.5 mg/kg to about 20 mg/kg of the patient's body weight. In some embodiments, the dosage administered is between about 1 mg/kg, 1.5 mg/kg or 2.5 mg/kg to about 15 mg/kg of the patient's body weight. In some embodiments, the dosage administered is between about 1 mg/kg, 1.5 mg/kg or 2.5 mg/kg to about 10 mg/kg of the patient's body weight. (For conversion to mg/mm$^2$, a BSA of 1.8 m$^2$ and a body weight of 80 kg can be used.) In yet another embodiment, the dose administered is about 500-700 mg, sometimes about 550-650 mg, for example about 600 mg, regardless of body weight.

As discussed herein, a CD33 binding agent can be administered intravenously to the patient on a schedule that is, for example, daily, weekly, biweekly, tri-weekly or monthly to the patient. For example, a CD33 binding agent can be administered weekly, for a period of 2 to 10 weeks, typically 3-6 weeks. In some embodiments, the dosage regimen of the CD33 binding agent maintains a blood serum concentration of antibody at least 5 µg/ml or at least 10 µg/ml during the dosage cycle. The CD33 binding agent can be administered, for example, from 1-8, or more cycles. In some embodiments, a CD33 binding agent is administered chronically to a subject. For example, the CD33 binding agent can be administered weekly in an initial dosing phase for a period of 1 to 8 weeks. The initial dosing phase can be followed by a maintenance phase, in which the CD33 binding agent is administered weekly or biweekly.

By way of example, the invention includes a method of treating a cancer, such as myeloid leukemia, by administering about 1.5 mg/kg to about 12 mg/kg, for instance about 1.5-8 or 2.5-8 mg/kg, of an anti-CD33 antibody such as SGN-33 weekly. This treatment usually can be continued for about 1-3 months, typically about two months. In an embodiment, the dosing schedule is maintained until a reduction in blasts is noted. For example, dosing can be continued up to about 6 months. This treatment can be followed by a less frequent dosing schedule, involving for instance biweekly doses (or twice per month). This dosing schedule can be maintained 1, 2, 3, 4, 5, 6 months or more to maintain a reduction in blasts and/or a remission.

In some embodiments, a prophylactic agent can be administered with a CD33 binding agent to minimize infusion reactions. Suitable prophylactic agents include, for example, methylprednisolone, diphenyldramine, acetaminophen or other suitable agent. The prophylactic agent can be administered prior to or at about the same time as the CD33 binding agent.

The drug(s) or agent(s) or compositions can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., encapsulation in liposomes, microparticles, microcapsules, capsules, etc., and can be used to administer a compound. In certain embodiments, more than one drug or agent or composition is administered to a patient.

It can be desirable to administer one or more drugs or agents or compositions locally to the area in need of treatment, as appropriate for the drug or agent. This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as silastic membranes, or fibers. In one embodiment, administration can be by direct injection at the site (or former site) of a cancer, tumor or neoplastic or pre-neoplastic tissue.

The drug(s) or agent(s) or compositions can be delivered in a controlled release system, such as a pump or various polymeric materials. In yet another embodiment, a controlled-release system can be placed in proximity of the target of the drug(s) or agent(s) or compositions, thus requiring only a fraction of the systemic dose (see, e.g., Goodson, in *Medical Applications of Controlled Release*, vol. 2, pp. 115-138 (1984)). Other controlled-release systems discussed in the review by Langer (1990, *Science* 249:1527-1533) can be used.

The drugs or agents are formulated in accordance with routine procedures as a pharmaceutical composition adapted for intravenous administration to animals, particularly human beings, as appropriate for the drug or agent. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where drug or agent is to be administered by infusion, it can be dispensed, for example, with an infusion bottle containing sterile pharmaceutical grade water or saline. Where the drug or agent is administered by injection, an ampoule of sterile water for injection or saline can be provided so that the ingredients can be mixed prior to administration.

Compositions of therapeutic agents also can be administered according to accepted dosage forms in the form of tablets, lozenges, aqueous or oily suspensions, granules, powders, emulsions, capsules, syrups, or elixirs, for example. Orally administered compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered drugs or agents. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used.

The composition can include various materials that modify the physical form of a solid or liquid dosage unit. For example, the composition can include materials that form a coating shell around the active ingredients. The materials that form the coating shell are typically inert, and can be selected from, for example, sugar, shellac, and other enteric coating agents. Alternatively, the active ingredients can be encased in a gelatin capsule.

The compositions can be administered to a patient in need thereof at a frequency, or over a period of time, that is determined by the attending physician. The compositions can be administered over a period of 1 day, 2 days, 3 days, 5 days, 7 days, 10 days, 14 days, 21 days, 28 days, one month, two months, or longer periods of time. It is understood that the compositions can be administered for any period of time between 1 day and two months or longer.

The invention is further described in the following Examples.

EXAMPLES

Example 1

Signaling Induced by Anti-CD33 Antibody in CD33-Positive AML Lines

The purpose of this study was to determine if the anti-CD33 antibody, a humanized M195 antibody (also referred to as lintuzumab or SGN-33), exerts its biological activity directly by blocking cell proliferation, or indirectly through interactions with effector cells. The cell proliferation inhibitory activity of certain anti-CD33 antibodies has been associated with a signaling cascade that includes CD33 tyrosine phosphorylation, Syk kinase phosphorylation and recruitment of SHP phosphatases.

CD33-positive cell lines were treated with anti-CD33 antibodies (lintuzumab and certain commercially available antibodies). Cell extracts were prepared and CD33 was immunoprecipitated using an anti-CD33 antibody (MY9 clone; Beckman Coulter, Calif.). Western blotting was performed with an anti-phosphotyrosine antibody (4G10; Upstate Biotechnologies, Inc., Lake Placid, N.Y.). As shown in FIG. 1, exposure of the CD33-positive AML cell line HL-60 to both soluble and cross-linked SGN-33 stimulated CD33 tyrosine phosphorylation. Two forms of CD33 were detected (due to either splicing of CD33 mRNA or post-translational modification of CD33).

Figure 2:
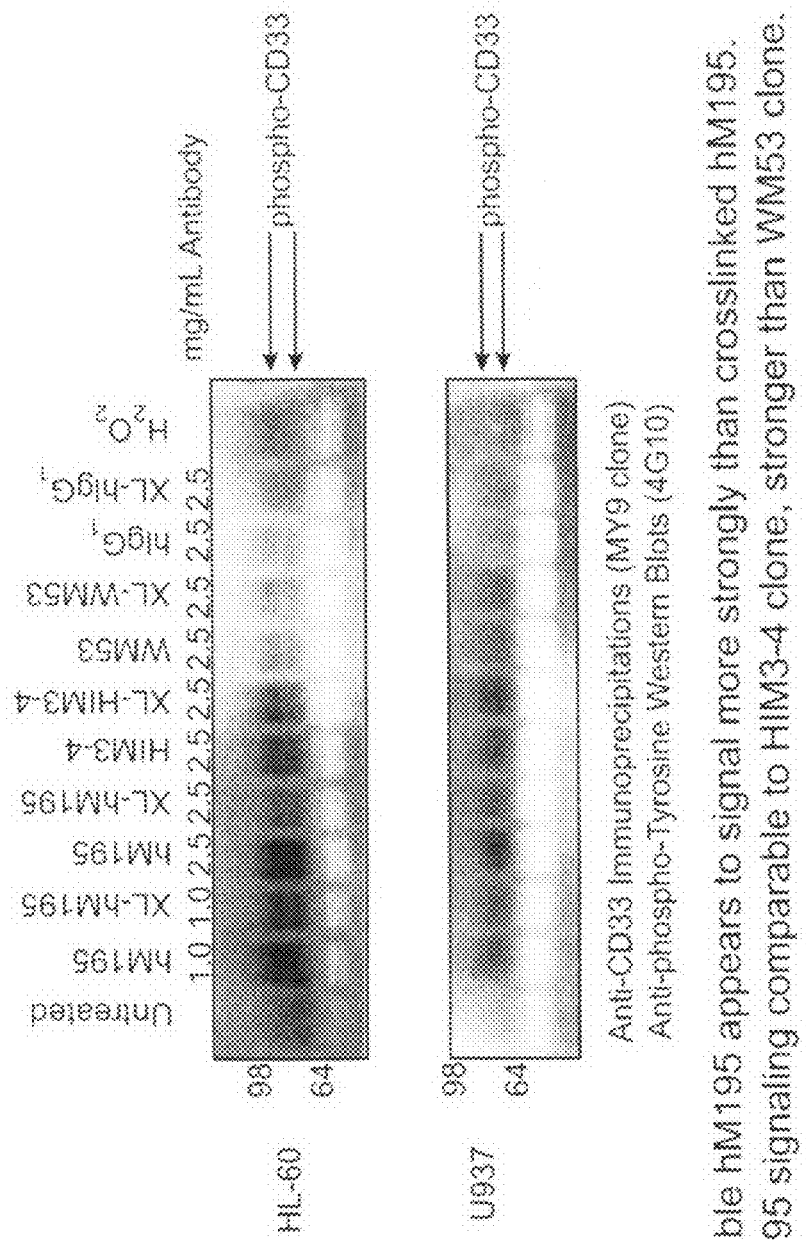
FIG. 2 shows a Western blot of CD33 phosphorylation in cell lysates prepared from HL-60 or U937 AML cells treated with the indicated soluble or cross-linked (XL) anti-CD33 antibodies (hM195, HIM3-4, and WM53) or control human IgG$_1$. CD33 was immunoprecipitated using the MY9 anti-CD33 antibody. Phosphorylation of CD33 was detected using the 4G10 anti-phosphotyrosine antibody.

As shown in FIG. 2, the humanized M195 antibody stimulated CD33 tyrosine phosphorylation in two CD33-positive myeloid cell lines, HL-60 and U937 cells. Soluble humanized antibody was more effective than cross-linked antibody in stimulating CD33 tyrosine phosphorylation. Another anti-CD33 antibody, HIM3-4 (Abcam, Inc., Cambridge, Mass.), either soluble or cross-linked, was equally effective in stimulating CD33 tyrosine phosphorylation in HL-60 and U937 cells. A third anti-CD33 antibody, WM53 (Abcam, Inc., Cambridge, Mass.), was marginally effective in stimulating CD33 tyrosine phosphorylation in HL-60 and U937 cells (compare with negative control human IgG1 antibody).

Figure 3:
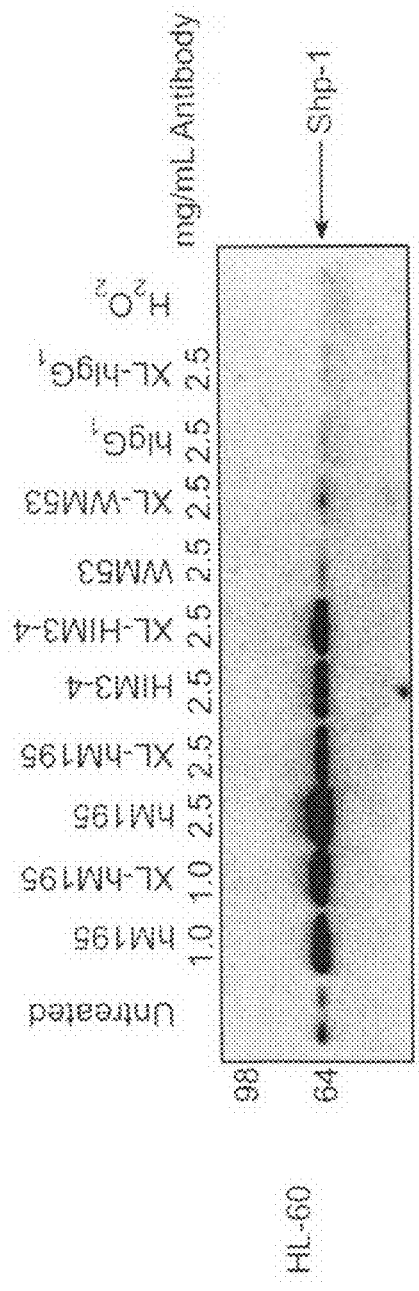
FIG. 3 shows a Western blot of SHP-1 recruitment in cell lysates prepared from HL-60 cells treated with the indicated soluble or cross-linked (XL) anti-CD33 antibodies (hM195, HIM3-4, and WM53) or control human IgG$_1$. CD33 was immunoprecipitated using the MY9 anti-CD33 antibody and SHP-1 was detected using sc-287 anti-SHP-1 antibody.

To determine whether the humanized M195 antibody also recruits SHP phosphatases, HL-60 cells were treated with soluble or cross-linked anti-CD33 antibodies. Cell extracts were prepared and CD33 was immunoprecipitated with an anti-CD33 antibody (MY9 clone). Western blotting was performed with an anti-SHP-1 antibody (sc-287; Santa Cruz Biotechnology, Inc., Santa Cruz, Calif.). As shown in FIG. 3, two anti-CD33 antibodies, HuM195 and HIM3-4, either soluble or cross-linked, recruited SHP-1 to CD33. The recruitment of SHP-1 correlated with the level of CD33 tyrosine phosphorylation (compare FIGS. 2 and 3). In contrast, HuM195 antibody did not recruit SHP-2 or Syk (data not shown).

Example 2

Effects of Anti-CD33 Antibody-Mediated CDC on CD33-Positive AML Lines

Figure 4:
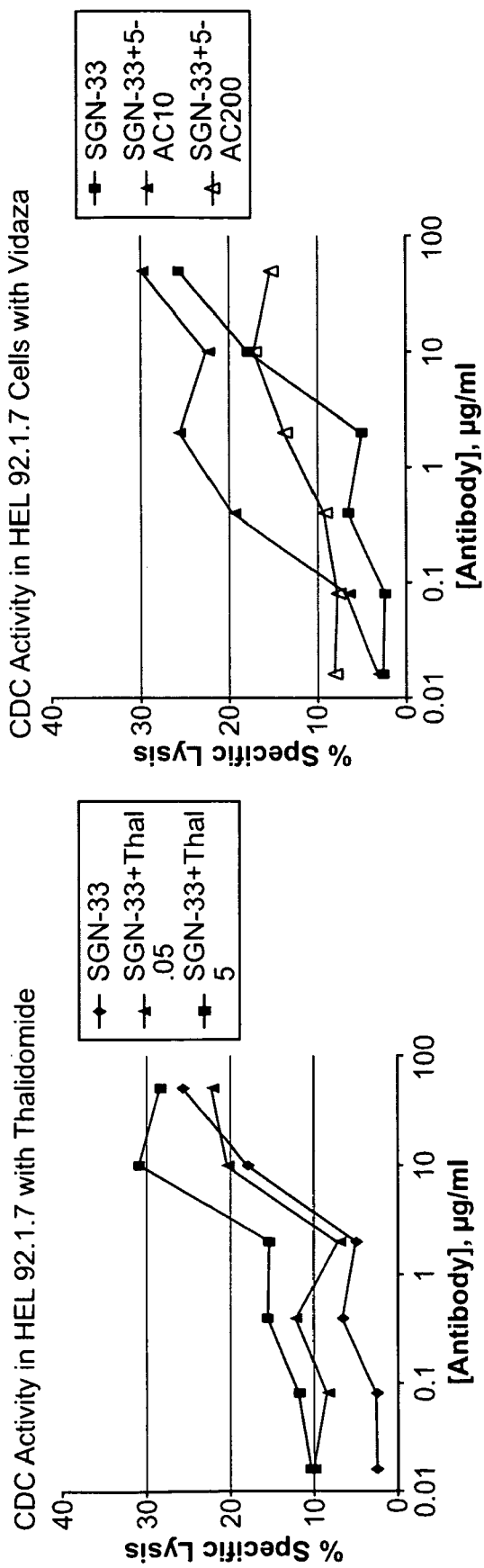
FIG. 4 shows the effect of thalidomide or 5-azacytidine (Vidaza™) on anti-CD33 antibody (SGN-33)-mediated complement dependent cytotoxicity (CDC) activity on HEL 92.1.7 cells. The HEL 92.1.7 cells were pre-incubated with the indicated concentrations of thalidomide or 5-azacytidine for 2 hours prior to exposure to SGN-33.

The purpose of this study was to determine whether the cytotoxic effects of an anti-CD33 antibody (HuM195) on AML cells could be enhanced by combination treatment with chemotherapeutic drugs. An MDR+, CD33-positive AML cell line (HEL 92.1.7) was either untreated or preincubated with the indicated concentrations of thalidomide or 5-azacytidine for two hours prior to exposure to the anti-CD33 Ab. Cytotoxic activity was measured using a complement-dependent cytotoxicity (CDC) activity. As shown in FIG. 4, HuM195 antibody increased lysis of AML cell lines in a dose-dependent manner. Preincubation with thalidomide or 5-azacytidine each enhanced the sensitivity of the MDR+, AML cell lines to HuM195-mediated CDC activity.

Example 3

Effects of Anti-CD33 Antibody on Primary Macrophages

This study was performed to determine whether anti-CD33 antibodies have direct effects on CD33-positive macrophages in modulating the production of cytokines, chemokines and growth factors, which themselves may contribute to the growth and progression of tumors in vivo.

Primary human macrophages were generated from long-term cultures of freshly isolated human peripheral blood mononuclear cells (PBMCs; AllCells, Emeryville, Calif. or LifeBlood, Memphis, Tenn.). PBMCs were cultured in tissue culture flasks in RPMI 1640 medium containing glutamine (Invitrogen, Grand Island, N.Y.), 10% heat-inactivated FBS, and antibiotics for 3 to 4 hours. Non-adherent cells were removed by washing with PBS and the adherent cells were cultured in OptiMem-I medium (Invitrogen) containing 1% heat-inactivated FBS for 1 to 2 hours. The cells were washed with PBS and cultured for 10 to 14 days in X-VIVO-15 medium (Cambrex Bio Science, Walkersville, Md.) containing 500 U/ml GM-CSF (Peprotech, Rocky Hill, N.J.).

Macrophages were harvested, counted, and cultured in 96-well plates at 35,000 cells per well. G-CSF-mobilized CD14+ monocytes (Cambrex) were cultured in 96-well plates at 100,000 cells per well (adherent cells) in sterile polypropylene dishes (non-adherent cells). After 1 hour, macrophages or monocytes were exposed to anti-CD33 Ab (HuM195 Ab (also referred to as SGN-33) at 10 or 25 μg/ml). After 3 to 4 hours, interferon-gamma (IFN-γ) (300 U/ml; R&D Systems, Minneapolis, Minn.) or medium containing 20% conditioned tumor cell media, which was collected from cultures of human tumor cell lines, such as RPMI-8226 or Karpas-620 multiple myeloma cells. After 24 to 48 hours, culture supernatants were collected and analyzed for levels of a variety of cytokines, chemokines and growth factors, including tumor necrosis factor-alpha (TNF-α), interleukin-6 (IL-6), interleukin-8 (IL-8), and monocyte chemoattractant protein-1 (MCP-1), using the Flow CytoMix system (Bender MedSystems, Burlingame, Calif.), and RANTES by ELISA (Pierce-Endogen, Rockford, Ill.). In parallel, cultures were treated with SGN-33 for 24 to 72 hours, and cell viability was tested using CelltiterGlo (Promega, Madison, Wis.).

Figure 5:
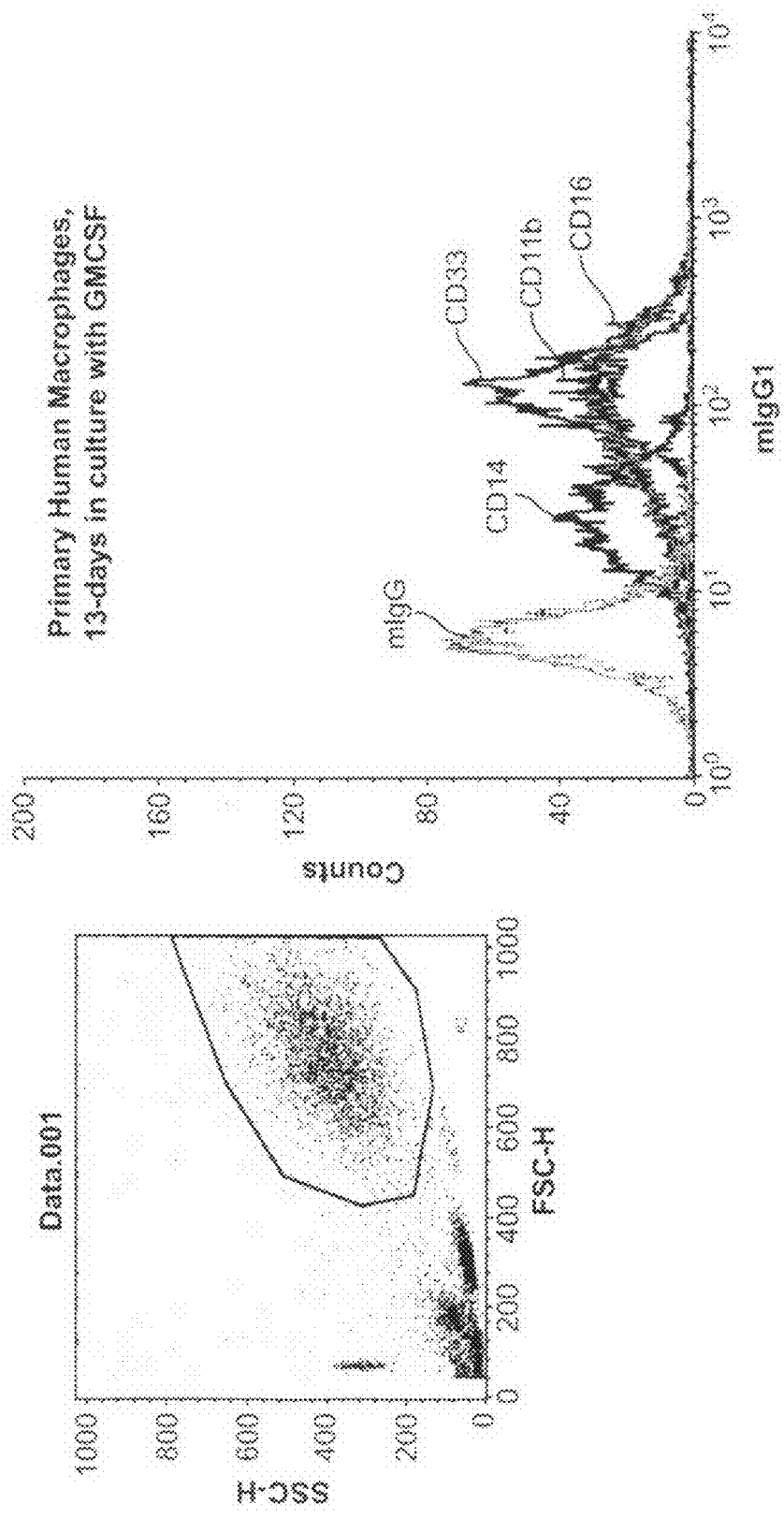
FIG. 5 shows a flow cytometry analysis of primary cultured human macrophages demonstrating expression of CD33 and the phenotypic markers CD11b, CD14 and CD16 on such macrophages.

Macrophages and CD14+ monocytes were analyzed by flow cytometry (BD FacSCAN) for the expression of phenotypic cell surface markers CD14, CD11b, CD16, CD33, CD40 and CD86 using commercially available antibodies (BD Pharmingen, San Diego, Calif.). As shown in FIG. 5, the cultured human macrophages express the expected phenotypic markers (CD11b, CD14 and CD16) and CD33.

Figure 6:
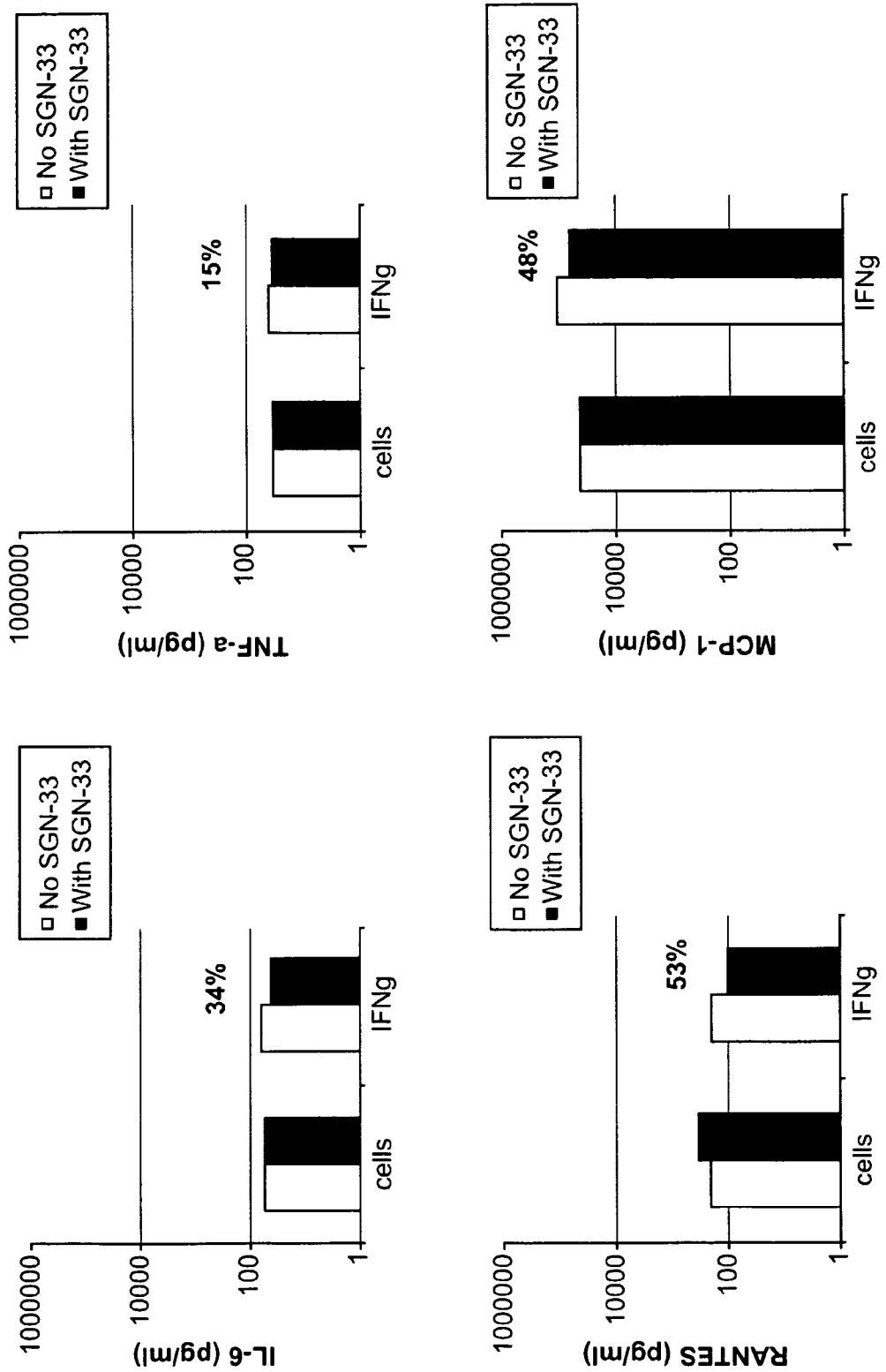
FIG. 6 shows the effect of an anti-CD33 antibody (SGN-33) on the production of IL-6, TNF-α, RANTES and MCP-1 by primary human macrophages treated for 24 hours with IFN-γ. The data shown is representative of values obtained using 5 different donors.
Figure 7:
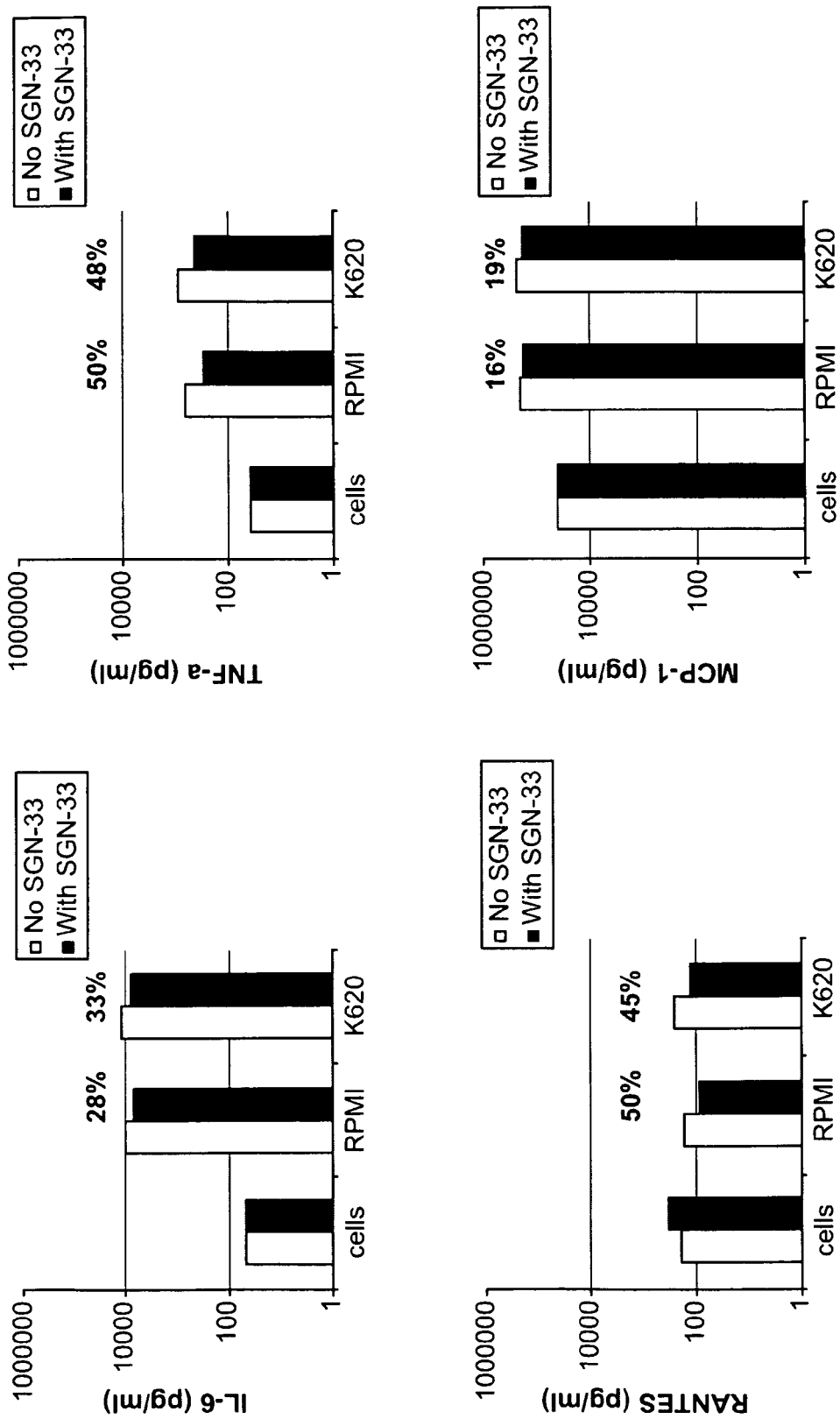
FIG. 7 shows the effect of an anti-CD33 antibody (SGN-33) on production of IL-6, TNF-α, RANTES and MCP-1 by primary human macrophages treated for 24 hours with conditioned media from RPMI-8226 or Karpas-620 multiple myeloma cells, as indicated. The data shown is representative of values obtained using 5 different donors.

Human macrophages produce and secrete numerous cytokines, chemokines and growth factors, in the absence of treatment, or in response to treatment for 24 hours with IFN-γ (FIG. 6) or with conditioned medium from cultures of two human tumor cell lines, RPMI-8226 and Karpas-620 cells (FIG. 7). (Note the logarithmic scale for the X-axis; the percent reduction is shown in the figures.)

Figure 8:
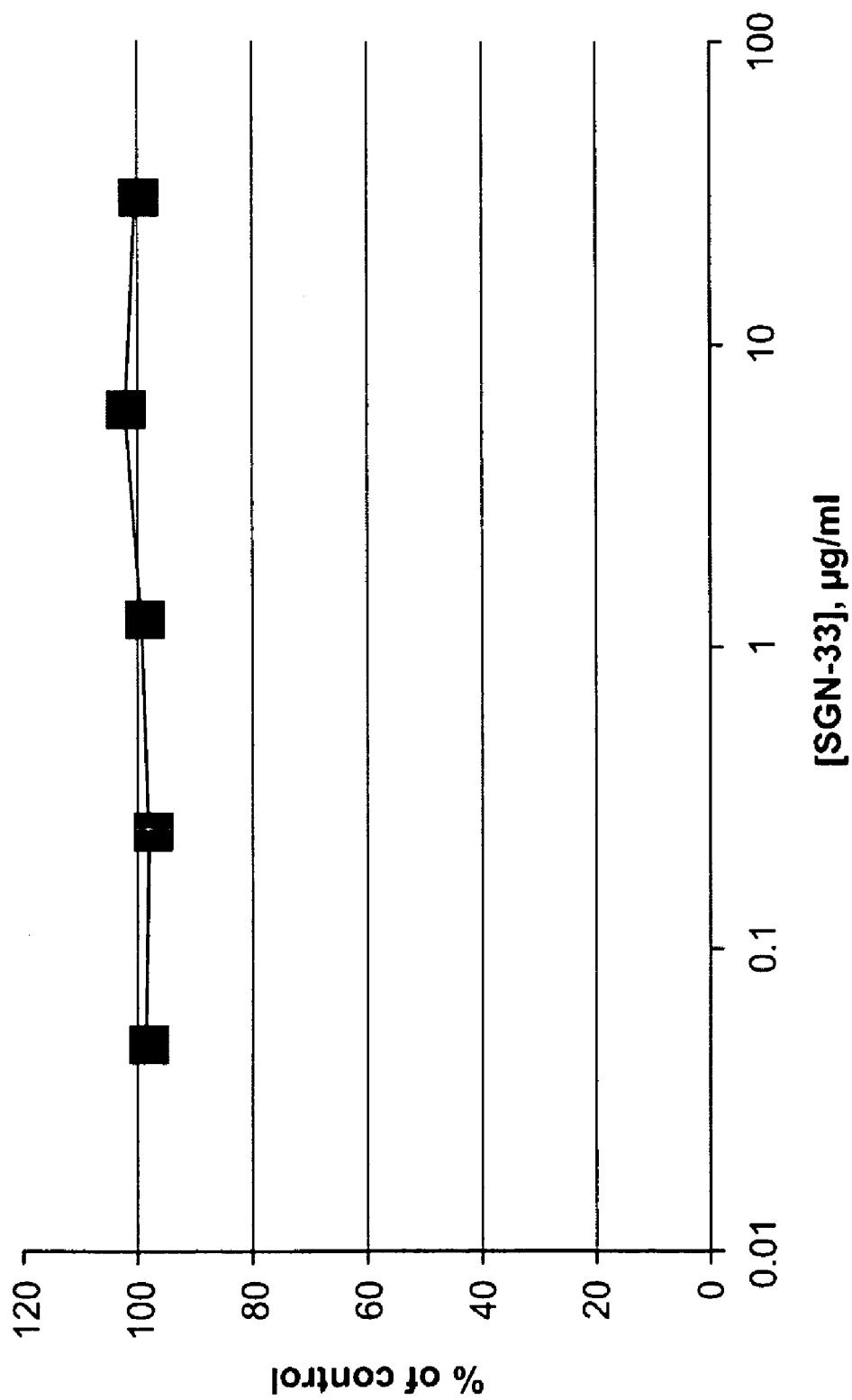
FIG. 8 shows that an anti-CD33 antibody (SGN-33) does not affect the viability of primary human macrophages. Viability was assessed after 24 to 72 hours of exposure to increasing concentrations of SGN-33.

The effects of pre-incubation of human macrophages with an anti-CD33 antibody, SGN-33, were investigated. Unexpectedly, pre-incubation for 3 hours with SGN-33 reduced production of IL-6, TNF-α, RANTES, and MCP-1 in response to IFN-γ (see FIG. 6), or to conditioned media from RPMI-8226 and Karpas-620 cells (see FIG. 7). As shown in FIG. 8, the reduced secretion of IL-6, TNFα, RANTES, and MCP-1 from the human macrophages was not due to an adverse effect of the anti-CD33 antibody on cell viability. Thus, anti-CD33 antibody can affect the production of cytokines, chemokines and growth factors in human macrophages without interfering with cell viability.

Figure 9:
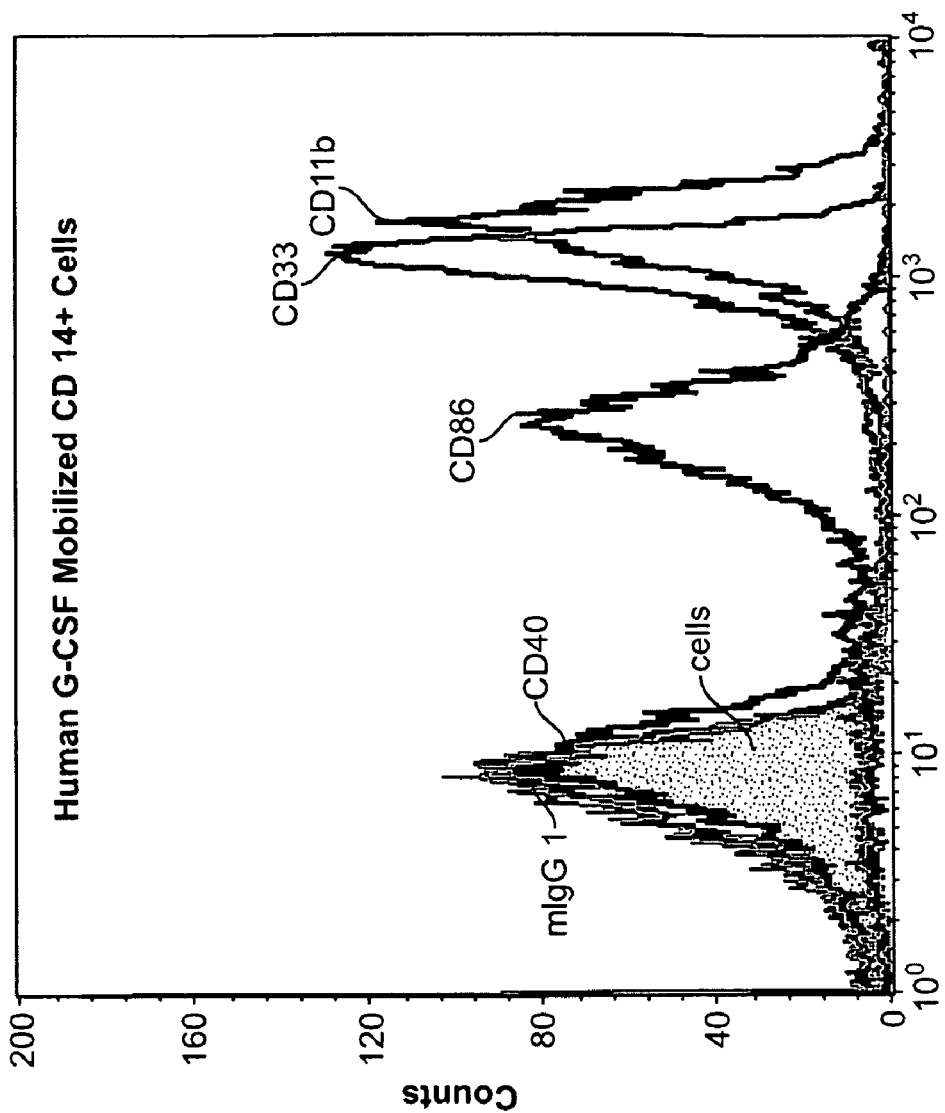
FIG. 9 shows a flow cytometry analysis of primary cultured human CD14$^+$ monocytes demonstrating expression of CD33 and the phenotypic markers CD11b, CD40 and CD86 on such monocytes.
Figure 9:
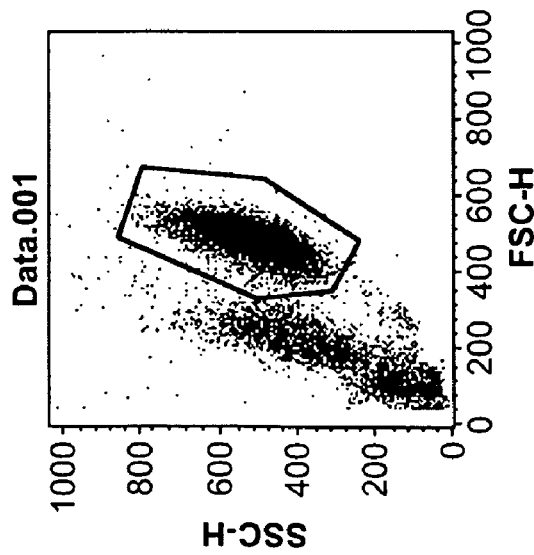

The effect of the anti-CD33 antibody on production of cytokines, chemokines and growth factors in adherent and non-adherent human CD14+ monocytes was also investigated. As shown in FIG. 9, cultured human G-CSF mobilized human CD14+ monocytes express the expected phenotypic markers (CD11b, CD40 and CD86) and CD33.

Figure 10:
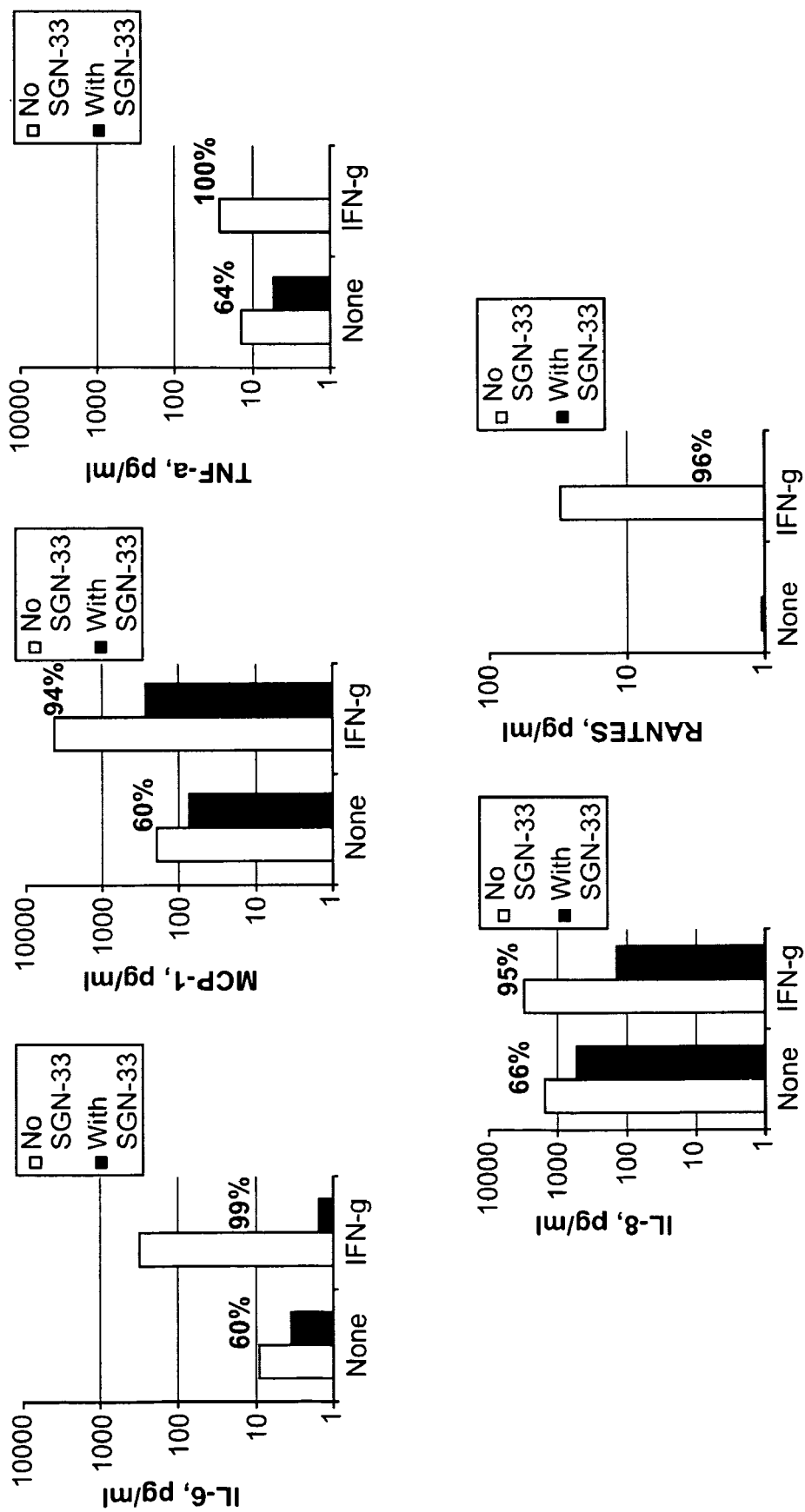
FIG. 10 shows the effect of an anti-CD33 antibody (SGN-33) on production of IL-6, MCP-1, TNF-α, IL-8 and RANTES by activated, adherent human CD14+ monocytes treated for 48 hours with IFN-γ. The data shown is representative of values obtained using 2 different donors.
Figure 11:
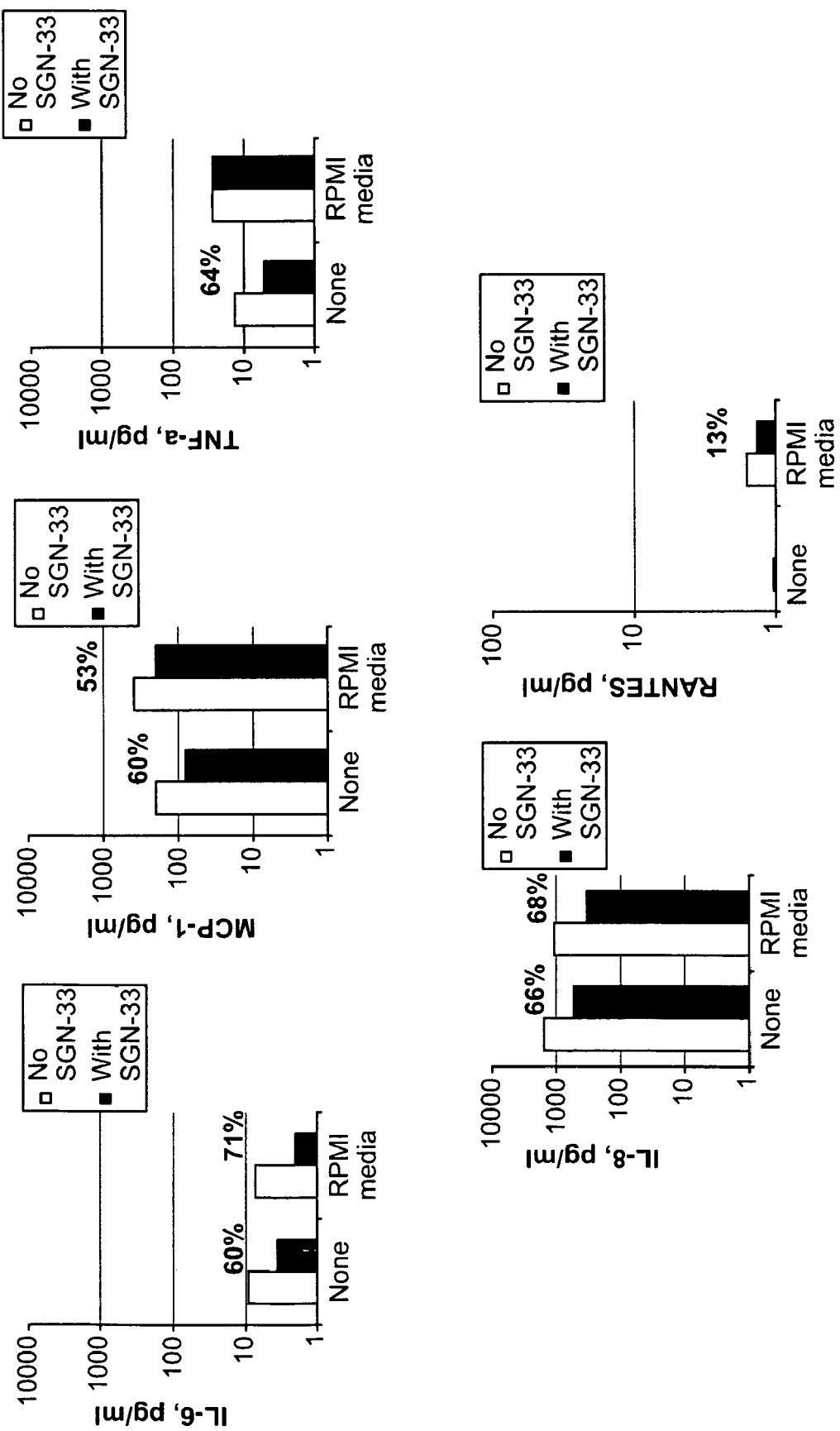
FIG. 11 shows the effect of an anti-CD33 antibody (SGN-33) on the production of IL-6, MCP-1, TNF-α, IL-8 and RANTES in activated, adherent human CD14+ monocytes treated for 48 hours with conditioned media from RPMI-8226 multiple myeloma cells. The data shown is representative of values obtained using 2 different donors.

In cultures of adherent human CD14+ monocytes, the anti-CD33 antibody reduced the basal levels and IFN-γ stimulated levels of IL-6, MCP-1, TNF-α, and IL-8, and the IFN-γ stimulated level of RANTES (see FIG. 10). The anti-CD33 antibody SGN-33 also reduced the basal levels and the RPMI-8228 conditioned media stimulated levels of IL-6, MCP-1, and IL-8, and the RPMI-8228 conditioned media stimulated level of RANTES (see FIG. 11). SGN-33 reduced the basal level, but not the RPMI-8228 conditioned media stimulated level, of TNF-α (see FIG. 11).

Figure 12:
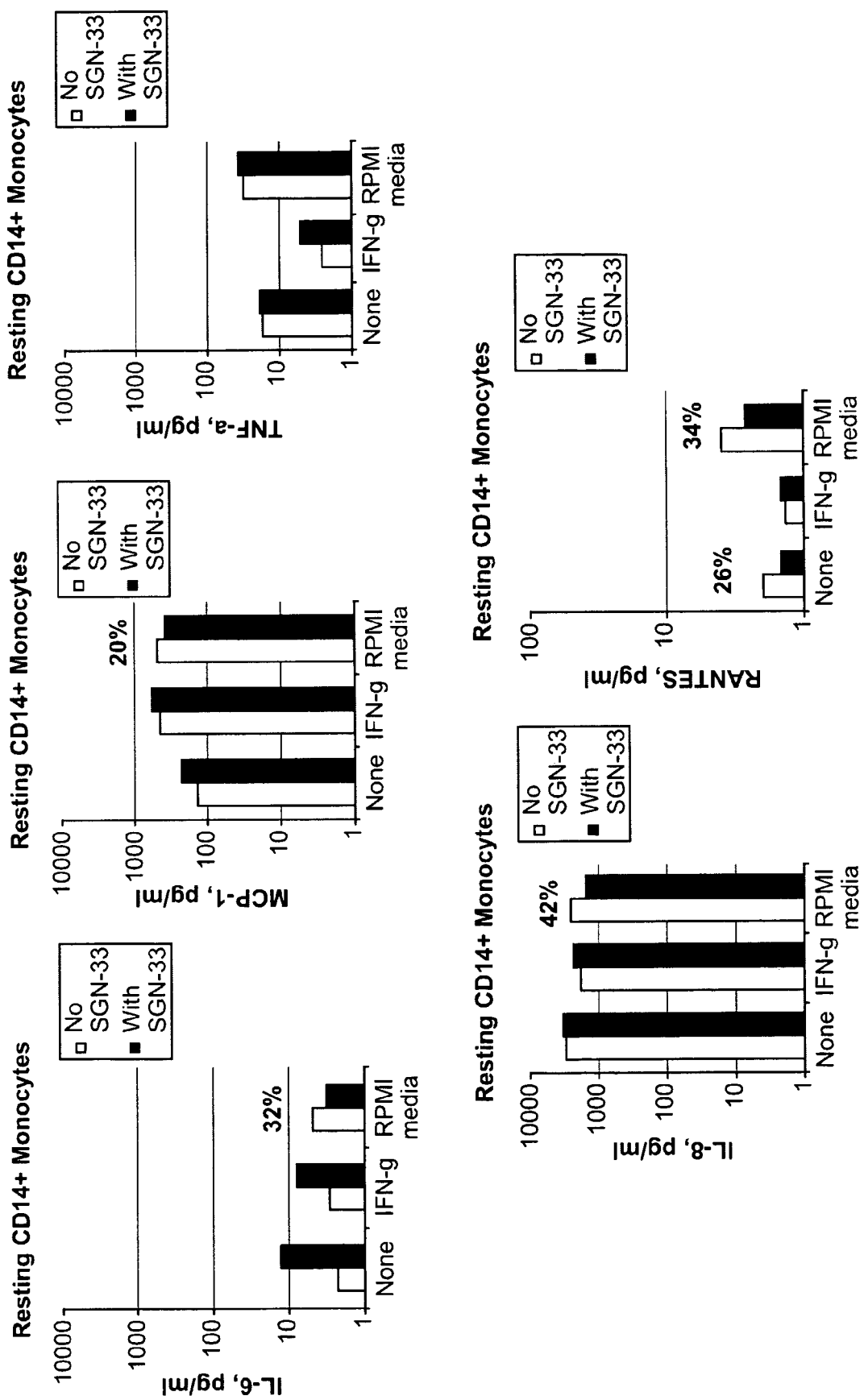
FIG. 12 shows the effect of an anti-CD33 antibody (SGN-33) on the production of IL-6, MCP-1, TNF-α, IL-8 and RANTES by non-adherent human CD14+ monocytes treated for 48 hours with IFN-γ or with conditioned media from RPMI-8226 or Karpas-620 multiple myeloma cells as indicated. The data shown is representative of values obtained using 2 different donors.
Figure 13:
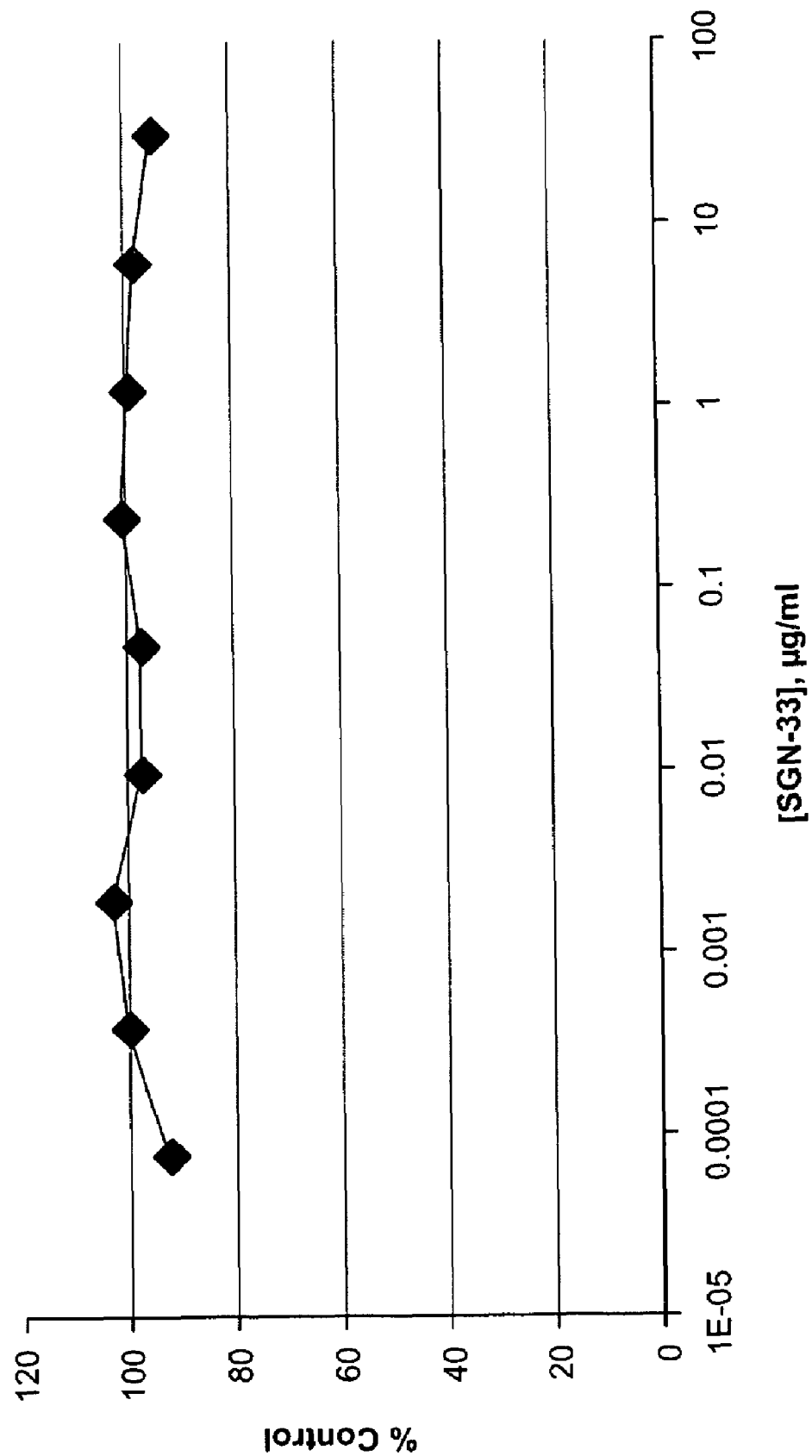
FIG. 13 shows that an anti-CD33 antibody (SGN-33) does not affect the viability of primary human CD14+ monocytes. Viability was assessed after 48 hours of exposure to increasing concentrations of SGN-33.

Marked differences in the effects of IFN-γ, RPMI-8226 conditioned media, and SGN-33 were observed in cultures of non-adherent CD14+ monocytes (see FIG. 12). IFN-γ exerted minimal stimulatory effects on production of cytokines, chemokines and growth factors, and this production was not inhibited by SGN-33, except for the basal level of RANTES. In fact, small increases in levels of IL-6, IL-8, TNF-α and MCP-1 were observed upon exposure of non-adherent CD14+ monocytes to SGN-33. The levels of IL-6, MCP-1, IL8 and RANTES stimulated by RPMI-8226 conditioned media was reduced by SGN-33 (see FIG. 12). As shown in FIG. 13, the effects of the anti-CD33 antibody SGN-33 on production of cytokines, chemokines, and growth factors in primary human monocytes was not due to an adverse effect of the antibody, SGN-33, on cell viability.

Taken together, the above results demonstrate that an antibody to CD33 is capable inhibiting the production of a broad spectrum of cytokines, chemokines and growth factors, which were enhanced in the presence of pro-inflammatory cytokines, like IFN-γ, or inducing agents present in the conditioned media from tumor cells. The anti-CD33 antibody appears to be able to reduce production of a variety of cytokines, chemokines and growth factors in human monocytes and macrophages without affecting cell viability.

Example 4

Expression of CD33 on Macrophages in Atopic Dermatitis Lesions

The purpose of this study was to determine whether CD33 is expressed on cells in the lesions of atopic dermatitis patients.

OCT embedded skin lesions from atopic dermatitis patients were stained using immunofluorescence. Frozen sections of the skin lesions were acetone fixed and then incubated with primary antibodies, either anti-human CD33 mouse monoclonal antibody or mouse IgG isotype antibody. Secondary antibody labeling was performed using Alexa fluor-568 goat anti-mouse IgG.

Using the anti-CD33 antibody, macrophages in the atopic dermatitis lesions were found to express CD33.

Example 5

Anti-CD33 Antibody Blocks the Migration of Human Macrophages in Response to Chemoattractants In this study, the ability of the anti-CD33 antibody SGN-33 to affect the movement of human macrophages in response to migration-promoting chemoattractants such as conditioned tumor cell media, TGF-β, VEGF, TNF-α, and IFN-γ. SGN-33 significantly opposed the migration of macrophages in response to these factors. These results complement previous findings that SGN-33 blocked the production of cytokines and chemokines from activated monocytes and macrophages. Thus SGN-33 modulates the activity and function of activated monocytes and macrophages.

Primary human macrophages were generated from long-term culture of freshly isolated human PBMCs (AllCells, Emeryville, Calif. or LifeBlood, Memphis, Tenn.) upon long-term culture in X-VIVO-15 medium (Cambrex Walkersville, Md.) containing GM-CSF (PeproTech, Rocky Hill, N.J.).

The migration of macrophages in response to challenge with plating media containing 10% human serum, 20% conditioned tumor cell media, or 50 ng/ml TGF-β, VEGF, TNF-α, or IFN-γ was evaluated using the CytoSelect Cell Migration Assay (Cell Biolabs, San Diego, Calif.). Macrophages were treated with SGN-33 or the F(ab')₂ fragment of SGN-33 for 30 to 45 minutes prior to plating in RPMI media containing 1% human serum. In some studies, the macrophages were pre-treated with neuraminidase (Sigma, St. Louis, Mo.) for 1 hour prior to incubation with SGN-33. The study was stopped 18 hours later and migration was evaluated after dissociation of the cells from the membrane followed by detection with Cyquant GR dye.

Figure 14A:
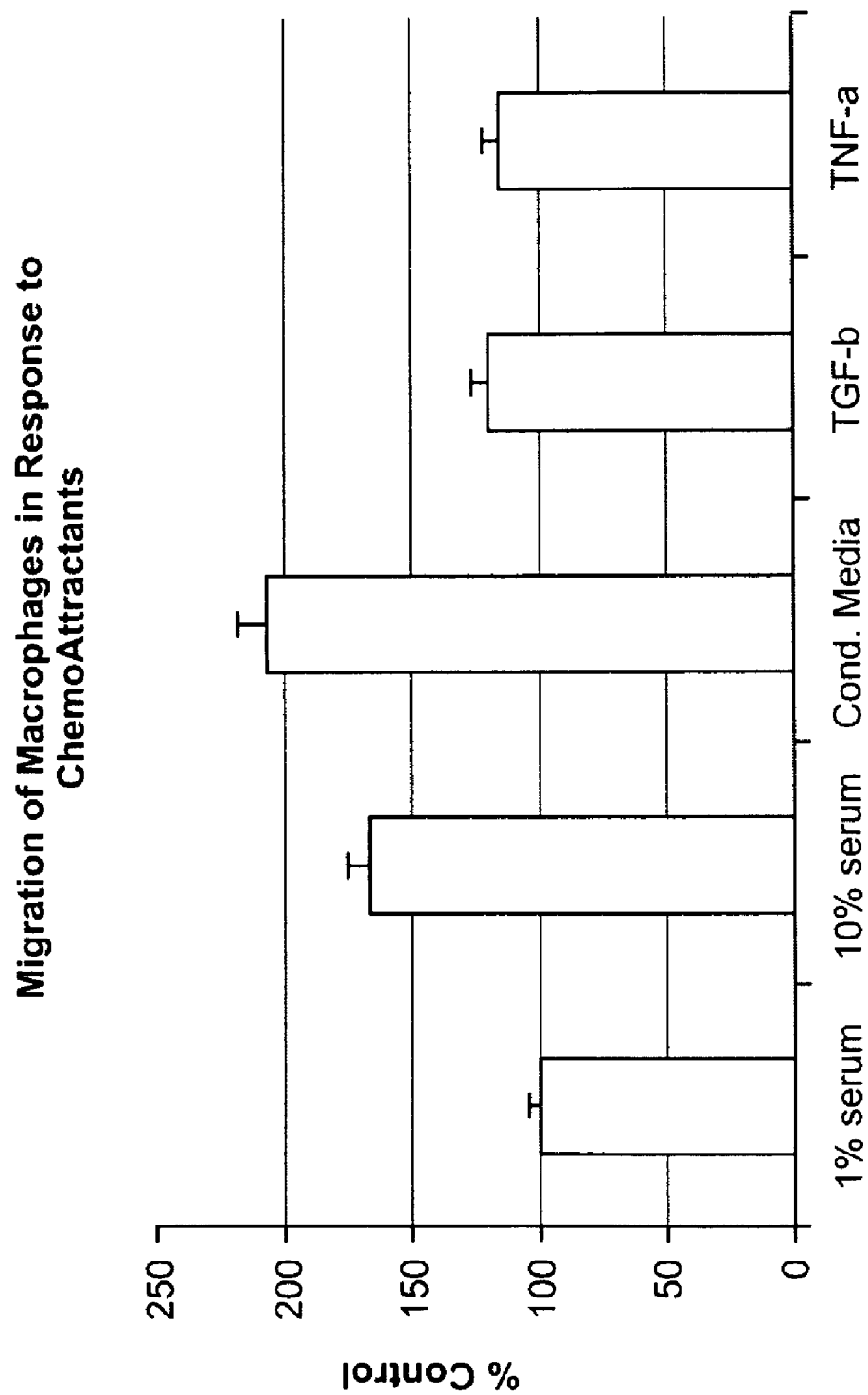
FIG. 14A: Human macrophages migrate in response to chemoattractants in serum and conditioned medium from cultures of RPMI-8226 multiple myeloma cells, TGF-β and TNF-α.
Figure 14B:
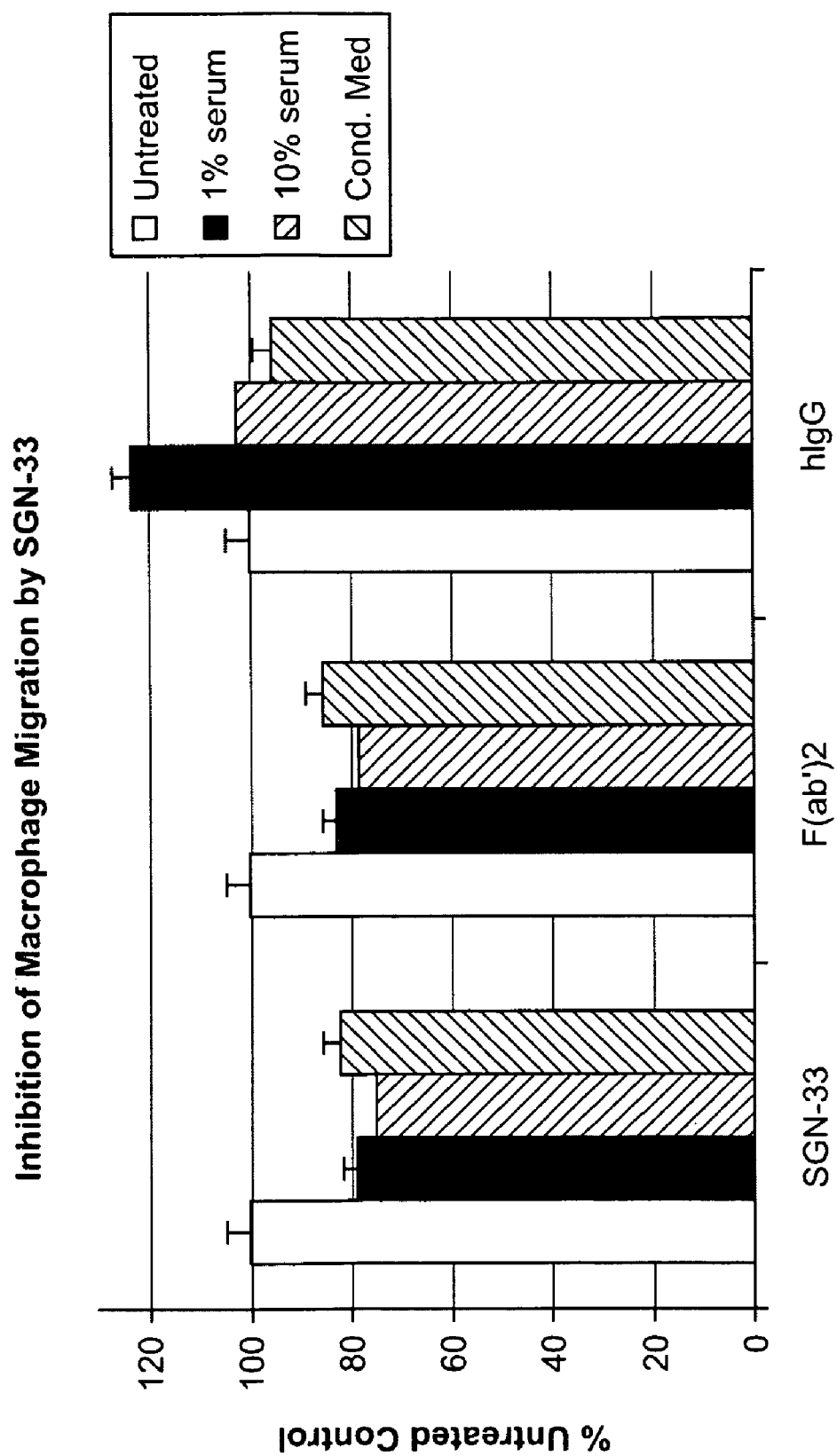
FIG. 14B: SGN-33 or a F(ab')2 fragment of SGN-33 blocks the migration of human macrophages in response to serum or conditioned medium.
Figure 14C:
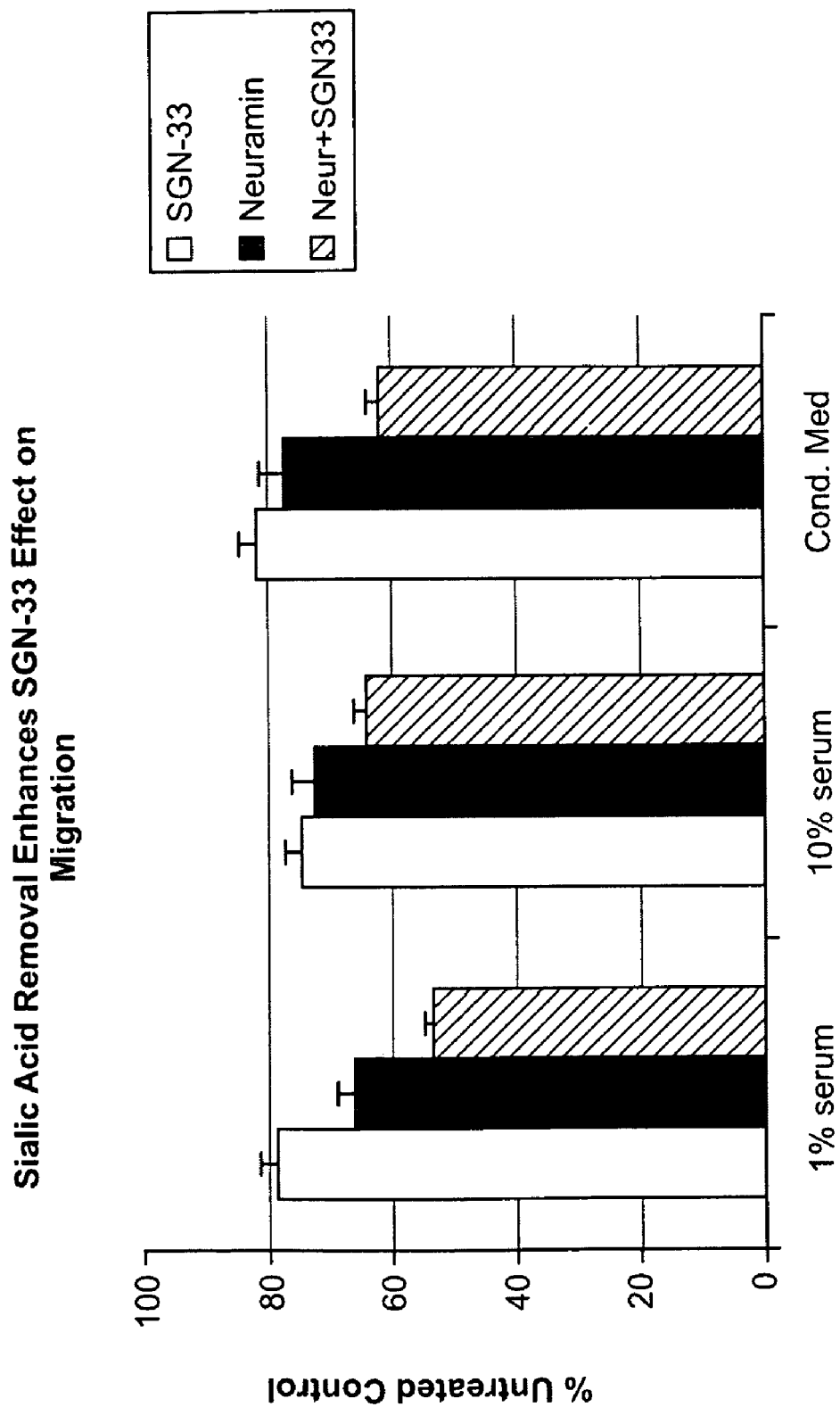
FIG. 14C: Removal of sialic acid with neuraminidase (Neur, Neuramin) enhances the ability of SGN-33 to block migration of human macrophages in response to serum or conditioned medium.

Monocytes and macrophages polarize and move in response to chemoattractants such as cytokines or chemokines. In this study, the effect of SGN-33 on this activity was examined using a commercially available kit. The results are shown in FIG. 14A-14C. Human macrophages were challenged with plating media containing 1% serum, 10% serum, 20% conditioned tumor cell media from cultures of RPMI-8226 multiple myeloma cells, or 50 ng/ml TGF-β, TNF-β, VEGF, or IFN-β. As can be seen in FIG. 14A, more macrophages migrated in the direction of the chemoattractants such as 10% serum or the cytokines compared to cells exposed to 1% serum only. This movement of the macrophages was significantly reduced in cells pre-treated with 25 µg/ml SGN-33 or the F(ab')₂ fragment of SGN-33 (FIG. 14B).

The CD33 molecule recognizes sialic-acid bearing glycans (Freeman et al., 1995, *Blood* 85:2005-2012; Crocker, 2005, *Curr. Opin. Pharm.* 5:431-437). The importance of sialic acid in the inhibitory effect of SGN-33 on the migration of macrophages was examined. Macrophages were incubated with neuraminidase to remove sialic acid bound on the surface of these cells. The cells were then treated with SGN-33 and then challenged with serum or tumor cell conditioned media. As can be seen in FIG. 14C, treatment of the cells with neuraminidase decreased the movement of the macrophages. A greater blocking effect, however, was observed when SGN-33 was added to neuraminidase-treated macrophages. These results show that the effect of SGN-33 on the migration of macrophages is greater in the absence of sialic acid.

These results confirm the importance of SGN-33 in affecting monocyte and macrophage function. By blocking migration and the production of cytokines and chemokines from activated monocytes and macrophages, SGN-33 can modulate the activity of these cells and hence greatly reduce the associated inflammation and tissue destruction. In this manner, SGN-33 will be beneficial in the treatment of inflammatory diseases, cachexia, and tumors that contain infiltrating inflammatory cells (including, for example, cancers of the breast, prostate, bladder, kidney, ovary, endometrium, head and neck, and lung).

Example 6

Anti-CD33 Antibody Decreases Cytokine Production by an AML Cell Line

The KG-1 AML cell line was pre-treated with 2.5 µg/ml SGN-33 or control antibody prior to the addition of 1 ng/ml TNF-alpha. Media was harvested 18 h later for cytokine analyses. SGN-33 reduced the production of IL-8, IP-10, MIP1β, RANTES, and MCP-1 by this AML cell line.

Example 7

Study of the Activity of Anti-CD33 Antibody HuM195

HuM195 was tested in a phase I single-arm dose escalation trial. In prior clinical testing, this anti-CD33 antibody (also referred to as SGN-33 or lintuzumab) induced significant reductions in blast cells in patients with relapsed and refractory acute myeloid leukemia (AML) at low dose with infrequent administration.

This study was initiated to test SGN-33 at higher dose intensity than that previously tested. Entry criteria included CD33 expression on >50% of the marrow blasts to ensure that adequate target antigen was present. Cohorts of 3-6 patients with advanced myeloid malignancies received intravenous SGN-33 at weekly doses of 1.5 to 8 mg/kg for 5 weeks as outpatients. Clinical response was assessed by bone marrow morphology and hematologic improvement. (Inflammatory cytokines and bone marrow monocytes can be tested as correlative studies, as described in Examples 8 and 9, respectively.) Patients demonstrating clinical benefit were eligible for additional every other week outpatient infusions. A total of 31 patients (AML (18), MDS (10), and CMML (3)) with a median age of 75 years (range: 52 to 89) were treated with escalating doses of SGN-33. Among AML patients, 6 had antecedent hematologic disorder. Dosing cohorts included 1.5 (6), 2.5 (4), 4 (4), and 8 mg/kg (17). Dose limiting toxicity has not been observed; the most common drug-related adverse events were chills associated with the first infusion (11/31 patients). Infusion reactions were uncommon during subsequent doses. Among adverse events considered related to antibody, none were Grade 4 and 2 were Grade 3: tumor lysis syndrome documented at 4 mg/kg that resolved swiftly with hydration, and febrile neutropenia observed at 8 mg/kg dose level. No anti-SGN-33 immune responses were detected among the first 15 patients tested. Exposure (AUC) to SGN-33 increased relative to dose and accumulation was documented with repeat dosing. The median time on study was 33 days (range 1-407) and 9 patients have received treatment for more than 56 days.

Among 18 patients with AML, 4 have achieved CR and 1 CR with incomplete platelet recovery. Stable disease was been observed in 6 MDS patients. In summary, SGN-33 has been well tolerated at doses up to 8 mg/kg/wk, achieving serum SGN-33 exposures approximately twenty times higher than in prior studies. Complete remissions were observed in older patients with AML who were not candidates for intensive therapies.

Example 8

Cytokine Measurements in Human Serum Samples

The purpose of this study is to determine the levels of cytokines in human serum samples prior to and following therapy with an anti-CD33 antibody as described in Example 7.

Testing is performed with R & D Systems™ Fluorokine® MultiAnalyte Profiling Multiplex Array using the Luminex® platform (R & D Systems, Inc., Minneapolis, Minn.). Serum samples are collected from patients in the Phase I clinical trial. Assays are performed on an aliquot of the serum to measure the amounts in pg/mL for TNF-α, IFN-γ, IL-6, IL-1β, and IL-10.

Example 9

Measurement of CD33-Positive Cells after Administration of Anti-CD33 Antibody The purpose of this study is to enumerate CD33-positive peripheral blood or bone marrow cells and to assess their level of expression prior to and following therapy with an anti-CD33 antibody as described in Example 7. In addition, the percent saturation of CD33 on bone marrow myeloblasts is determined post-treatment.

Peripheral blood and/or bone marrow samples are collected from patients. Cells are counted using a hematology analyzer for peripheral blood or a flow cytometer for bone marrow. For cell counts between 5,000-10,000 cells/µL, 50 µL of sample is used. For cell counts <5,000 cells/µL, 100 µL of sample is used. For cell counts >10,000 cells/µL, cells are diluted in PBS to be between 5,000-10,000 cells/µL and 50 µL is used.

For each tube:
1. Add 50 or 100 µL specific antibody cocktail to an empty 13×75 mm polystyrene tube.
2. Add 50 or 100 µL peripheral blood or bone marrow specimen, mix gently and incubate 15 minutes at RT in the dark.
3. Add 1.5 mL 0.25% $NH_4Cl$/paraformaldehyde to lyse and fix the cells for 15 minutes at RT in the dark.
4. Centrifuge the tube for 5 minutes at RT at 1700 rpm (550×g), then decant the supernatant.
5. Add 3 mL PBS/BSA/azide to each tube and centrifuge for 5 minutes at RT at 1700 rpm (550×g), then decant the supernatant.
6. Resuspend in 100 µL PBS/BSA/azide.
7. Analyze the cells by flow cytometry using a LSR II Flow Cytometer. 150,000 total white blood cells events are analyzed.

The control tube contains an antibody cocktail including the following monoclonal antibodies: HLA-DR Pacific Blue; CD15 FITC; Ig PE; CD117 PE-Cy5; CD14 PE-Cy7; CD38 Alexa 594; CD34 APC; and CD45 APC-Cy7. The CD33 tube contains an antibody cocktail including the following monoclonal antibodies: HLA-DR Pacific Blue; CD15 FITC; CD33 PE; CD117 PE-Cy5; CD14 PE-Cy7; CD38 Alexa 594; CD34 APC; and CD45 APC-Cy7. All of the monoclonal antibodies are from Becton Dickinson.

Blasts are identified using a combination of CD45 and side scatter gating in combination with CD34, CD117, HLA-DR and CD38, as appropriate. Abnormal promyelocyte and promonocyte populations are identified using CD15 and CD14 in combination with other reagents.

Mean fluorescence intensity (MFI) for the PE detector is obtained for the blast population for control and CD33 tubes. Viability as assessed by forward versus side scatter gating; 80% or greater viability is required for a sample to be scored.

The blast enumeration is provided as percentage of white blood cells (CD45 positive cells) as follows:

% Blasts=(# Blasts/# White blood cells)*100

The % CD33 saturation at each time point following therapy is computed as follows:

% CD33 Saturation=[1−(MFI CD33 test−MFI IgG PE test)/(MFI CD33 diagnosis−MFI IgG PE diagnosis)]*100

Example 10

Effects of Anti-CD33 Antibody on Macrophages and Monocytes

In this study, further evidence that the anti-CD33 antibody affects monocyte and macrophage function is presented.

Primary human macrophages were generated from freshly isolated human PBMCs (AllCells, Emeryville, Calif. or Life-Blood, Memphis, Tenn.) upon long-term culture in X-VIVO- 15 medium (Cambrex, Walkersville, Md.) containing GM-CSF (PeproTech, Rocky Hill, N.J.). Primary human CD14+ monocytes were purchased from Cambrex. The HL-60 promyelocytic leukemia cell line was purchased from ATCC (Manassas, Va.) and grown in RPMI media containing 10% heat-inactivated FCS.

For signaling studies, HL-60 cells, monocytes or macrophages were pre-incubated with the anti-CD33 antibody SGN-33 or deglycosylated SGN-33 for 30 minutes. To prepare deglycosylated SGN-33, the antibody was treated with PN-glycosidase F (New England BioLabs, Ipswich, Mass.). Deglycosylation was confirmed by CE-SDS. Binding of deglycosylated SGN-33 to CD33 was confirmed by ELISA (data not shown). Unlike the intact antibody, the deglycosylated antibody did not mediate effector function, including ADCC or CDC activity (data not shown). Cell lysates were prepared and CD33 immunoprecipitated using an anti-CD33 rabbit polyclonal antibody (Santa Cruz Biotechnology, Santa Cruz, Calif.) prior to SDS PAGE gel electrophoresis. Western blot analyses of these samples were performed using the 4G10 phosphotyrosine antibody (Upstate Biotechnology, Temucula, Calif.), anti-CD33 antibody (NovoCastra, Norwell, Mass.), and anti-SHP-1 antibody (Calbiochem, San Diego, Calif.). Control lysate for SHP-1 was prepared from a B cell lymphoma cell line.

The effects of SGN-33 on cytokine or chemokine production were evaluated as follows: Monocytes or macrophages were pre-treated with SGN-33 for 1 to 2 h in RPMI media containing 10% heat-inactivated human AB serum (Gemini Biopro ducts, West Sacramento, Calif.) prior to challenge with TGF-β (PeproTech), lipopolysaccharide (LPS, Sigma, St. Louis, Mo.) or IFN-γ (PeproTech). Tissue culture media was harvested 18 h later for cytokine analyses by ELISA or Searchlight (Pierce Endogen, Rockville, Ill.).

The migration of macrophages in response to challenge with plating media containing 10% human serum or 20% conditioned tumor cell media was evaluated using the CytoSelect Cell Migration Assay (Cell Biolabs, San Diego, Calif.). Macrophages were treated with SGN-33 or the deglycosylated SGN-33 for 45 minutes prior to plating in RPMI media containing 1% human serum. In some studies, the macrophages were pre-treated with neuraminidase (Sigma) for 1 h prior to incubation with SGN-33. The studies were stopped 18 h later and migration was evaluated after dissociation of the cells from the membrane followed by detection with Cyquant GR dye.

Figure 15:
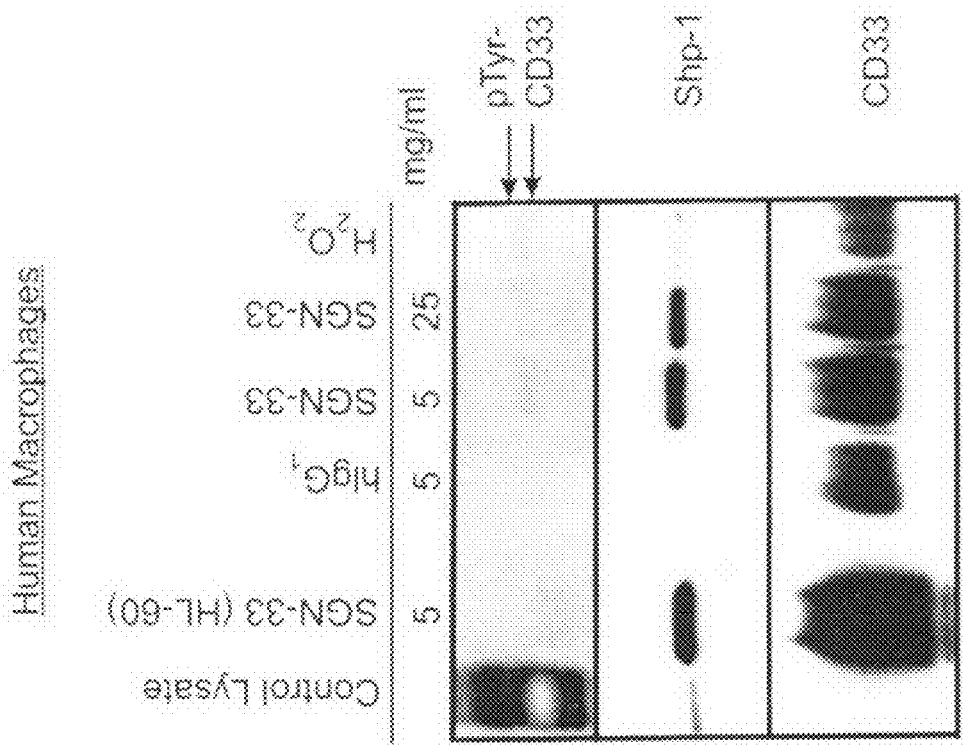
FIG. 15 shows that an anti-CD33 antibody (SGN-33) mediates signaling in AML cells and primary human monocytes and macrophages in a similar fashion. SGN-33 induced phosphorylation of CD33 and recruitment of SHP-1 in AML cells (HL-60) and primary human monocytes and macrophages.
Figure 15:
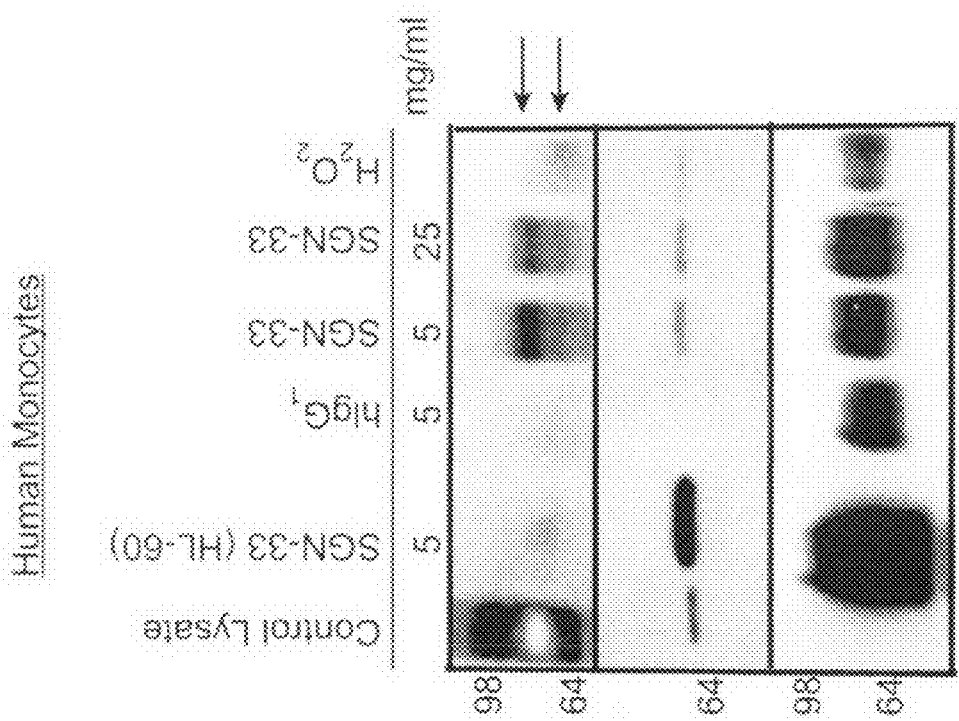

Referring to FIG. 15, the ligation of CD33 by SGN-33 in AML cell lines (HL-60) and primary human monocytes or macrophages resulted in a similar cascade of early signaling events, including phosphorylation of CD33 and recruitment of SHP-1 phosphatase. In this study, HL-60 AML cells and primary human monocytes or macrophages were incubated with soluble SGN-33 for 30 minutes. CD33 was immunoprecipitated from prepared cell lysates and subjected to gel electrophoresis. Western blots were probed with antibodies to pTyr, SHP-1, or CD33. Binding of SGN-33 to CD33 resulted in phosphorylation of CD33 and recruitment of SHP-1. The strength of the phosphorylation response (as ascertained by the strength of signal on western blot) appeared to be stronger in primary monocytes as compared to HL-60 or primary macrophages while the opposite was true for the SHP-1 signal.

Figure 16:
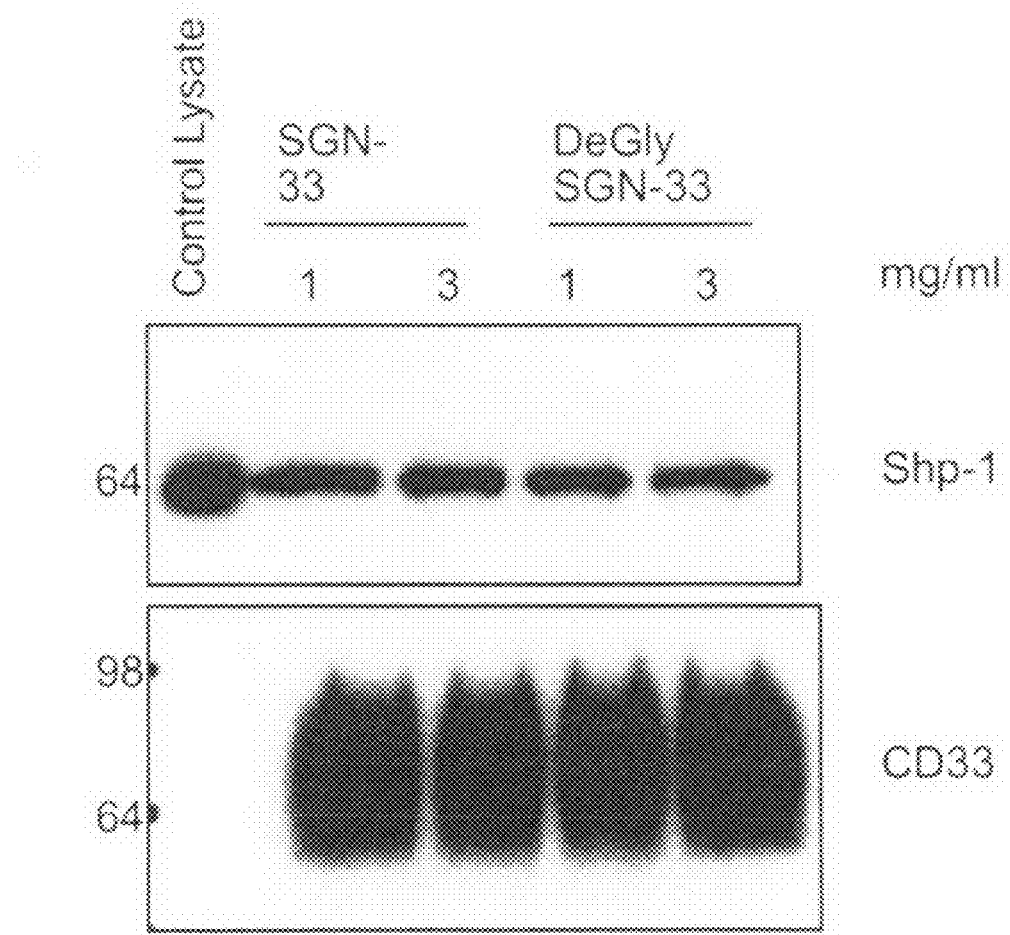
FIG. 16 shows that anti-CD33 antibody (SGN-33 signaling in AML cells is dependent on binding to CD33 and is not affected by changes to Fc receptor interactions. Both SGN-33 and deglycosylated SGN-33 (which does not interact with Fc receptors) induced phosphorylation of CD33 and recruitment of SHP-1 in AML cells (HL-60).

Referring to FIG. 16, HL-60 AML cells were incubated with soluble or deglycosylated SGN-33 for 30 minutes. CD33 was immunoprecipitated from prepared cell lysates and subjected to gel electrophoresis. Western blots were probed with anti-SHP-1 or anti-CD33 antibodies. Binding of SGN-33 or deglycosylated SGN-33 (which does not interact with Fc receptors) to HL-60 and monocytes resulted in recruitment of SHP-1 to the CD33 complex. The pattern of signaling observed with the deglycosylated antibody was similar to that obtained with the intact antibody, indicating that the binding and signaling occurred through CD33 expressed on the surface of the target cells while alterations to Fc receptor binding did not appear to change these responses.

Figure 17:
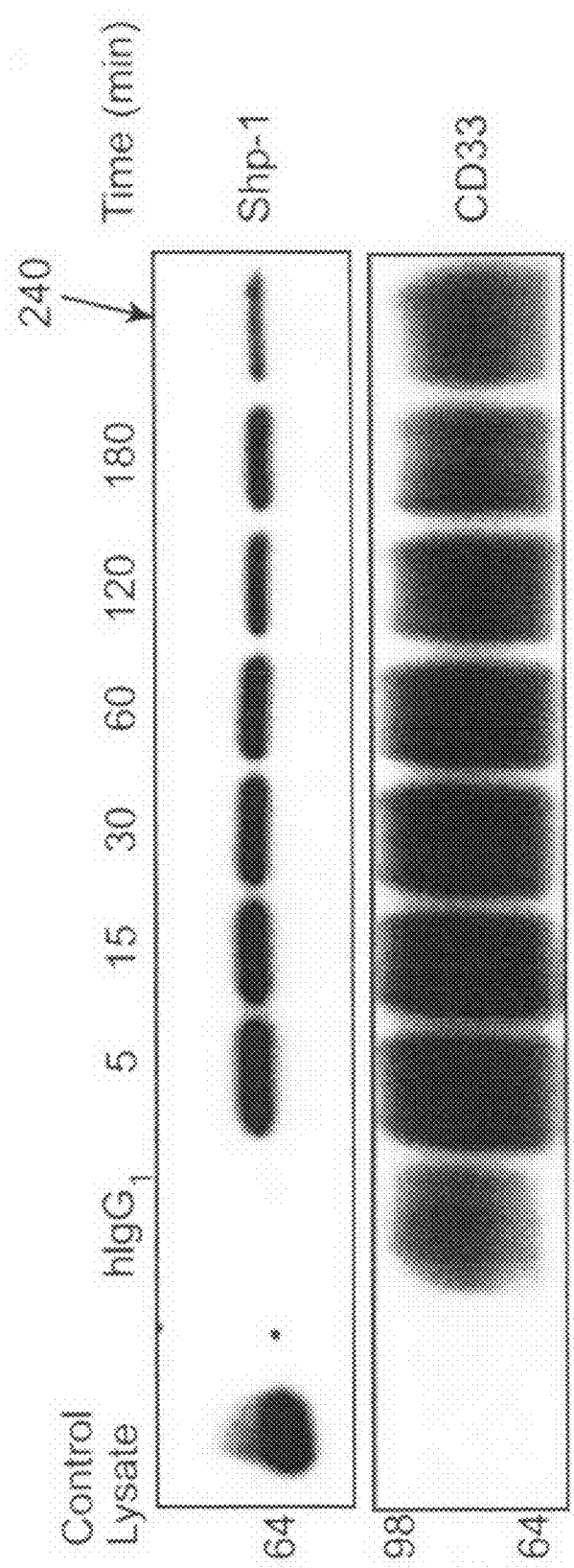
FIG. 17 shows a time course of anti-CD33 (SGN-33) signaling in AML cells. SGN-33 induced phosphorylation of CD33 and recruitment of SHP-1 in AML cells (HL-60) within 5 minutes.

Referring to FIG. 17, HL-60 AML cells were incubated with 3 μg/ml soluble SGN-33 for various times. CD33 was immunoprecipitated from prepared cell lysates and subjected to gel electrophoresis. Western blots were probed with anti-SHP-1 and anti-CD33 antibodies. Binding of SGN-33 to HL-60 resulting in phosphorylation of CD33 and recruitment of SHP-1 occurred within 5 minutes. This signal was stable for 60 minutes before decreasing with time.

Figure 18:
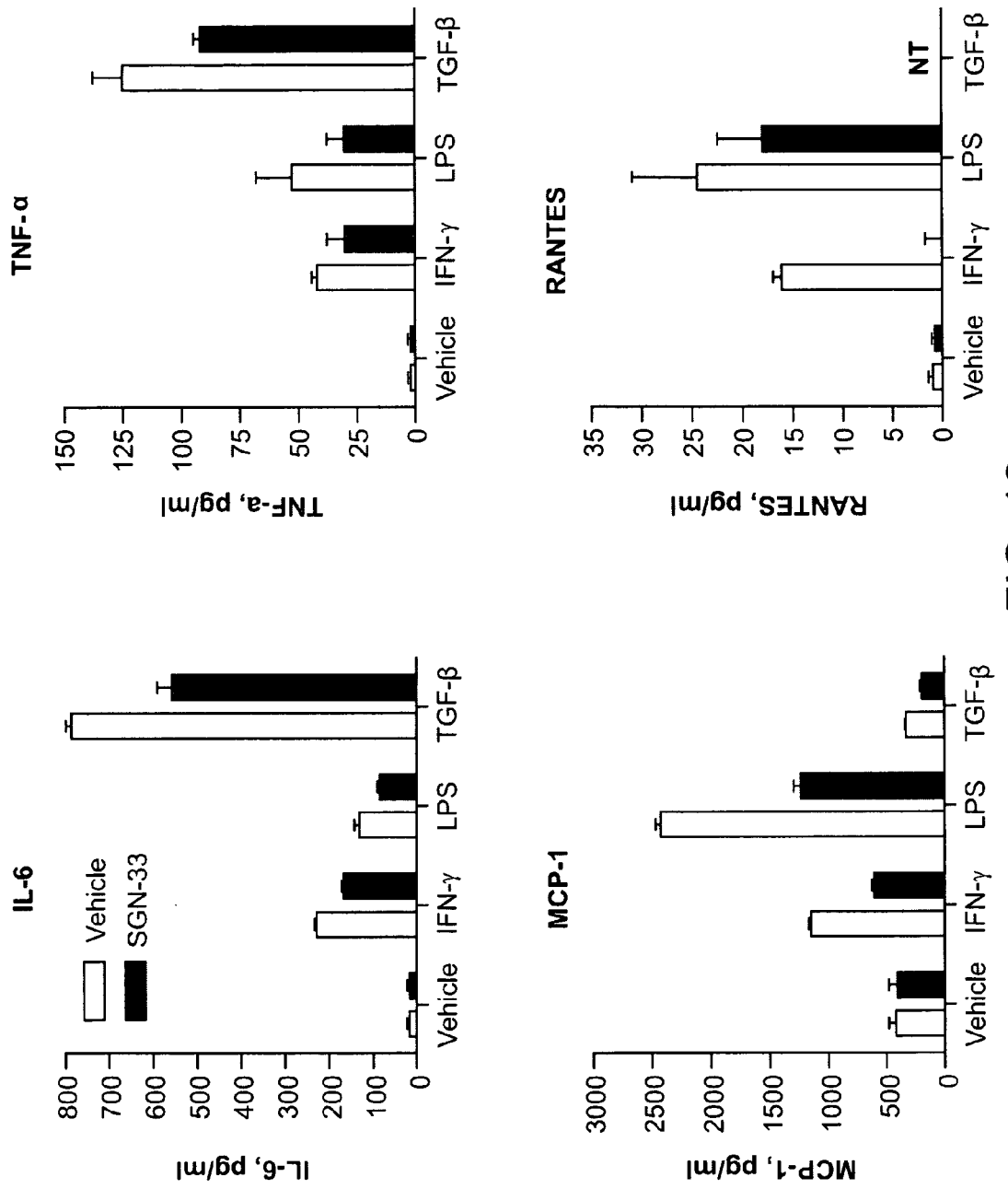
FIG. 18 shows that an anti-CD33 antibody (SGN-33) reduces IFN-γ, LPS, and TGF-β induced production of cytokines IL-6, TNF-α, MCP-1 and RANTES by activated primary human macrophages.

Referring to FIG. 18, the effects of SGN-33 on reducing cytokine and chemokine production by activated primary human macrophages and monocytes were also investigated. Primary human macrophages were treated with SGN-33 in RPMI media containing 10% human serum for 1 h prior to addition of IFN-γ, LPS, or TGF-β. Culture supernatants were collected 18 h later and analyzed for cytokines. When primary human macrophages were challenged with IFN-γ, TGF-β, or LPS, the cells produced significant levels of IL-6, TNF-α, MCP-1, and RANTES. SGN-33 significantly reduced levels of IL-6, TNF-α, MCP-1, and RANTES. (NT=not tested). The production of these factors was reduced by 25 to 95% ($p<0.05$).

Figure 19:
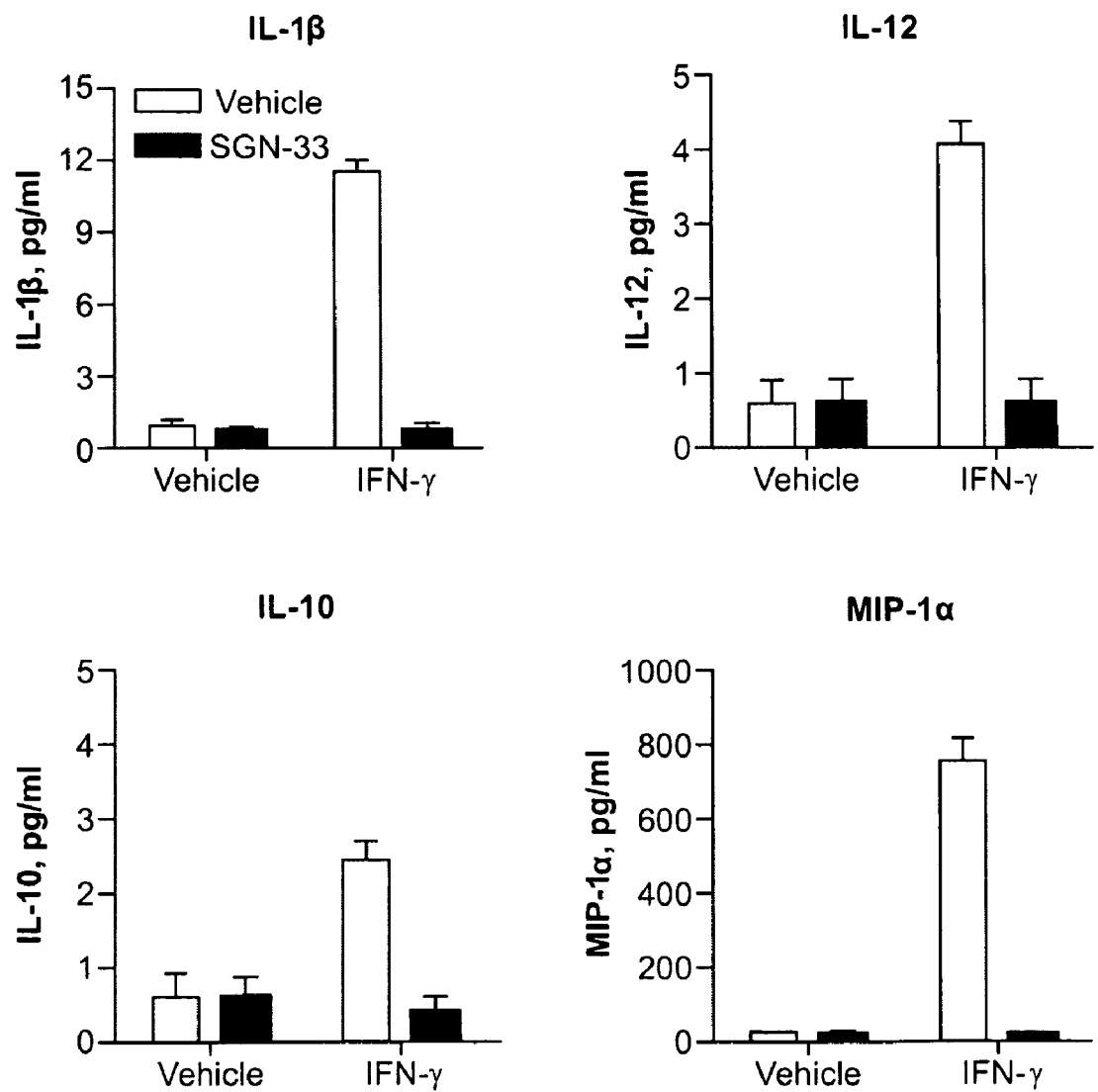
FIG. 19 shows that an anti-CD33 antibody (SGN-33) reduces IFN-γ-induced production of cytokines IL-1β, IL-10, IL-12 and MIP-1α by activated primary human monocytes.

In previous studies, SGN-33 significantly reduced the production of IL-6, TNF-α, MCP-1, IL-8, and RANTES by CD14+ primary human monocytes activated with IFN-γ (see Example 3). Referring to FIG. 19, under similar conditions SGN-33 significantly reduced the IFN-γ-stimulated production of other cytokines, including IL-1β, IL-10, IL-12, and MIP-1α ($p<0.001$). For this study, primary human monocytes were treated with SGN-33 in RPMI media containing 10% human serum for 1 hr prior to addition of IFN-γ. Culture supernatants were collected 18 h later and analyzed for cytokines.

Figure 20:
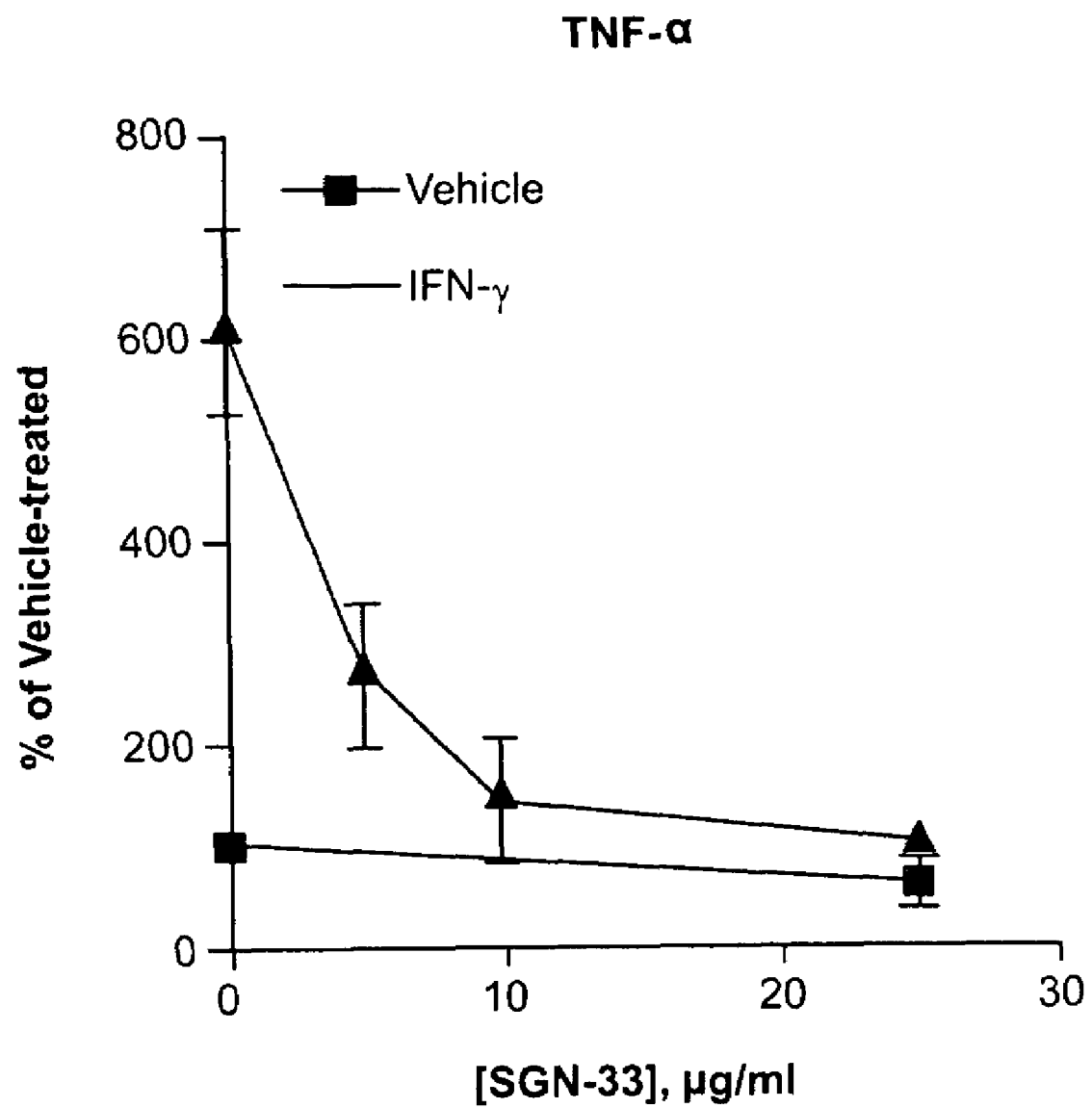
FIG. 20 shows that an anti-CD33 antibody (SGN-33) reduces TNF-α production by IFN-γ stimulated primary human monocytes and macrophages in a dose-dependent manner.

The blocking effect of SGN-33 on cytokine production was dose-dependent, with increasing concentrations of the antibody decreasing cytokine production. Referring to FIG. 20, primary human monocytes or macrophages were treated with various doses of SGN-33 in RPMI media containing 10% human serum for 1 hr prior to addition of IFN-γ. Culture supernatants were collected 18 h later and analyzed for TNF-α. SGN-33 significantly reduced levels of TNF-α in a dose-dependent manner ($p<0.05$). FIG. 20 shows representative data.

Figure 21:
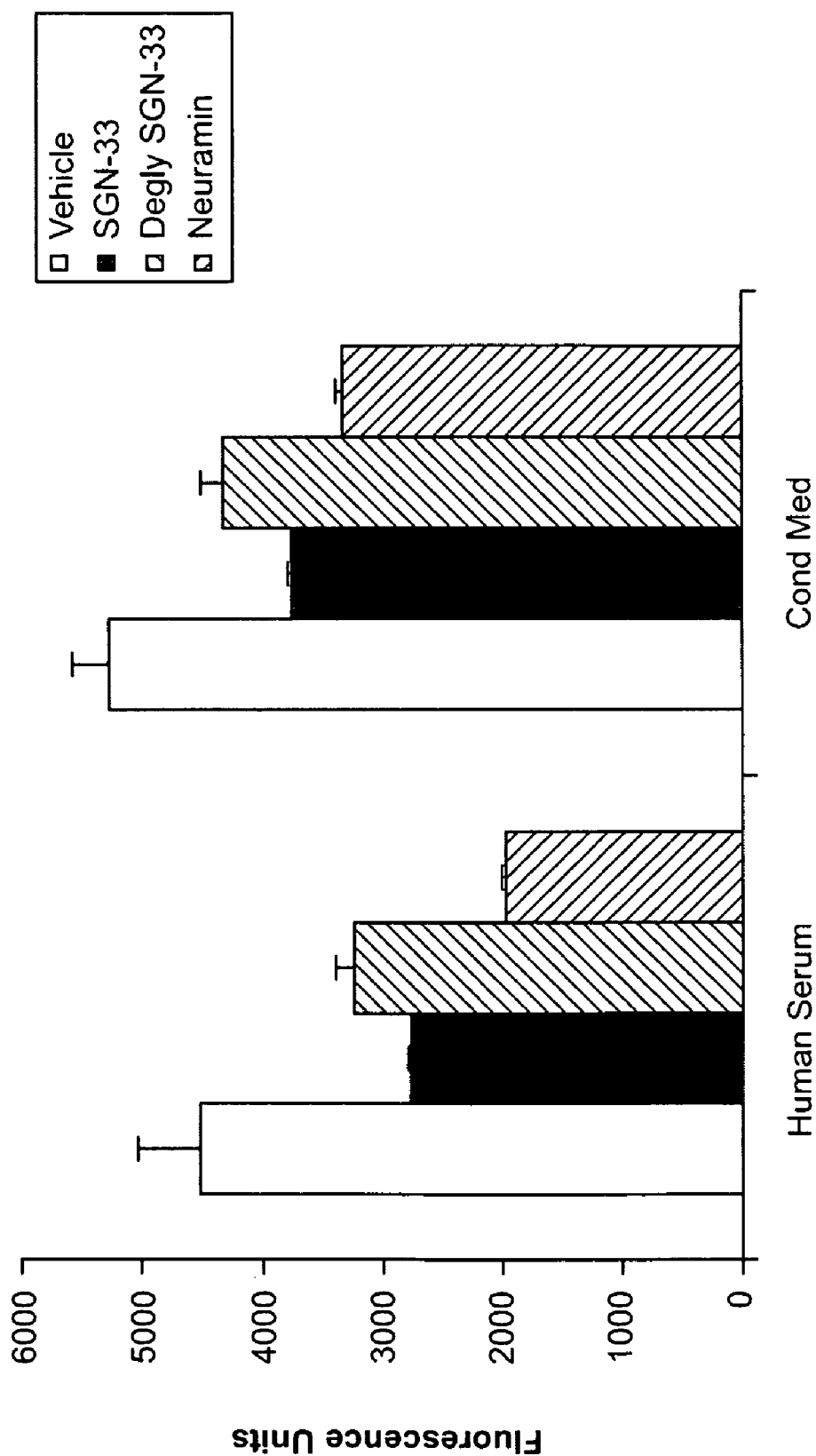
FIG. 21 shows that anti-CD33 antibody (SGN-33) binding to CD33 reduces migration of primary human macrophages in response to human serum or conditioned media from RPMI 8226 multiple myeloma cells. Both SGN-33 and SGN-33 deglycosylated by treatment with neuraminidase significantly reduced the migration of macrophages.

SGN-33 and the F(ab')$_2$ fragment of SGN-33 have also been shown to significantly reduced the movement of primary human macrophages in response to chemoattractants such as human serum. (See Example 5.) In this study, human macrophages were pre-treated with SGN-33 or deglycosylated SGN-33 prior to exposure to human serum or conditioned media from RPMI 8226 multiple myeloma cells. FIG. 21 shows that both SGN-33 and deglycosylated SGN-33 significantly reduced the migration of these macrophages ($p<0.05$), indicating that the blocking effect was mediated through binding to CD33. For this study, primary human macrophages were treated with soluble or deglycosylated SGN-33 in RPMI media containing 1% human serum for 1 hr prior to setting up the transwells. Macrophages were then exposed to RPMI media containing 10% human serum or 20% conditioned tumor cell media. Macrophage migration was quantified using Cyquant GR dye. SGN-33, deglycosylated SGN-33, or neuraminidase (positive control) significantly reduced macrophage migration.

These results confirm the importance of SGN-33 in affecting monocyte and macrophage function. The activation of monocytes and macrophages by LPS, IFN-γ and TGF-β are mediated through described signaling pathways (Ma et al., 2003, Cell Mol. Life. Sci. 60:2334; Andreakos et al., 2004, Immunol Rev. 202:250). The present data suggest that SGN-33 modulates the response of cells to signaling pathways regulated by TGF-β (TGF-β receptors/SMADs), IFN-γ (IFN-γ receptors/JAK/STAT), and LPS (Toll-like receptors 2 and 4/Myd88/TRAF6). As there is a considerable amount of cross-talk amongst the pathways (Fiocchi, 2001, J. Clin. Invest. 108:523, Andreakos et al., 2004, Immunol. Rev. 202: 250), it is contemplated that a molecule like SGN-33 can affect the response of monocytes and macrophages to multiple factors. This regulation may occur by interference at the level of the receptors or at downstream signaling components.

By blocking migration and the production of cytokines and chemokines from activated monocytes and macrophages, SGN-33 can modulate the activity of these cells and hence greatly reduce the associated changes in immune function such as those found in advanced cancers and inflammatory diseases.

Example 11

Treatment of Elderly AML Patients with Anti-CD33 Antibody and Low Dose Cytarabine A randomized, double-blinded, placebo-controlled, parallel group trial is conducted to evaluate overall survival in older patients with AML. Patients have morphologically confirmed AML demonstrating at least 20% blasts in the bone marrow, are at least 60 years of age, and have an ECOG performance status from 0 to 2. After informed consent, patients have declined intensive chemotherapy. The presence of chronic medical comorbidities including non-hematologic chronic malignancies (e.g. breast, prostate, or colon carcinoma) is generally acceptable.

The patients are evaluated for a survival benefit of a combination treatment with low dose cytarabine and SGN-33. The patients are randomized in a 1:1 ratio into two treatment groups. One treatment group receives low dose cytarabine in combination with SGN-33 and the other treatment group receives low dose cytarabine in combination with placebo. Patients receive cytarabine 20 mg twice daily subcutaneously (SC) for 10 consecutive days every 4 weeks, and lintuzumab (1.5-8 mg/kg/dose) or placebo IV once weekly for 4 weeks then once every other week lintuzumab 1.5-8 mg/kg/dose or placebo until off study due to death or discontinuation of therapy. Each cytarabine treatment cycle is targeted to occur at 4 week intervals and cycles will be administered until a decision is made to initiate an alternative anti-leukemic treatment, patient preference, unacceptable toxicity, or death from any cause.

Study assessments will include overall survival, hospitalizations, infections, transfusion support, QOL assessments, adverse events, clinical laboratory values, vital signs and physical findings.

Example 12

Anti-CD33 Antibody Combined with Cytarabine Improves Survival in an AML Model

Figure 22:
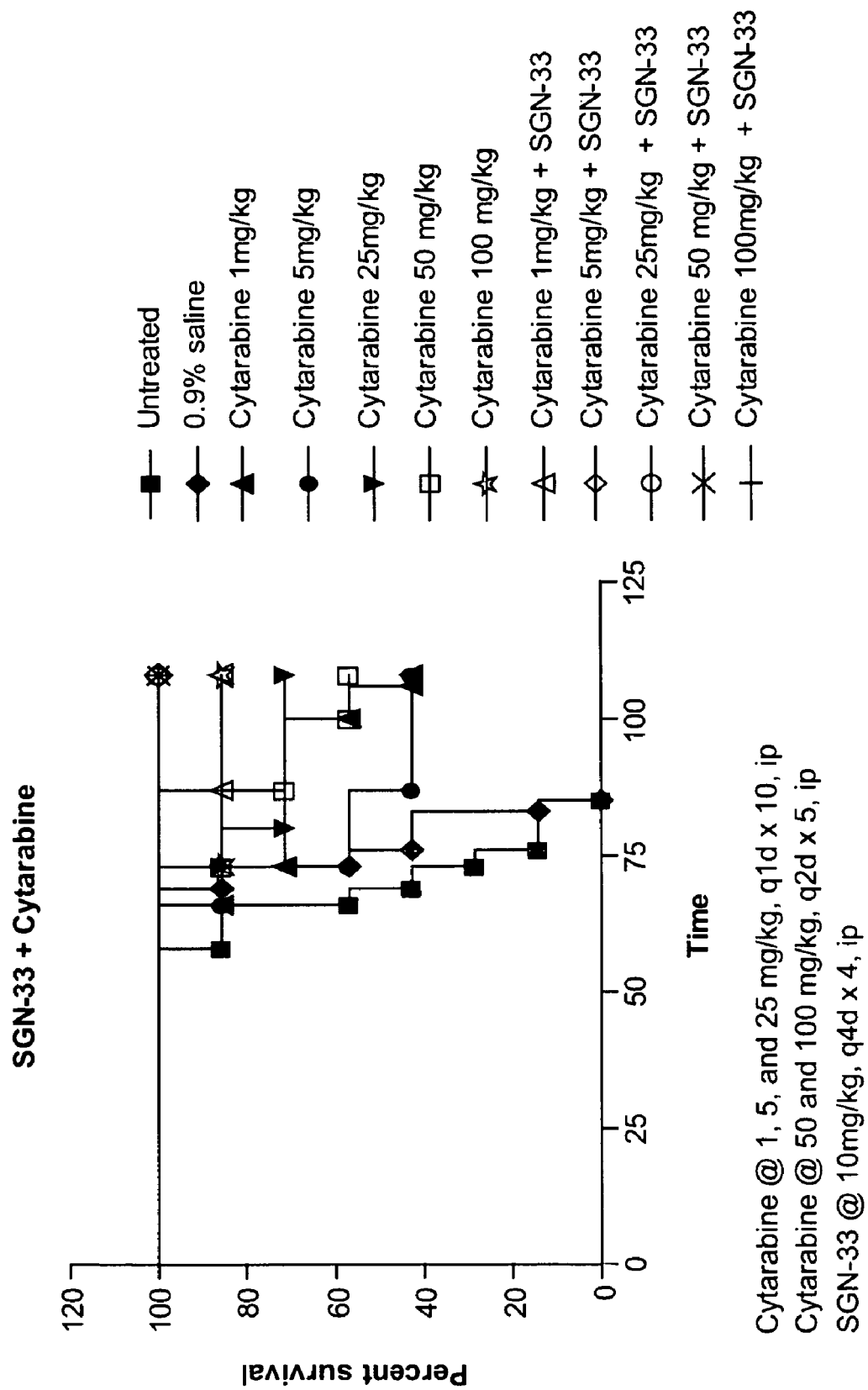
FIG. 22 shows that combining an anti-CD33 antibody (SGN-33) with cytarabine increases the survival of mice in a mouse AML model.

Mice were implanted with an AML cell line, HL-60, as follows: 5 million HL-60 cells were injected intravenously. The mice were treated with lintuzumab (10 mg/kg, q4dx4, ip), cytarabine (1 mg/kg, 5 mg/kg or 25 mg/kg, q1dx10, ip; or 50 mg/kg or 100 mg/kg, q2dx5, ip) or lintuzumab with cytarabine (dosed as described previously). Treatment began on day one. Referring to FIG. 22, the control mice or mice treated with placebo (0.9% saline) were removed from the study by day 80, due to tumor progression. Mice treated with low doses of cytarabine alone had increasing percent survival rates, as compared to the untreated controls. When lintuzumab was added to the treatment regimen, the mice exhibited 80% survival (1 mg/kg cytarabine) or greater (5 mg/kg or higher doses of cytarabine).

Example 13

Anti-CD33 Mediated ADCC is Enhanced by Lenalidomide

Figure 23:
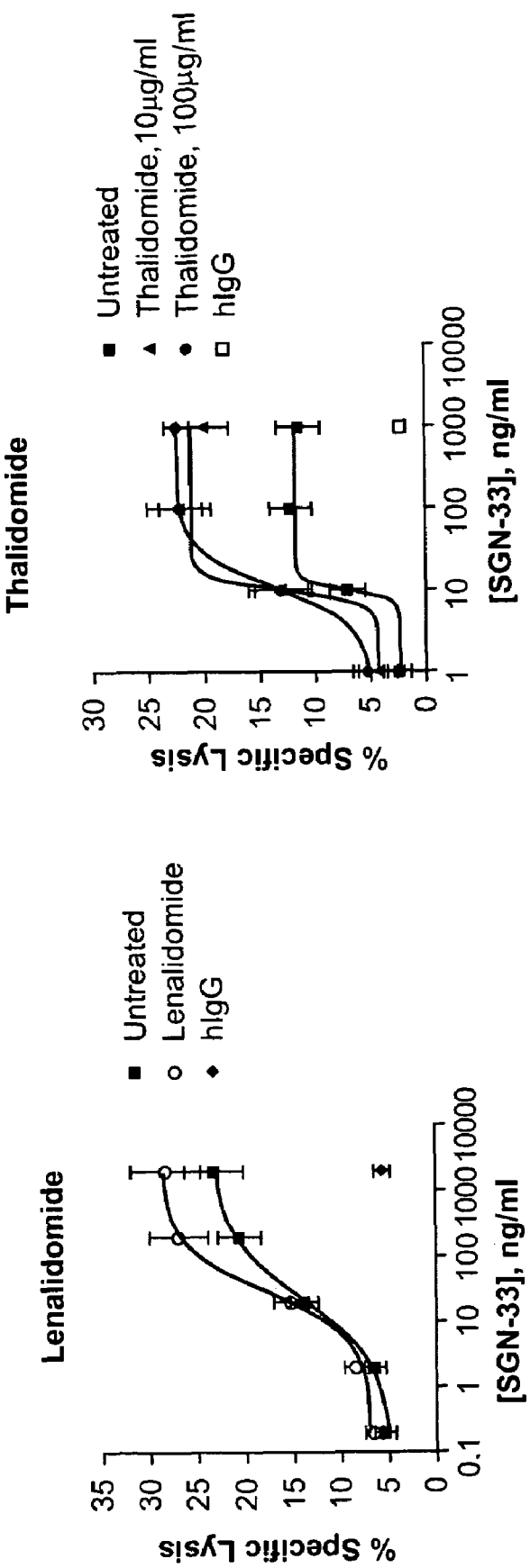
FIG. 23 shows the effects of lenalidomide or thalidomide can increase the ADCC activity of an SGN-33 antibody.

The ADCC activity of SGN-33 was measured using a standard $^{51}$Cr release assay. Viable NK cells were pre-treated for 2 to 3 h with lenalidomide or thalidomide (as described in FIG. 23) prior to addition to target cells. Referring to FIG. 23, the data show that lenalidomide or thalidomide enhanced SGN-33 mediated ADCC.

Figure 24:
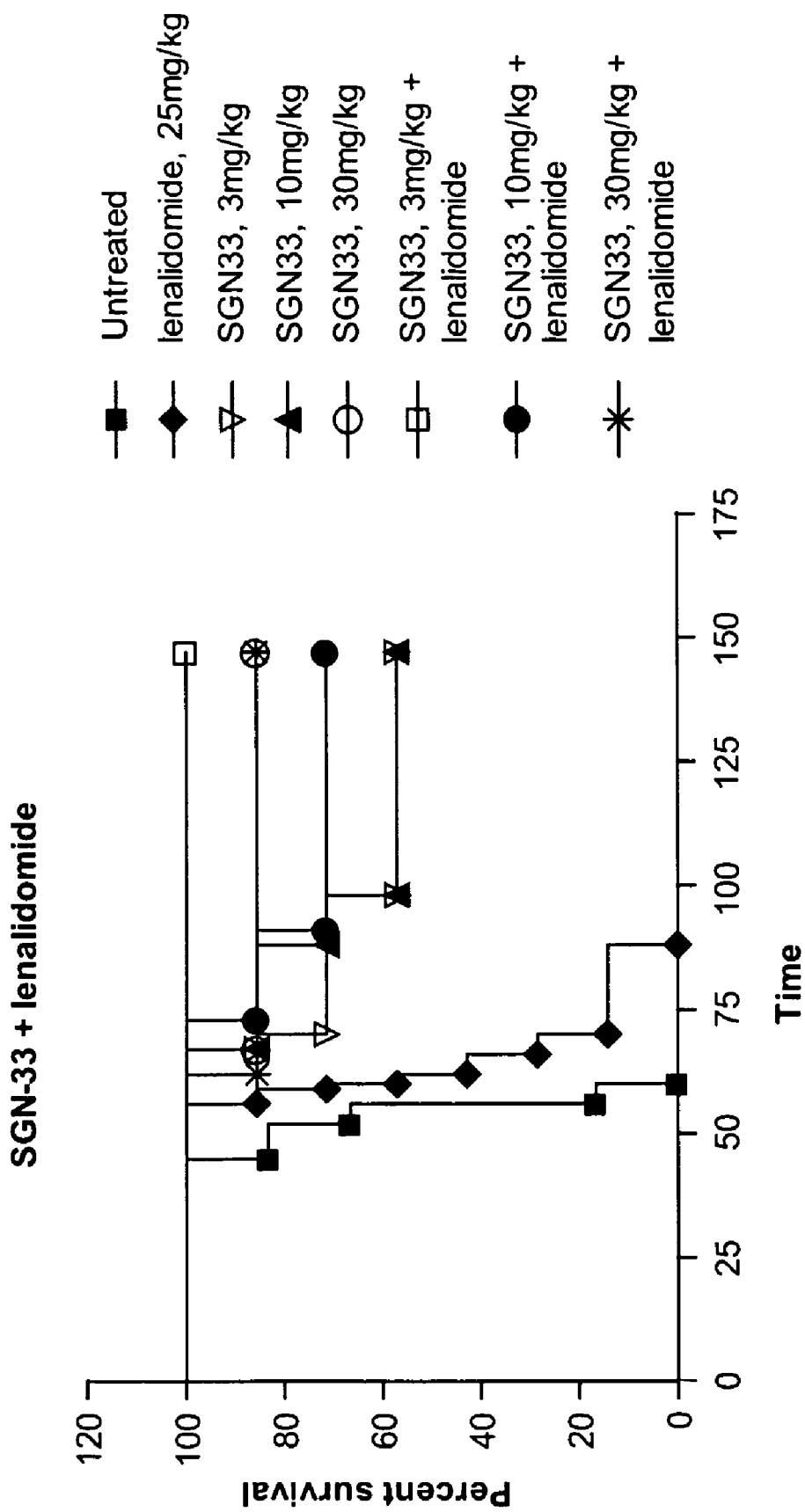
FIG. 24 shows that combining an anti-CD33 antibody (SGN-33) with lenalidomide increases survival of mice in a mouse AML model.

To confirm the data of the in vitro study, mice were implanted with an AML cell line, HL-60, as follows: 5 million HL-60 cells were injected intravenously. The mice were treated with SGN-33 (3, 10 or 30 mg/kg, q4dx5, ip), lenalidomide (25 mg/kg, qdx3, ip) or a combination SGN-33 and lenalidomide (as described). Treatment began on day one. Referring to FIG. 24, the control mice were removed from the study by about day 60 due to tumor progression. Mice treated with lenalidomide were removed from study by about day 90 for similar reasons. In contrast, mice treated with SGN-33 (3 or 10 mg/kg) exhibited about a 50% survival rate while 30 mg/kg yielded a survival rate of ~85%. Mice treated with the combination of SGN-33 and lenalidomide appeared to exhibit about 100% survival in this study.

Example 14

SGN-33 is Efficacious in Disseminated Models of Multi-Drug Resistant AML

This example describes the in vivo antitumor efficacy of the anti-CD33 antibody SGN-33 in xenograft models of disseminated AML in SCID mice, including tumors displaying multi-drug resistance (MDR).

As a preliminary step, the AML cell lines HL60, KG-1, HEL9217 and TF1-α were assessed for multi-drug resistance (MDR) status and CD33 copy number. MDR status was determined by flow cytometry assessment of Rhodamine (Rh123) efflux at 37° C. MDR negative cells such as HL60 did not pump out Rh123. CD33 copy number was determined by qFACs (DAKO QifiKit) and apparent Kd values by saturation binding measurements using flow cytometry. Table II below summarizes the MDR status and CD33 copy number of all four cell lines.

TABLE II

| Cell Line | CD33 # | MDR Status | kd (pM) for SGN-33 |
|---|---|---|---|
| HL60 | 13000 | Negative | 123 ± 16 |
| KG-1 | 12600 | Negative | 70 ± 20 |
| HEL9217 | 20000 | Positive | 144 ± 12 |
| TF1-α | 6500 | Positive | 99 ± 22 |

Figure 25:
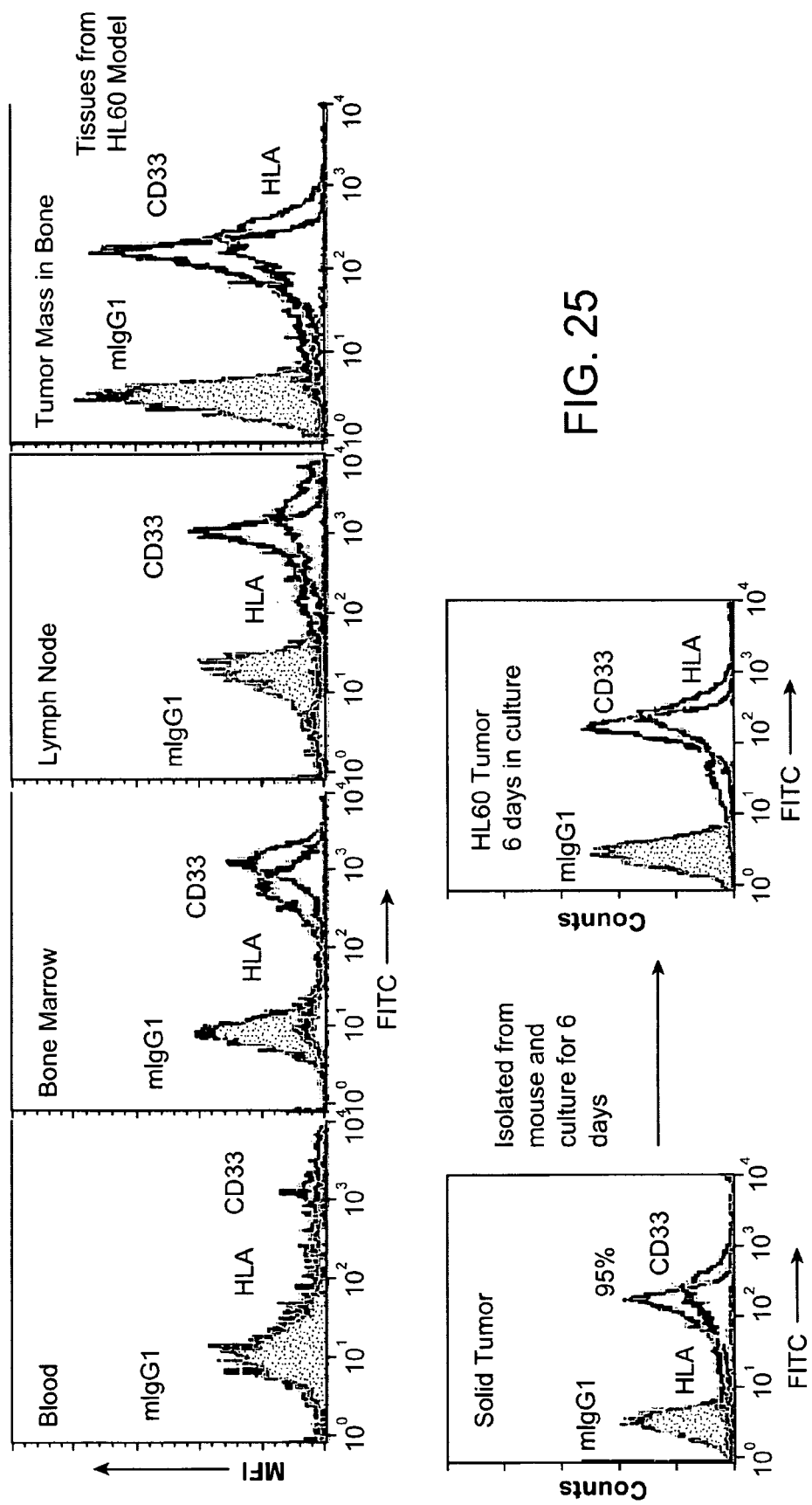
FIG. 25 shows the presence (by flow cytometry) of human CD33+ tumor cells in the blood, bone marrow, and lymph nodes in mice injected with human CD33+ HL60 cells. Blood and tissue samples were harvested from mice inoculated with HL60 cells and processed for flow cytometry to assess the presence of human AML cells (top panels). Human cells were detected in the mouse tissue samples with labeled anti-CD33 and anti-MHC I (HLA-A,B,C) commercial antibodies. Human AML tumor cells were found in the blood, bone marrow, lymph node and in solid tumors of all 3 mouse models. When tumor masses were placed in culture, the expression of CD33 was maintained after 6 days (bottom panels).
Figure 26A:
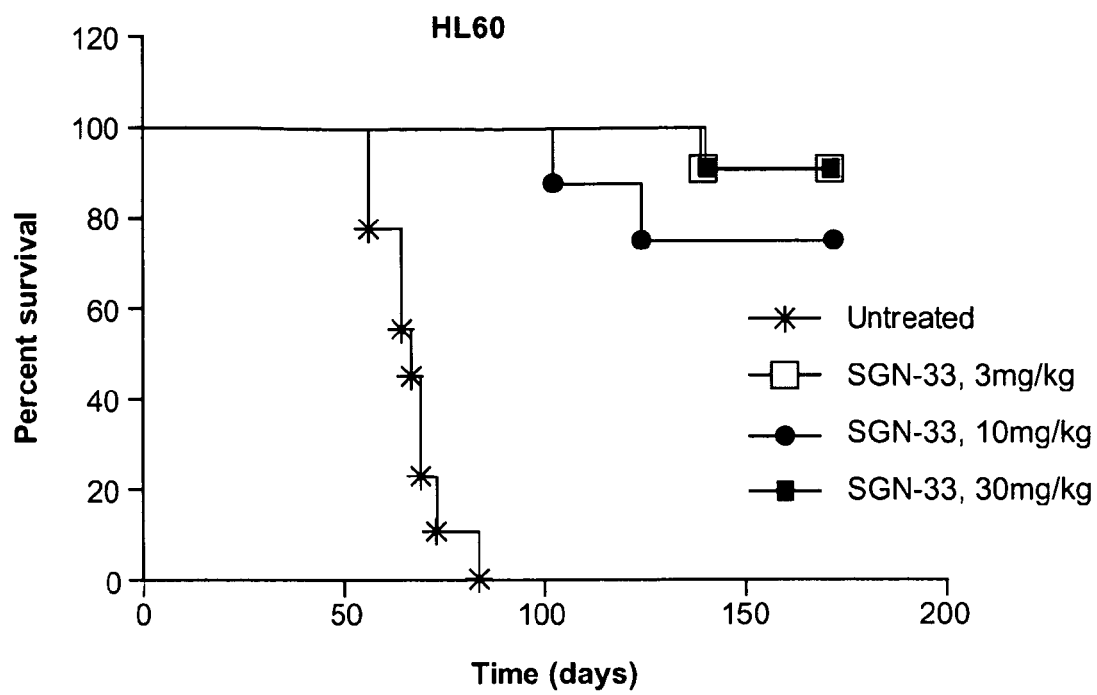
FIGS. 26 (26A, 26B and 26C) shows enhanced survival and/or reduced tumor burden in mice treated with SGN-33 in the HL60, HEL-9217 and TF1-α models of disseminated AML. (A) HL-60 model. (B) TF1-α model. (C) HEL-9217 model.
Figure 26B:
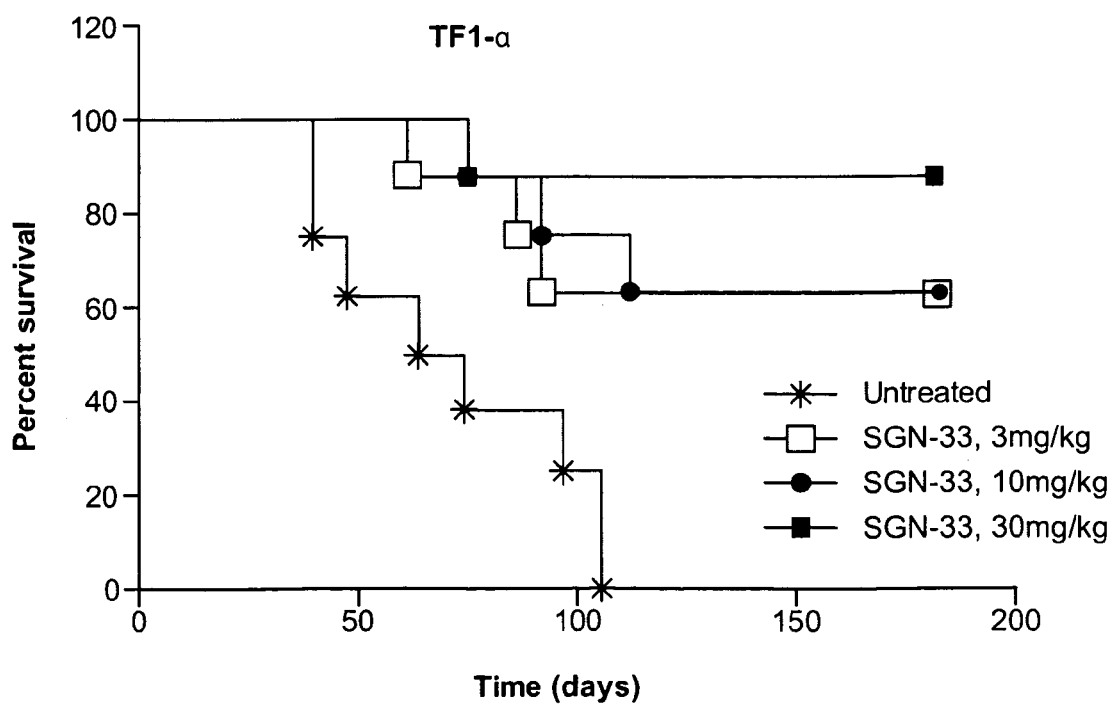
Figure 26C:
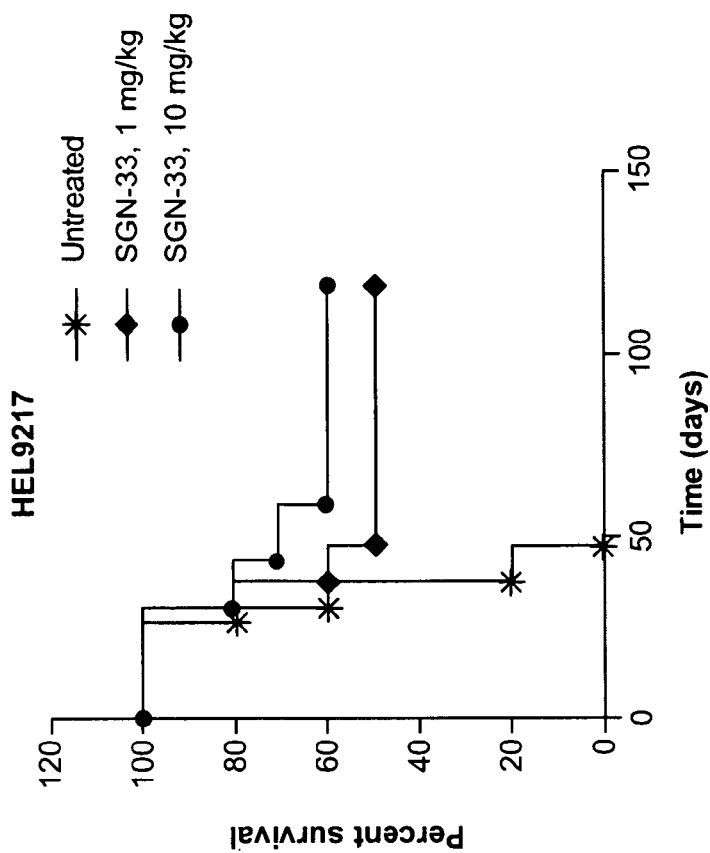
Figure 26C:
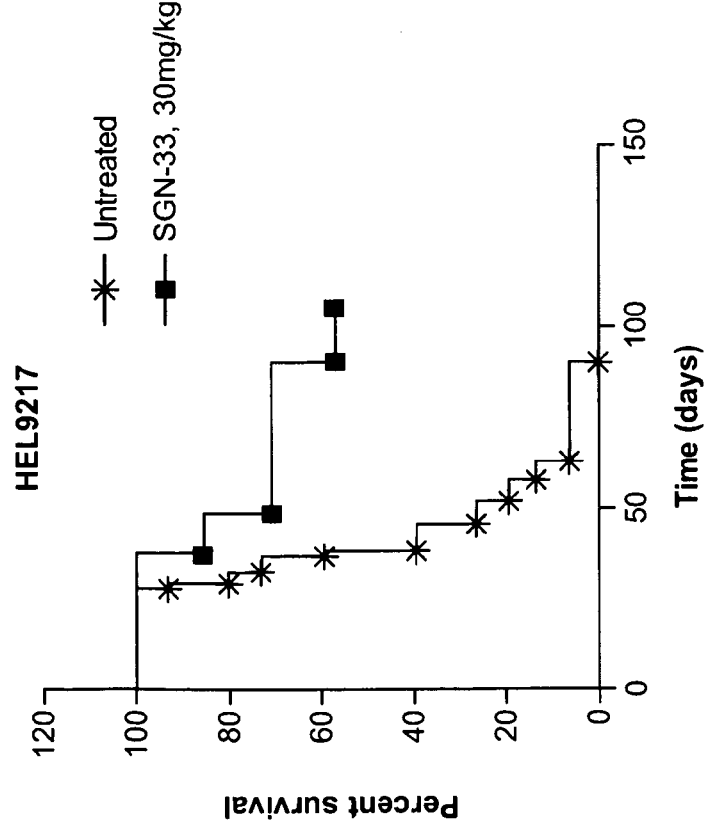
Figure 27A:
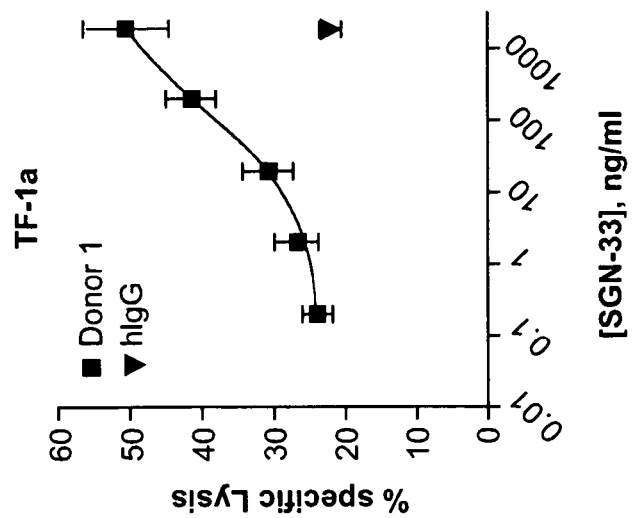
FIGS. 27 (27A, 27B and 27C) shows SGN-33 mechanisms of action on various MDR-positive and MDR-negative cells. (A) SGN-33 mediated ADCC activity. Target AML tumor cells (KG-1 HEL9217, and TF1α) were labeled with $Na^{51}CrO_4$ and mixed with enriched CD16+ effector (NK) cells, prepared using PBMCs from normal donors. The effector to target cell ratio was 10:1. The figure shows results obtained using NK cells from 2 different donors. SGN-33 was seen to mediate cell lysis of MDR− and MDR+ AML tumor cell lines. (B) SGN-33 enhanced ADCP activity. Target AML tumor cells were labeled with the lipophilic PKH67 dye, treated with SGN-33 or hIgG, and then mixed with monocyte-derived macrophages. Macrophages were labeled with CD11b-FITC or CD14-FITC antibody. Flow cytometric analyses of dual labeled (PKH67+CD11b+ or PKH67+CD14+) cells was used to determine specific uptake (phagocytosis). SGN-33 was seen to mediate phagocytosis of AML tumor cells. (C) SGN-33 mediated cytokine reduction. AML cells were pretreated with 10 μg/ml SGN-33 prior to challenge with 1 ng/ml TNF-α. Media were collected 18 h later and analyzed by ELISA for IL-8 or MCP-1. SGN-33 significantly reduced the production of cytokines by AML tumor cell lines ($*p<0.05$, $**p<0.01$).
Figure 27A:
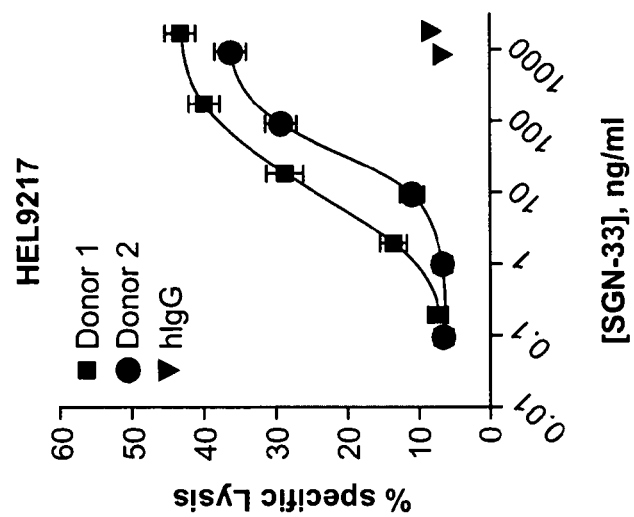
Figure 27A:
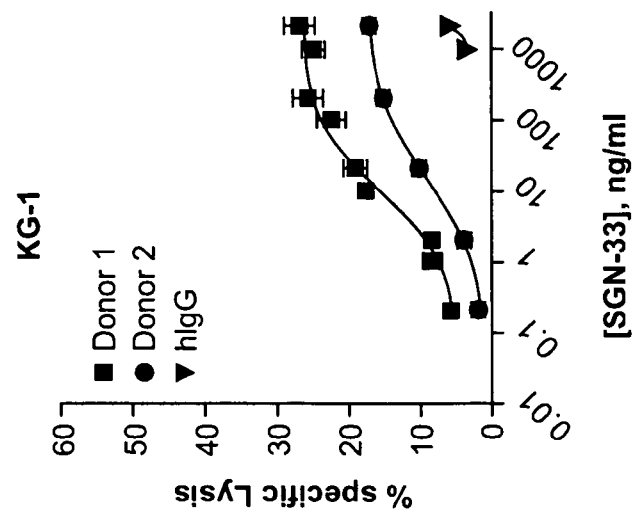
Figure 27B:
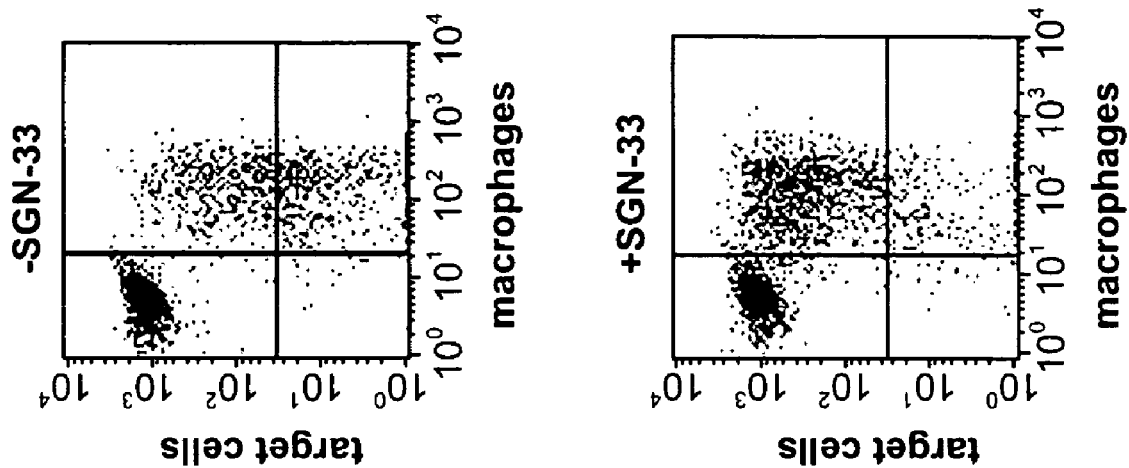
Figure 27B:
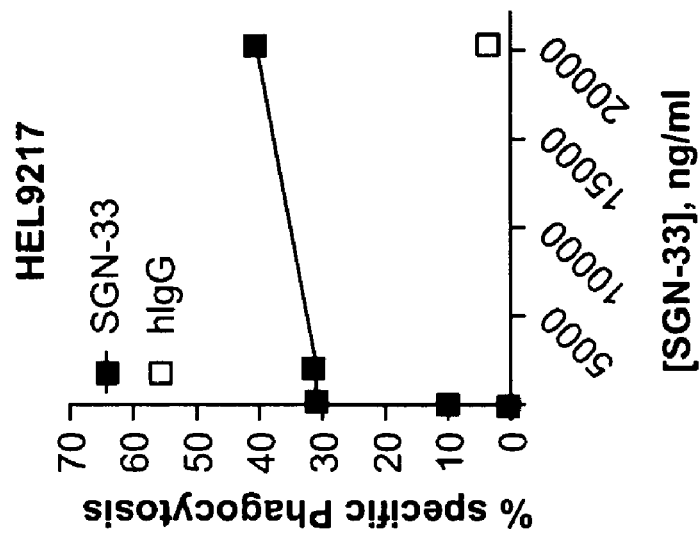
Figure 27B:
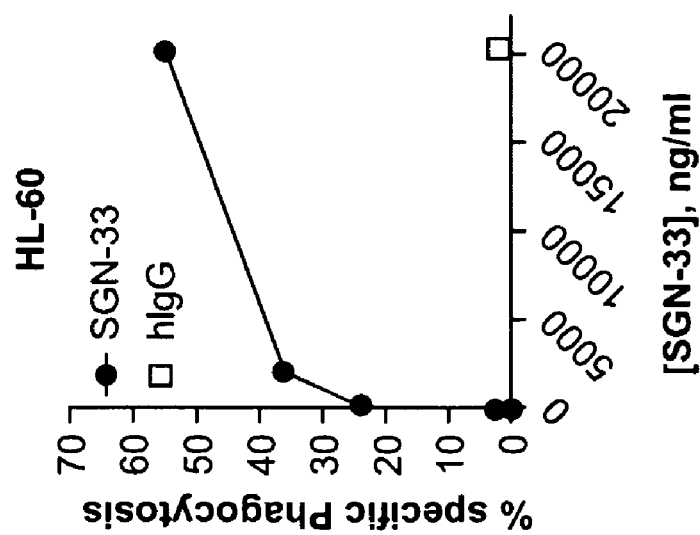
Figure 27C:
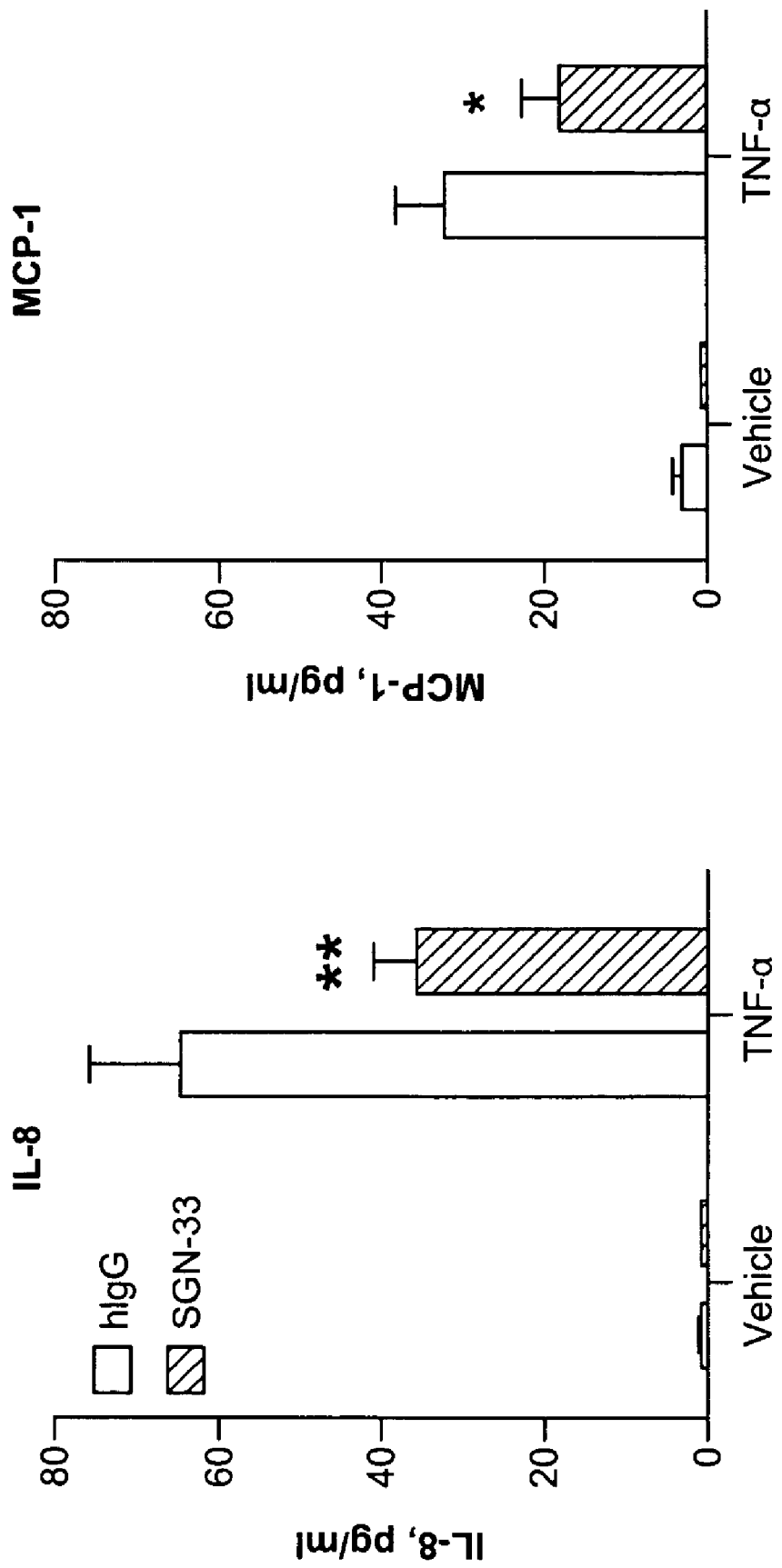

To study the in vivo efficacy of SGN-33, disseminated models of MDR-positive and MDR-negative AML were established in female SCID mice. The MDR-negative HL60 cell line and the MDR-positive HEL9217 and TF1-α cell lines were used. Mice were injected with 5 million AML cells and dosed q4dx4 with SGN-33 the next day. The mice were monitored for signs of disease and euthanized once symptoms were displayed. Disease symptoms typically developed between about 35 and about 80 days, and included hind limb paralysis, scruffy coat, weight loss, palpable tumors, and/or tumor masses in bone, peritoneal cavity, or soft tissues. Human CD33+ tumor cells were detected in the blood, bone marrow, and lymph nodes of the majority of the mice by flow cytometry (FIG. 25). Solid tumors associated with bone or soft tissues were found in 20 to 60% of the mice.

As seen in FIG. 26, SGN-33 enhanced the survival and/or reduced tumor burden of the mice in the HL60 and TF1-α models (>100 days, p<0.005) and HEL9217 model (>80 days, p<0.005). In the MDR-negative HL60 model, SGN-33 from 3 to 30 mg/kg significantly increased the survival of mice by greater than 100 days (p<0.0001). In the MDR-positive HEL9217 or TF1-α models, 4 doses of SGN-33 at 10 or 30 mg/kg significantly increased the survival of these mice by greater than 40 days (p<0.025).

The mechanisms of action of SGN-33 against MDR-positive and MDR-negative cells were examined in vitro. As shown in FIG. 27, SGN-33 mediated antibody-dependent cell cytotoxity (in terms of cell lysis) and antibody-dependent cell phagocytosis of MDR-positive and MDR-negative AML cells and reduced cytokine production in these cells.

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents (patents, published patent applications, and unpublished patent applications) is not intended as an admission that any such document is pertinent prior art, nor does it constitute any admission as to the contents or date of the same. The invention having now been described by way of written description, those of skill in the art will recognize that the invention can be practiced in a variety of embodiments and that the foregoing description is for purposes of illustration and not limitation of the following claims.

What is claimed is:

1. A method of treating a patient having acute myeloid leukemia (AML) or myelodysplastic syndromes (MDS), comprising administering an unconjugated humanized M195 antibody to the patient at a dose of 1.5 to about 12 mg/kg body weight, whereby progression of the AML or MDS is inhibited, and wherein the AML is resistant to chemotherapy.

2. The method of claim 1, wherein the AML is multidrug resistant.

3. A method of treating a patient having AML or MDS, comprising administering an unconjugated humanized M195 antibody to the patient at a dose of 1.5 to about 12 mg/kg body weight, whereby progression of the AML or MDS is inhibited, and wherein the humanized M195 antibody is administered in combination with at least one chemotherapeutic agent effective against cancer.

4. The method of claim 3, wherein the chemotherapeutic agent is Velcade® (bortezomib), Revlimid® (lenalidomide), Vidaza® (azacytidine), Dacogen® (Decitabine) or cytarabine.

5. The method of claim 4, wherein the chemotherapeutic agent is Revlimid® (lenalidomide).

6. The method of claim 4, wherein the chemotherapeutic agent is Vidaza® (azacytidine).

7. The method of claim 4, wherein the chemotherapeutic agent is cytarabine.

8. A method of treating a patient having AML or MDS, comprising administering an unconjugated humanized M195 antibody to the patient at a dose of 1.5 to about 12 mg/kg body weight, whereby progression of the AML or MDS is inhibited, and wherein the AML or MDS is CD33-negative.

9. A method of treating a patient having AML or MDS, comprising administering an unconjugated humanized M195 antibody to the patient at a dose of 1.5 to about 12 mg/kg body weight,
whereby progression of the AML or MDS is inhibited,
wherein the humanized M195 antibody decreases the number of involved non-malignant effector cells, and/or decreases the levels of one or more inflammatory cytokines, chemokines or growth factors, in the patient, and
the method further comprises monitoring the levels of one or more inflammatory cytokines, chemokines or growth factors in the patient.

10. The method of claim 9, wherein the one or more inflammatory cytokines, chemokines or growth factors are interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10, macrophage inflammatory protein 1α (MIP1α) and/or macrophage inflammatory protein 1β (MIP1β).

11. A method of treating a patient having AML or MDS, comprising administering an unconjugated humanized M195 antibody to the patient at a dose of 1.5 to about 12 mg/kg body weight,
whereby progression of the AML or MDS is inhibited,
wherein the humanized M195 antibody decreases the number of involved non-malignant effector cells, and/or decreases the levels of one or more inflammatory cytokines, chemokines or growth factors, in the patient, and
the method further comprises monitoring the number of involved non-malignant effector cells in the patient.

12. The method of claim 11, wherein the method further comprises monitoring the extent of cancer-associated cachexia responsive to the administration.

13. A method of treating a patient having AML or MDS, comprising administering an unconjugated humanized M195 antibody to the patient at a dose of 1.5 to about 12 mg/kg body weight,
whereby progression of the AML or MDS is inhibited,
wherein the patient is at least 60 years of age, and
wherein the patient has AML and the humanized M195 antibody is administered in combination with cytarabine.

14. A method of preventing or delaying recurrence of an acute myeloid leukemia (AML) or myelodysplastic syndromes (MDS), comprising:
  administering to a patient in remission from the AML or MDS an unconjugated humanized M195 antibody at a dose of 1.5 to about 12 mg/kg,
  whereby recurrence of the AML or MDS is delayed or prevented.

15. The method of claim 14, wherein the AML is resistant to chemotherapy.

16. The method of claim 14, wherein the humanized M195 antibody is administered in combination with at least one chemotherapeutic agent effective against cancer.

17. The method of claim 16, wherein the chemotherapeutic agent is Velcade® (bortezomib), Revlimid® (lenalidomide), Vidaza® (azacytidine), Dacogen® (Decitabine) or cytarabine.

18. The method of claim 14, wherein the patient is free of detectable cells of the AML or MDS.

19. The method of claim 14, wherein the patient in remission has undergone a bone marrow transplant.

20. The method of claim 19, wherein the bone marrow transplant is an autologous bone marrow transplant.

21. The method of claim 14, wherein the patient is at least 60 years of age.

22. A method of treating AML or MDS in a patient, or of preventing or delaying recurrence of AML or MDS in a patient in remission, comprising administering an unconjugated humanized M195 antibody to the patient at a dose of 550-650 mg regardless of body weight, wherein the humanized M195 antibody is administered in combination with at least one chemotherapeutic agent effective against cancer.

23. The method of claim 22, wherein the chemotherapeutic agent is Velcade® (bortezomib), Revlimid® (lenalidomide), Vidaza® (azacytidine), Dacogen® (Decitabine) or cytarabine.

24. The method of claim 23, wherein the chemotherapeutic agent is Revlimid® (lenalidomide).

25. The method of claim 23, wherein the chemotherapeutic agent is Vidaza® (azacytidine).

26. The method of claim 23, wherein the chemotherapeutic agent is cytarabine.

27. A method of treating AML or MDS in a patient, or of preventing or delaying recurrence of AML or MDS in a patient in remission, comprising administering an unconjugated humanized M195 antibody to the patient at a dose of 550-650 mg regardless of body weight, whereby at least one symptom of AML associated cachexia is reduced, and wherein the AML or MDS is CD33-negative.

28. A method of treating AML or MDS in a patient, or of preventing or delaying recurrence of AML or MDS in a patient in remission, comprising:
  (i) administering an unconjugated humanized M195 antibody to the patient at a dose of 550-650 mg regardless of body weight, and
  (ii) monitoring in the patient:
    (a) the levels of one or more inflammatory cytokines, chemokines or growth factors,
    (b) the number of involved non-malignant effector cells, or
    (c) the extent of cancer-associated cachexia responsive to the administration.

29. The method of claim 28, wherein the one or more inflammatory cytokines, chemokines or growth factors are interleukin-1β (IL-1β), tumor necrosis factor-α (TNF-α), interleukin-6 (IL-6), interleukin-8 (IL-8), interferon-γ (IFN-γ), vascular endothelial growth factor (VEGF), leukemia inhibitory factor (LIF), monocyte chemoattractant protein-1 (MCP-1), RANTES, interleukin-10 (IL-10), interleukin-12 (IL-12), matrix metalloproteinase 2 (MMP2), IP-10, macrophage inflammatory protein 1α (MIP1α) and/or macrophage inflammatory protein 1β (MIP1β).

30. A method of treating AML or MDS in a patient, or of preventing or delaying recurrence of AML or MDS in a patient in remission, comprising administering an unconjugated humanized M195 antibody to the patient at a dose of 550-650 mg regardless of body weight, wherein the patient has AML and is at least 60 years of age, and the humanized M195 antibody is administered in combination with cytarabine.

31. A method of preventing or delaying recurrence of AML or MDS in a patient in remission, comprising administering an unconjugated humanized M195 antibody to the patient at a dose of 550-650 mg regardless of body weight, wherein the antibody is administered in order to prevent or delay recurrence of AML or MDS in the patient in remission, and the patient is free of detectable cells of the AML or MDS.

32. A method of preventing or delaying recurrence of AML or MDS in a patient in remission, comprising administering an unconjugated humanized M195 antibody to the patient at a dose of 550-650 mg regardless of body weight, wherein the antibody is administered in order to prevent or delay recurrence of AML or MDS in the patient in remission, and the patient has undergone a bone marrow transplant.

33. A method of treating AML or MDS in a patient, or of preventing or delaying recurrence of AML or MDS in a patient in remission, comprising administering an unconjugated humanized M195 antibody to the patient at a dose of 600 mg regardless of body weight.

34. A method of treating AML or MDS in a patient, or of preventing or delaying recurrence of AML or MDS in a patient in remission, comprising administering an unconjugated humanized M195 antibody to the patient at a dose of about 600 mg regardless of body weight in combination with cytarabine.

35. A method of treating AML or MDS in a patient, or of preventing or delaying recurrence of AML or MDS in a patient in remission, comprising administering an unconjugated humanized M195 antibody to the patient at a dose of about 600 mg regardless of body weight, and wherein the AML or MDS is CD33-negative.

36. A method of treating AML or MDS in a patient, or of preventing or delaying recurrence of AML or MDS in a patient in remission, comprising:
  (i) administering an unconjugated humanized M195 antibody to the patient at a dose of about 600 mg regardless of body weight, and
  (ii) monitoring in the patient:
    (a) the levels of one or more inflammatory cytokines, chemokines or growth factors,
    (b) the number of involved non-malignant effector cells, or
    (c) the extent of cancer-associated cachexia responsive to the administration.

37. A method of treating AML in a patient, or of preventing or delaying recurrence of AML in a patient in remission, comprising administering an unconjugated humanized M195 antibody to the patient at a dose of about 600 mg regardless of body weight in combination with cytarabine, wherein the patient is at least 60 years of age.

38. A method of preventing or delaying recurrence of AML or MDS, comprising administering an unconjugated humanized M195 antibody to a patient in remission from the AML or MDS at a dose of about 600 mg regardless of body weight, wherein the patient is free of detectable cells of the AML or MDS or has undergone a bone marrow transplant.

* * * * *